(12) United States Patent
Reed et al.

(10) Patent No.: US 7,371,383 B2
(45) Date of Patent: May 13, 2008

(54) RECOMBINANT ANTI-INTERLEUKIN-9 ANTIBODIES

(75) Inventors: Jennifer Lynne Reed, Clarksburg, MD (US); William Dall'Acqua, Gaithersburg, MD (US); Jacques Van Snick, Wezembeek-Oppem (BE); Jean-Christophe Renauld, Kraainem (BE); Francoise Cormont, Rixensart (BE); Catherine Uyttenhove, Louvain-La-neuve (BE)

(73) Assignees: MedImmune, Inc., Gaithersburg, MD (US); Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 10/412,703

(22) Filed: Apr. 11, 2003

(65) Prior Publication Data

US 2003/0219439 A1 Nov. 27, 2003

Related U.S. Application Data

(60) Provisional application No. 60/371,728, filed on Apr. 12, 2002, provisional application No. 60/371,683, filed on Apr. 12, 2002.

(51) Int. Cl.
*A61K 39/395* (2006.01)

(52) U.S. Cl. .............. 424/145.1; 530/388.23; 424/133

(58) Field of Classification Search ............. 424/133.1; 530/387.1
See application file for complete search history.

(56) References Cited

U.S. PATENT DOCUMENTS

| | | | |
|---|---|---|---|
| 4,474,893 A | 10/1984 | Reading | |
| 4,658,019 A | 4/1987 | Kung et al. | |
| 4,714,681 A | 12/1987 | Reading | |
| 4,925,648 A | 5/1990 | Hansen et al. | |
| 5,017,691 A | 5/1991 | Lee et al. | |
| 5,136,021 A | 8/1992 | Dembinski et al. | |
| 5,147,638 A | 9/1992 | Esmon et al. | |
| 5,149,780 A | 9/1992 | Plow et al. | |
| 5,157,112 A | 10/1992 | Van Snick et al. | |
| 5,196,511 A | 3/1993 | Plow et al. | |
| 5,204,445 A | 4/1993 | Plow et al. | |
| 5,208,218 A | 5/1993 | Van Snick et al. | |
| 5,223,395 A | 6/1993 | Gero | |
| 5,231,024 A | 7/1993 | Moeller et al. | |
| 5,262,520 A | 11/1993 | Plow et al. | |
| 5,306,620 A | 4/1994 | Ginsberg et al. | |
| 5,334,380 A | 8/1994 | Kilbourn et al. | |
| 5,360,716 A | 11/1994 | Ohmoto et al. | |
| 5,426,181 A | 6/1995 | Lee et al. | |
| 5,436,154 A | 7/1995 | Barbanti et al. | |
| 5,478,725 A | 12/1995 | Lessey | |
| 5,498,694 A | 3/1996 | Ruoslahti | |
| 5,523,209 A | 6/1996 | Ginsberg et al. | |
| 5,573,920 A | 11/1996 | Randle | |
| 5,578,704 A | 11/1996 | Kim et al. | |
| 5,589,570 A | 12/1996 | Tamura et al. | |
| 5,601,819 A | 2/1997 | Wong et al. | |
| 5,610,279 A | 3/1997 | Brockhaus et al. | |
| 5,644,034 A | 7/1997 | Rathjen et al. | |
| 5,652,109 A | 7/1997 | Kim et al. | |
| 5,652,110 A | 7/1997 | Kim et al. | |
| 5,656,272 A | 8/1997 | Le et al. | |
| 5,658,746 A | 8/1997 | Coan et al. | |
| 5,693,612 A | 12/1997 | Jonczyk et al. | |
| 5,698,195 A | 12/1997 | Le et al. | |
| 5,705,481 A | 1/1998 | Jonczyk et al. | |
| 5,736,138 A | 4/1998 | Pfizenmaier et al. | |
| 5,741,488 A | 4/1998 | Feldman et al. | |
| 5,753,230 A | 5/1998 | Brooks et al. | |
| 5,767,071 A | 6/1998 | Palladino et al. | |
| 5,770,565 A | 6/1998 | Cheng et al. | |
| 5,780,426 A | 7/1998 | Palladino et al. | |
| 5,808,029 A | 9/1998 | Brockhaus et al. | |
| 5,817,457 A | 10/1998 | Bird et al. | |
| 5,824,307 A | 10/1998 | Johnson | |
| 5,830,678 A | 11/1998 | Carter | |
| 5,849,692 A | 12/1998 | Jonczyk et al. | |
| 5,919,452 A | 7/1999 | Le et al. | |
| 5,955,572 A | 9/1999 | Ruoslahti et al. | |
| 5,958,412 A | 9/1999 | Welt et al. | |

(Continued)

FOREIGN PATENT DOCUMENTS

EP 555 880 8/1993

(Continued)

OTHER PUBLICATIONS

Rudikoff et al., Single amino acid substitution altering antigen-binding specificity, 1982, Proc. Natl. Acad. Sci. USA, 79:1979-1983.*
Janeway et al., Immunobiology, 6th Ed., Garland Science, 2004, p. 110-112.*
MacCallum et al. J. Mol. Biol. (1996) 262, 732-745.*
Casset et al. (2003) BRC 307, 198-205.*

(Continued)

*Primary Examiner*—Christina Chan
*Assistant Examiner*—Yunsoo Kim
(74) *Attorney, Agent, or Firm*—Jonathan Klein-Evans

(57) ABSTRACT

The application describes neutralizing chimeric and humanized anti-human IL-9 antibodies, and the use thereof to identify neutralizing epitopes on human IL-9 and as medicaments to prevent and treat asthma, bronchial hyperresponsiveness, atopic allergy, and other related disorders. Particularly disclosed are recombinant antibodies derived from three murine anti-human IL-9 antibodies identified infra as MH9A3, MH9D1, and MH9L1.

44 Claims, 20 Drawing Sheets

U.S. PATENT DOCUMENTS

| | | | |
|---|---|---|---|
| 5,959,087 | A | 9/1999 | Rathjen et al. |
| 5,968,741 | A | 10/1999 | Plevy et al. |
| 5,985,278 | A | 11/1999 | Mitjans et al. |
| 5,994,510 | A | 11/1999 | Adair et al. |
| 6,036,978 | A | 3/2000 | Gombotz et al. |
| 6,048,861 | A | 4/2000 | Askew et al. |
| 6,090,944 | A | 7/2000 | Hutchinson |
| 6,096,707 | A | 8/2000 | Heino et al. |
| 6,114,517 | A | 9/2000 | Monia et al. |
| 6,130,231 | A | 10/2000 | Wityak et al. |
| 6,153,628 | A | 11/2000 | Jin et al. |
| 6,160,099 | A | 12/2000 | Jonak et al. |
| 6,162,432 | A | 12/2000 | Wallner et al. |
| 6,171,588 | B1 | 1/2001 | Carron et al. |
| 6,171,787 | B1 | 1/2001 | Wiley |
| 6,261,559 | B1 | 7/2001 | Levitt et al. |

FOREIGN PATENT DOCUMENTS

| | | |
|---|---|---|
| WO | WO 92/05793 | 4/1992 |
| WO | WO 96/40210 * | 12/1996 |
| WO | WO 96/40210 A1 | 12/1996 |
| WO | WO 98/08545 * | 3/1998 |

OTHER PUBLICATIONS

Vajdos et al. J. Mol. Biol. (2002) 320, 415-428.*
Holm et al, Molecular Biology,2007, vol. 44, 1075-1084.*
Ashkenazi et al., 1991, "Protection against endotoxic shock by a tumor necrosis factor receptor immunoadhesin," Proc. Natl. Acad. Sci. USA 88(23):10535-10539.
Bani et al., 2002, "Inhibitory effects of relaxin on human basophils activated by stimulation of the Fc epsilon receptor, The role of nitric oxide," Int. Immunopharmacol. 2(8):1195-1204.
Beeler et al., 1989, "Neutralization epitopes of the F glycoprotein of respiratory syncytial virus: effect of mutation upon fusion function," J. Virol. 63(7):2941-2950.
Busse et al., 2001, "Anti-immunoglobulin E for the treatment of allergic disease," Curr. Opin. Allergy Clin. Immunol. 1(1):105-108.
Cao et al., 1996, "Kringle domains of human angiostatin. Characterization of the anti-proliferative activity on endothelial cells," J. Biol. Chem. 271(46):29461-29467.
Carrell, 1999, "How serpins are shaping up," Science 285(5435):1861.
Corren et al., 2003, "Omalizumab, a recombinant humanized anti-IgE antibody, reduces asthma-related emergency room visits and hospitalizations in patients with allergic asthma," J. Allergy Clin. Immunol. 111(1):87-90.
Crowley et al., 1993, "Prevention of metastasis by inhibition of the urokinase receptor," Proc. Natl. Acad. Sci. USA 90(11):5021-5025.
Durie et al., 1994, "The role of CD40 in the regulation of humoral and cell-mediated immunity," Immunol. Today 15(9):406-411.
Finn et al., 2003, "Omalizumab improves asthma-related quality of life in patients with severe allergic asthma," J. Allergy Clin. Immunol. 111(2):278-284.
Finotto et al., 1997, "Glucocorticoids decrease tissue mast cell 1 number by reducing the production of the c-kit ligand, stem cell factor, by resident cells: in vitro and in vivo evidence in murine systems," J. Clin. Invest. 99(7):1721-1728.
GenBank Accession No. AAC17735, May 29, 1998.
GenBank Accession No. A60480, Jul. 16, 1999.
GenBank Accession No. NM_176786, Aug. 23, 2004.
GenBank Accession No. NM_002186, Aug. 23, 2004.
GenBank Accession No. NM_000590, Oct. 26, 2004.
GenBank Accession No. NM_000206, Oct. 26, 2004.
GenBank Accession No. NP_789743, Aug. 23, 2004.
GenBank Accession No. NP_002177, Aug. 23, 2004.
GenBank Accession No. NP_000584, Oct. 28, 2004.
GenBank Accession No. NP_000197, Oct. 26, 2004.
Goodson et al., 1994, "High-affinity urokinase receptor antagonists identified with bacteriophage peptide display," Proc. Natl. Acad. Sci. USA 91(15):7129-7133.
He et al., 2003, "The inhibition of mast cell activation by neutrophil lactoferrin: uptake by mast cells and interaction with tryptase, chymase and cathepsin G," Biochem. Pharmacol. 65(6):1007-1015.
Heinrich et al., 2000, "Inhibition of c-kit receptor tyrosine kinase activity by STI 571, a selective tyrosine kinase inhibitor," Blood 96(3):925-932.
Ito et al., 1999, "FK506 and clycosporin A inhibit stem cell factor-dependent cell proliferation/survival, while inducing upregulation of c-kit expression in cells of the mast cell line MC/9," Arch. Dermatol. Res. 291(5):275-283.
Johnson et al., 1997, "Development of a humanized monoclonal antibody (MEDI-493) with potent in vitro and in vivo activity against respiratory syncytial virus," J. Infect. Dis. 176(5):1215-24.
Kohno et al., 1990, "A second tumor necrosis factor receptor gene product can shed a naturally occuring tumor necrosis factor inhibitor," Proc. Natl. Acad. Sci. USA 87(21):8331-8335.
Kostelny et al., 1992, J. Immunol. 148:1547-1553.
Leung et al., 2003, "Effect of anti-IgE therapy in patients with peanut allergy," N. Engl. J. Med. 348(11):986-993.
Mendiaz et al., 1996, "Epitope mapping and immunoneutralization of recombinant human stem-cell factor," Eur. J. Biochem. 239(3):842-849.
Metcalfe et al., 1995, "Mast cell ontogeny and apoptosis," Exp. Dermatol. 4(4 Pt 2):227-230.
Min et al., 1996, "Urokinase receptor antagonists inhibit angiogenesis and primary tumor growth in syngeneic mice," Cancer Res. 56(10):2428-2433.
Miyajima et al., 2002, "Rat monoclonal anti-murine IgE antibody removes IgE molecules already bound to mast cells or basophilic leukemia cells, resulting in the inhibition of systemic anaphylaxis and passive cutaneous anaphylaxis," Int. Arch. Allergy Immunol. 128(1):24-32.
Nagai et al., 1995, "Pharmacological study of stem-cell-factor-induced mast cell histamine release with kinase inhibitors," Biochem. Biophys. Res. Commun. 208(2):576-581.
O'Reilly et al., 1999, "Antiangiogenic activity of the cleaved conformation of the serpin antithrombin," Science 285(5435):1926-1928.
Oswald et al., 1992, "Interleukin 10 inhibits macrophage microbicidal activity by blocking the endogenous production of tumor necrosis factor alpha required as a costimulatory factor for interferon gamma-induced activation," Proc. Natl. Acad. Sci. USA 89(18):8676-8680.
Press et al., 1970, "The amino acid sequences of the Fd fragments of two human gamma-1 heavy chains," Biochem. J. 117(4):641-660.
Seckinger et al., 1990, "Characterization of a tumor necrosis factor alpha (TNF-alpha) inhibitor: evidence of immunological cross-reactivity with the TNF receptor," Proc. Natl. Acad. Sci. USA 87(13):5188-5192.
Takahashi et al., 1984, "Rearranged immunoglobulin heavy chain variable region (VH) pseudogene that deletes the second complementarity-determining region," Proc. Natl. Acad. Sci. USA 81(16):5194-5198.
Tang et al., 2001, "Childhood asthma as an allergic disease: rationale for the development of future treatment," Eur. J. Pediatr. 160(12):696-704.
Temkin et al., 2002, "Tryptase activates the mitogen-activated protein kinase/activator protein-1 pathway in human peripheral blood eosinophils, causing cytokine production and release," J. Immunol. 169(5):2662-2669.
Thorbecke et al., 1992, "Involvement of endogenous tumor necrosis factor alpha and transforming growth factor beta during induction of collagen type II arthritis in mice," Proc. Natl. Acad. Sci. USA 89(16):7375-7379.
Tutt et al., 1991, J. Immunol. 17:60-69.
Van Neerven et al., 2001, "Humanized anti-IgE mAb Hu-901 prevents the activation of allergen-specific T cells," Int. Arch. Allergy Immunol. 124(1-3):400-402.
Van Snick et al., 1989, "Cloning and characterization of a cDNA for a new mouse T cell growth factor (P40)," J. Exp. Med. 169(1):363-368.

Vosseller et al., 1997, "c-kit receptor signaling through its phosphatidylinositide-3'-kinase-binding site and protein kinase C: role in mast cell enhancement of degranulation, adhesion, and membrane ruffling," Mol. Biol. Cell. 8(5):909-922.

Williams et al., 1994, "Synergy between anti-CD4 and anti-tumor necrosis factor in the amelioration of established collagen-induced arthritis," Proc. Natl. Acad. Sci. USA 91(7):2762-2766.

Yang et al., 1989, "Expression cloning of cDNA encoding a novel human hematopoietic growth factor: human homologue of murine T-cell growth factor P40," Blood 74(6):1880-1884.

Yokota et al., 1986, "Isolation and characterization of a human interleukin cDNA clone, homologous to mouse B-cell stimulatory factor 1, that expresses B-cell- and T-cell-stimulating activities," Proc. Natl. Acad. Sci. USA 83(16):5894-5898.

Dong et al., 1999, "IL-9 Induces Chemokine Expression in Lung Epithelial Cells and Baseline Airway Eosinophilia in Transgenic Mice," Eur. J. Immunol. 29:2130-2139.

Erpenbeck et al., 2003, "Segmental Allergen Challenge in Patients with Atopic Asthma Leads to Increased IL-9 Expression in Bronchoalveolar Lavage Fluid Lymphocytes," J. Allergy Clin Immunol. 111:1319-27.

Louahed et al., 1995, "IL-9 Induces Expression of Granzymes and High-Affinity IgE Receptor in Murine T Helper Clones[1]," J. Immunol. 154:5061-5070.

Miller et al., 1999, "A Novel Function for Transforming Growth Factor-$\beta_1$: Upregulation of the Expression and the IgE-Independent Extracellular Release of a Mucosal Mast Cell Granule-Specific $\beta$-Chymase, Mouse Mast Cell Protease-1," Blood, 93, 10:3473-3486.

Louahed et al., 2001, "Interleukin 9 Promotes Influx and Local Maturation of Eosinophils," Blood, 97:1035-1042.

Smedt et al., 2000, "Signals from the IL-9 Receptor are Critical for the Early Stages of Human Intrathymic T Cell Development," J. Immunol. 164:1761-1767.

Louahed et al., 1995, "IL-9 Induces Expression of Granzymes and High-Affinity IgE Receptor in Murine T Helper Clones," J. Immunol. 154:5061-5070.

Vink et al., 1999, "Interleukin 9-Induced in Vivo Expansion of the B-1 Lymphocyte Population," J. Exp. Med 189:1413-1423.

McDermott et al., 2003, "Mast Cells Disrupt Epithelial Barrier Function During Enteric Nematode Infection," Proc. Natl. Acad. Sci. USA, 100:7761-7766.

Abdelilah et al., 2001, "Functional Expression of IL-9 Receptor by Human Neutrophils from Asthmatic Donors: Role in IL-8 Release[1]," J. Immunol. 166:2768-2774.

Renauld et al, 1992, "Expression Cloning of the Murine and Human Interleukin 9 Receptor cDNAs," Proc. Nat. Acad. Sci. USA89:5690-5694.

Rosenwasser, 1999, "Promoter Polymorphism in the Candidate Genes, IL-4, IL-9, TFG-$\beta$1, for Atopy and Asthma," Int. Arch Allergy Immunol., 118: 268-270.

Eklund et al., 1993, "Induction by IL-9 and Suppression by IL-3 and IL-4 of the Levels of Chromosome 14-Derived Transcripts that Encode Late-Expressed Mouse Mast Cell Proteases," J. Immunol., 151: 4266-4273.

Lauder et al., 2004, "Lymphomagenesis, Hydronephrosis, and Autoantibodies Result from Dysregulation of IL-9 and are Differentially Dependent on Th2 Cytokines," J. Immunol. 173: 113-122.

McLane et al., 1998, "Interleukin-9 Promotes Allergen-Induced Esoinophilic Inflammation and Airway Hyperresponsiveness in Transgenic Mice," Am. J. Respir. Cell Mol. Biol. 19:713-720.

Reader et al., 2003, "Interleukin-9 Induces Mucous Cell Metaplasia Independent of Inflammation," Am. J. Respir. Cell Mol. Biol. 28: 664-672.

Pilette et al., 2002, "Oxidateive Burst in Lipopolysaccharide-Activated Human Alveolar Macrophages is Inhibited by Interleukin-9,"Eur Respir J., 20: 1198-1205.

Postma et al., 1995, "Genetic Susceptibility to Asthma—Bronchial Hyperresponsiveness Coinherited with a Major Gene for Atopy," N. Engl. J.Med., 333: 894-900.

Kung et al., 2001, "Effect of Anti-mIL-9 Antibody on the Development of Pulmonary Inflammation and Airway Hyperresponsiveness in Allergic Mice," Am. J. Respir. Cell Mol. Biol., 25:600-605.

Richard et al., 2000, "Anti-IL9 Vaccination Prevents Worm Expulsion and Blood Eosinophilia in Trichuris Muris-Invected Mice," PNAS 97: 767-772.

Erpenbeck et al., 2003, "Increased Expression of Interleukin-9 Messenger RNA after Segmental Allergen Challenge in Allergic Asthmatics," Chest J. 123: 370S.

Gounni et al., 2000, "Interleukin-9 Enhances Interleukin-5 Receptor Expression, Differentiation, and Survival of Human Eosinophils," Blood, 96: 2163-2171.

Godfraind et al., 1998, "Intraepithelial Infiltration by Mast Cells with Both Connective Tissue-Type and Mucosal Type Characteristics in Gut, Trachea, and Kidneys of IL-9 Transgenic Mice," J. Immunol. 160:3989-3996.

Nicolaides et al., 1997, "Interleukin 9: A Candidate Gene for Asthma," Proc. Natl. Acad. Sci. USA, 94:13175-13180.

Louahed et al., 2000, "Interleukin-9 Upregulates Mucus Expression in the Airways," Am. J. Respir. Cell Mol. Biol., 22:649-656.

Lange et al., 2003, "Overexpression of NPM-ALK Induces Different Types of Malignant Lymphomas in IL-9 Transgenic Mice," Oncogene, 22:517-527.

Temann et al., 2002, "Pulmonary Overexpression of IL-9 Induces Th2 Cytokine Expression, Leading to Immune Pathology," J. Clin. Invest., 109:29-39.

Druez et al., 1990, "Functional and Biochemical Characterization of Mouse P40/IL-9 Receptors," J. Immunol., 145: 2494-2499.

Temann et al., 1998, "Expression of Interleukin 9 in the Lungs of Transgenic Mice Causes Airway Inflammation, Mast Cell Hyperplasia, and Bronchial Hyperresponsivenss," J. Exper. Med., 188:1307-1320.

Holt, et al., "Domain antibodies: proteins for therapy," TRENDS in Biotechnology, 2003; vol. 21, No. 11:484-490.

van den Beucken, et al., "Building Novel Binding Ligands to B7.1 and B7.2 Based on Human Antibody Single Variable Light Chain Domains," J. Mol. Biol., 2001; 310:591-601.

Spinelli, et al., "Camelid Heavy-Chain Variable Domains Provide Efficient Combining Sites to Haptens," Biochemistry, 2000; 39:1217-1222.

Martin, et al., "Affinity selection of a camelized VH domain antibody inhibitor of hepatitis C virus NS3 protease," Protein Engineering, 1997; vol. 10, No. 5:607-614.

Ghahroudi, et al., "Selection and identication of single domain antibody fragments from camel heavy-chain antibodies," FEBS Letters 414, 1997; 521-526.

Ward, et al., "Binding activities of a repertoire of single Immunoglobulin variable domains secreted from *Escherichia coli*," Nature, 1989; vol. 341:544-546.

Davies, et al., "Antibody VH Domains as Small Recognition Units," Biotechnology, 1995; vol. 13:475-479.

Soderlind, et al., "The Immune Diversity in a Test Tube—Non-Immunised Antibody Libraries . . . ," Combinatorial Chemistry & High Throughput Screening, 2001; vol. 4, No. 5:409-416.

Klimka, et al., "Human anti-CD30 recombinant antibodies by guided phage antibody selection using cell panning," British Journal of Cancer, 2000; 83(2):252-260.

Marks, et al., "By-Passing Immunization: Building High Affinity Human Antibodies by Chain Suffling," Biotechnology, 1992; vol. 10:779-783.

Rader, et al., "A phage display approach for rapid antibody humanization: Designed combinatorial V gene libraries," PNAS, 1998; vol. 95:8910-8915.

Yang, et al., "CDR Walking Mutagenesis for the Affinity Maturation of a Protein Human Anti-HIV-1 Antibody into the Picmolar Range," J. Mol. Biol., 1995; 254:392-403.

Barbas, et al., "In vitro evolution of a neutralizing human antibody to human immunodeficiency virus type 1 to enhance affinity . . . ," PNAS, 1994; vol. 91:3809-3813.

Wu, et al., "Stepwise in vitro affinity maturation of Vitaxin, an avB3-specific humanized mAb," PNAS, 1998; vol. 95:6037-6042.

Gruss et al., 1992, "Interleukin 9 Is Expressed By Primrary and Cultured Hodgkin and Reed-Sternberg Cells", Cancer Res. 52:1026-1031.

* cited by examiner

GACATTGTGA TGACCCAGTC TCAAAAATTC ATGCCCACAT CAGTAGGAGA CAGGGTCAGC 60

GTCACCTGCA AGGCCAGTCA GCATGTGGGT ACTCATGTAA CCTGGTATCA ACAGAAACCA 120

GGGCAATCTC CTAAAGCACT GATTTACTCG ACATCCTACC GGTACAGTGG AGTCCCTGAT 180

CGCTTCACAG GCAGTGGATC TGGGACAGAT TTCACTCTCA CCATCACCAA TGTGCAGTCT 240

GAAGACTTGG CAGAGTATTT CTGTCAGCAA TTTTACAGCT ATCCTCTCAC GTTCGGTGCT 300

GGGACCAAGC TGGAGCTGAA ACGGGCTGAT GCTGCACCAA CTGTATCCAT CTTCCCACCA 360

FIGURE 1

```
CAGGTTCAGC TGCAGCAGTC TGGAGCTGAG CTGATGAAGC CTGGGACCTC AGTGAAGCTT    60
TCCTGCAAGG CTACTGGCTA CACATTCACT GGCTACTGGA TAGAGTGGAT AAAGCGGAGG   120
CCTGGACATG GCCTTGAGTG GCTTGGAGAG ATTTTACCTG GAAGTGGTAC TACTAACTAC   180
AATGAGAAGT TCAAGGGCAA GGCCACATTC CCTGCAGATA CATCCTCCAA CACAGCCTAC   240
ATGCAACTCA GCAGCCTGAC AACTGAGGAC TCTGCCATCT ATTACTGTGC AAGAGCGGAT   300
TACTACGGTA GTAGTTACGT CAAGTTTGAC TACTGGGGCC AAGGCACCAC TCTCACAGTC   360
TCCTCA                                                              366
```

FIGURE 2

HEAVY CHAINS

|  | FR1 | CDR1 | FR2 | CDR2 |
|---|---|---|---|---|
| hA1/A2: | QVQLQQSGAELMKPGASVKLSCKAT | GYTFTGYWLE | WVKQRPGHGLEWI | GEILPGSGSSNFNEKFKGK |
| hA3: | QVQLQQSGAELMKPGTSVKLSCKAT | GYTFTGYWLE | WIKRRPGHGLEWL | GEILPGSGTTNYNEKFKGK |
| hL1: | QVQLQQSGAELMKPGASVKLSCKAT | GYTFTGSWIE | WIKQRPGHGLFWI | GQILPGSGSAYYNEKFKGK |
| hD1: | QVQLQQSGAELVRPGTSVKMSCKAS | GFTFTNYYIH | WAKQRPGHGLEWI | GDIYPGSTYINYNEKFKSK |
| hA4: | QVQLQQPGTELVKPGASVKLSCKAS | GYTFTSYWMH | WVKQRPGPGLEWIG | NINPRNGDTNYNEKFKSK |

|  | FR3 | CDR3 | FR4 |
|---|---|---|---|
| hA1/A2: | ATFTSDTSSNTAYMQLSSLTTEDSAIYYCAR | --WLYYGNSW--FAY | WGQGTLVTVSA |
| hA3: | ATFPADTSSNTAYMQLSSLTTEDSAIYYCAR | --ADYWGSSYVKFDV | WGQGTTLTVSS |
| hL1: | ATFTADTSSKIVYIQLISITTEDSAIYYCAR | --EDNWGSS--SLAY | WGQGTLLTVSA |
| hD1: | ATLTADKSSSTAYMQFSSLISEDSAVYYCAR | SDDGYYG---FPY | WGQGTLVTVSA |
| hA4: | ATLTVDKSSSTAYMQLSSLTSEDSAVYYCAR | GGWFGY------- | WGQGTLVTVSA |

FIGURE 3

LIGHT CHAINS

```
            FR1                          CDR1              FR2             CDR2

1A1/A2: DIQMNQSPSSLSASLGTITITCHASQNINVWLS----WYQQKPGNIPKLIYKASNLHTGVPSRFS
1A3:    DIVMTQSQKFMPTSVGDRVSVTCKASQHVGTHVT---WYQQKPGQSPKALIYSTSYRYSGVPDRFT
1L1:    DILLTQSPAILSVSPGERVSFSCRASQSIGTNIH----WYQQRTNGSPRLLIKYASESISGIPSRFS
1D1:    DILMTQSPSSMSVSLGDTVSITCHASQDIGSNIG----WLQQKPGKSFKGLIYHGSNLEDGVPSRFS

1A4:    DIVLTQSPASLAVSLGQRATIFCRASQSVDYNGISYMYWFQQKPGQPPKLLIYVASNLESGIPARFS
```

```
            FR3                          CDR3              FR4

1A1/A2: GSGSGTGFTLTISSLQPEDIATYCQQGQSYPLTFGAGTKLELKR
1A3:    GSGSGTDFTLTITNVQSEDLAEYFCQQFYSYPLTFGAGTKLELKR
1L1:    GGGSGTDFTLSINSVESEDIADYYCQQSNNWPLTFGAGTKLELKR
1D1:    GSGSGADYSLTINSLESEDFADYYGVQFAQFPYTFGGGTKLEMKR

1A4:    GSGSGTDFTLNIHPVEEEDAATYCLQSIEDPYTFGGGTKLEIKR
```

FIGURE 4

A3-Heavy Chain Humanization

```
A3:          QVQLQQSGAELMKPGTSVKLSCKATGYTFTGYWIEWIKRRPGHGLEWLGEILPGSCTTNYNEKFKGK
VH 1-69:     QVQLVQSGAEVKKPGSSVKVSCKASGGTFS----WVRQAPGQGLEWMG---------------R
HumH1(1-69): QVQLVQSGAEVKKPGSSVKVSCKASGYTFTGYWIEWVRQAPGQGLEWMGEILPGSCTTNYNEKFKGR
VH 5-51:     EVQLVQSGAEVKKPGESLKISCKGSGYSFT----WVRQMPGKGLEWMG---------------Q
HumH2(5-51): EVQLVQSGAEVKKPGESLKISCKGSGYTFTGYWIEWVRQMPGKGLEWMGEILPGSCTTNYNEKFKGQ

A3:          ATFPADTSSNTAYMQLSSITTEDSAIYYCARADYYGSSYVKFDYWGQGTTLTVSS
VH 1-69:     VTITADKSTSTAYMELSSLRSEDTAVYYCAR------------WGQGTLVTVSS
HumH1(1-69): VTITADKSTSTAYMELSSLRSEDTAVYYCARADYYGSSYVKFDYWGQGTLVTVSS
VH 5-51:     VTISADKSISTAYLQWSSLKASDTAMYYCAR------------WGQGTLVTVSS
HumH2(5-51): VTISADKSISTAYLQWSSLKASDTAMYYCARADYYGSSYVKFDYWGQGTLVTVSS
```

Bold: Canonical + Vernier Residues
▨ : CDRs (Kabat)
▩ : Donor Residues

FIGURE 6

A3-Light Chain Humanization

```
A3:       DIVMTQSQKFMPTSVGDRVSVTCKASQHVGTHVTWYQQKPGQSPKALIYSTSYRYSGVPDRFTGSGS
B3:       DIVMTQSPDSLAVSLGERATINC---------------WYQQKPGQPPKLLIY-------GVPDRFSGSGS
HumL1(B3):DIVMTQSPDSLAVSLGERATINCKASQHVGTHVTWYQQKPGQPPKLLIYSTSYRYSGVPDRFSGSGS

A3:       GTDFTLTITNVQSEDLAEYFCQQFYSYPLTFGAGTKLELK
B3:       GTDFTLTISSLQAEDVAVYYC---------FGGGTKVEIK
HumL1(B3):GTDFTLTISSLQAEDVAVYYCQQFYSYPLTFGGGTKVEIK
```

Bold: Canonical + Vernier Residues
- ░░ CDRs (Kabat)
- ▒▒ Donor Residues

FIGURE 7

D1-Light Chain Humanization

```
D1:         DILMTQSPSSMSVSLGDTVSITCHASQDIGSNIGWLQQKPGKSFKGLIYHGSNLEDGVPSRFSGSGS
L1:         DIQMTQSPSSLSASVGDRVTITC-------------WFQQKPGKAPKSLIY---GVPSRFSGSGS
HumL1(L1):  DIQMTQSPSSLSASVGDRVTITCHASQDIGSNIGWFQQKPGKAPKSLIYHGSNLEDGVPSRFSGSGS

D1:         GADYSLTINSLESEDFADYYCVQFAQFPYTFGGGTKLEMK
L1:         GTDFTLTISSLQPEDFATYYC--------FGQGTKLEIK
HumL1(L1):  GTDFTLTISSLQPEDFATYYCVQFAQFPYTFGQGTKLEIK
```

Bold: Canonical + Vernier Residues
▨ CDRs (Kabat)
▨ Donor Residues

FIGURE 9

A3-Humanized Light Chain Optimization

A3: DIVMTQSQKFMPTSVGDRVSVTCKASQHVGTHVTWYQQKPGQSPKALIYSTSYRYSGVPDRFTGSGSGTDFTLTITNVQSEDLAEYFCQQFYSYPLTFGAGTKLELK

A3 (B3):
```
DIVMTQSQKFMPTSVGDRVSVTCKASQHVGTHVTWYQQKPGQSPKALIYSTSYRYSGVPDRFTGSGSGTDFTLTITNVQSEDLAEYFCQQFYSYPLTFGAGTKLELK
DIVMTQSPDSLAVSLGERATINCKASQHVGTHVTWYQQKPGQSPKLLIYSTSYRYSGVPDRFSGSGSGTDFTLTISSLQAEDVAVYYCQQFYSYPLTFGGGTKVEIK
DIVMTQSPDSLAVSLGERATINCKASQHVGTHVTWYQQKPGQSPKLLIYSTSYRYSGVPDDRFSGSGSGTDFTLTISSLQAEDVAVYYCQQFYSYPLTFGGGTKVEIK
DIVMTQSPDSLAVSLGERATINCKASQHVGTHVTWYQQKPGQSPKALIYSTSYRYSGVPDRFSGSGSGTDFTLTISSLQAEDVAVYYCQQFYSYPLTFGGGTKVEIK
DIVMTQSPDSLAVSLGERATINCKASQHVGTHVTWYQQKPGQSPKLLIYSTSYRYSGVPDRFSGSGSGTDFTLTTNVSSLQAEDVAVYYCQQFYSYPLTFGAGTKLELK
DIVMTQSPDSLAVSLGERATINCKASQHVGTHVTWYQQKPGQSPKLLIYSTSYRYSGVPDRFSGSGSGTDFTLTISSLQAEDVAVYYCQQFYSYPLTFGAGTKLELK
DIVMTQSPDSLAVSLGERATINCKASQHVGTHVTWYQQKPGQSPKALIYSTSYRYSGVPDRFSGSGSGTDFTLTISSLQAEDVAVYYCQQFYSYPLTFGAGTKLELK
DIVMTQSPDSLAVSLGERATINCKASQHVGTHVTWYQQKPGQSPKLLIYSTSYRYSGVPDRFSGSGSGTDFTLTISSLQAEDIAVYYCQQFYSYPLTFGAGTKLELK
```

Bold: Canonical + Vernier Residues
▓ : CDRs (Kabat)

FIGURE 11

A3-Light Chain Humanization by Phage Display. 3rd Round of Panning

```
A3:              DIVMTQSQKFMPTSVGDRVSVTCKASQHVGTHVTWYQQKPGQSPKALIYSTSYRYSGVPDRFTGSGSGTDFTLTITNVQSEDLAEYFCQQFYSYPLTFGAGTKLELK
A3/B3:           DIVMTQSPDSLAVSLGERATINCKASQHVGTHVTWYQQKPGQPPKLLIYSTSYRYSGVEDRFSGSGSGTDFTLTISSLQAEDVAVYYCQQFYSYPLTFGQGTKVEIK

11/14/101/69     EIQLTQSPSSLSASVGDTVTITCRASQNINTFLNWYQQKPGKAPVLLIYAASHLQSGVPSRFSGSGSGTEFTLTISSLQSPDFATYYCQQFYSYPLTFGQGTKLEIK
40               EIQMTQSPSSLSASVGDTVTITCRASQGIRNDISWYQQKPGKAPKLLIYAASSLESGVPSRFSGSGSGTDFTLTISSLQPEDFAVYYCQQFYSYPLTFGQGTKLEIK
94               EIQLTQSPSSLSASVGDTVTITCRASQNINTFLNWYQQKPGKAPKLLIYAASFEQNGVPSRFSGSGSGTDFTLTISSLQAEDAGVYYCQQFYSYPLTFGQGTKLEIK

12               EITLTQSPATLSVSPGERATLSCRASQSVSSNLAWYQQKPGQAPRLLIYGASTRATGIPARFSGSGSGTEFTLTISSLQSEDFAVYYCQQFYSYPLTFGQGTKLEIK
84               EITLTQSPATLSVSPGERATLSCRASQSVSSNLAWYQQKPGQAPRLLIYGASTRATGIPARFSGSGSGTEFTLTISSLQSEDFATYYCQQFYSYPLTFGQGTKLEIK
22               EITLTQSPGERATLSVSPGERATLSCRASQSVSSNLAWYQQKPGQAPRLLIYGASSRATGIPDRFSGSGSGTDFTLTISRLEPEDFATYYCQQFYSYPLTFGQGTKLEIK
```

Bold: Canonical + Vernier Residues

FIGURE 15

A3 and L1-Heavy Chain Humanization

```
A3:     QVQLQQSGAELMKPGTSVKLSCKAT GYTFTGYWIE WIKRRPGHGLEWLGE ILPGSGTTNYNEKFKG KATFPADTSSNTAYMQLSSLTTEDSAIYYCAR ADYYGSSYVKFDY WGQGTTLTVSS
L1:     QVQLQQSGAELMKPGASVKLSCKAT GYTFTGSWIE WIKQRPGHGLEWLGQ ILPGSGSAYNEKFKG KATFTADTSSKTVYIQLISLTTEDSAIYYCAR EDNYGSSSLA--Y WGQGTLLTVSA
VH1-69: QVQLVQSGAEVKKPGSSVKVSCKAS GGTFS---- MVRQAPGQGLEWMG ------------- RVTITADKSTSTAYMELSSLRSEDTAVYYCAR-                WGQGTLVTVSS
VH5-51: EVQLVQSGAEVKKPGESLKISCKGS GYSFT---- MVRQMPGKGLEWMG ------------- QVTISADKSISTAYLQWSSLKASDTAMYYCAR-                WGQGTLVTVSS
```

FIGURE 17

A3 and L1-Light Chain Humanization

```
A3:   DIVMTQSQKFMPTSVGDRVSVTCKASQHVGTHVTWYQQKPGQSPKALIYSTSYRYSGVPDRFTGSGSGTDFTLTITNVQSEDLAEYFCQQFYSYPLTFGAGTKLELK
B3:   DIVMTQSPDSLAVSLGERATINC--------------WYQQKPGQPPKLLIY-------GVPDRFSGSGSGTDFTLTISSLQAEDVAVYYC-------FGGGTKVEIK
L1:   DILLTQSPAILSVSPGERVSFSCRASQSIGTNIHWYQQRTNGSPRLLIKYASESISGIPSRFSGGGSGTDFTLSINSVESEDIADYYCQQSNNWPLTFGAGTKLELK
A26:  EIVLTQSPDFQSVTPKEKVTITC--------------WYQQKPDQSPKLLIK-------GVPSRFSGSGSGTDFTLTINSLEAEDAATYYC-------FGGGTKVEIK
L15:  DIQMTQSPSSLSASVGDRVTITC--------------WYQQKPEKAPKSLIY-------GVPSRFSGSGSGTDFTLTISSLQPEDFATYYC-------FGGGTKVEIK
```

FIGURE 18

Heavy Chains

```
A3:      QVQLQQSGAELMKPGTSVKLSCKATGYTFT GYWIE WIKRRPGHGLEWLGE ILPGSGTTNYNEKFKG KATFPADTSSNTAYMQLSSLTTEDSAIYYCAR ADYYGSSYVKFDY WGQGTTLTVSS
A3/169:  QVQLVQSGAEVKKPGSSVKVSCKASGYTFT GYWIE WVRQAPGQGLEMMG ILPGSGTTNYNEKFKG RVTITADKSTSTAYMELSSLRSEDTAVYYCAR ADYYGSSYVKFDY WGQGTTLVTVSS
A3/551:  EVQLVQSGAEVKKPGESLKISCKGSGYTFT GYWIE WVRQMPGKGLEMMG ILPGSGTTNYNEKFKG QVTISADKSISTAYLQWSSLKASDTAMYYCAR ADYYGSSYVKFDY WGQGTLVTVSS

L1:      QVQLQQSGAELMKPGASVKLSCKATGYTFT GSWIE WIKLQKR PGHGLEWIGQ ILPGSGSAYYNEKFKG KATFTADTSSKTVYIQLISLTTEDSAIYYCAR EDNYGSSLAY WGQGTTLVTVSA
L1/169:  QVQLVQSGAEVKKPGSSVKVSCKASGGTFS GSWIE WVRQAPGQGLEMMG ILPGSGSAYYNEKFKG RVTITADKSTSTAYMELSSLRSEDTAVYYCAR EDNYGSSLAY WGQGTLVTVSS
L1/551:  EVQLVQSGAEVKKPGESLKISCKGSGYSFT GSWIE WVRQMPGKGLEMMG QILPGSGSAYYNEKFKG QVTISADKSISTAYLQWSSLKASDTAMYYCAR EDNYGSSLAY WGQGTLVTVSS

D1:      QVQLQQSGAELVRPGTSVKMSCKASGFTFT NYYIG WAKQRPGHGLEWIG DIYPGSTYINYNEKFKG KATLTADKSSSTAYMQFSSLTEDSAIYYCAR SDDGYYGFPY WGQGTTLVTVSA
D1/169:  QVQLVQSGAEVKKPGSSVKVSCKASGGTFS NYYIG WVRQAPGQGLEMMG DIYPGSTYINYNEKFKG RVTITADKSTSTAYMELSSLRSEDTAVYYCAR SDDGYYGFPY WGQGTLVTVSS
D1/321   EVQLVESGGGLVKPGGSLRLSCAASGFTFS NYYIG WVRQAPGKGLEWVS DIYPGSTYINYNEKFKG RFTISRDNAKNSLYLQMNSLRAEDTAVYYCAR SDDGYYGFPY WGQGTLVTVSS
```

Light Chains

```
A3:      DIVMTQSQKFMPTSVGDRVSVTC KASQHVGTHVT WYQQKPGQSVPKALIY STSYRYS GVPDRFTGSGSGTDF TLTITNVQSEDLAEYFC QQFYSYPLT FGAGTKLELK      (murine)
A3/B3:   DIVMTQSPDSLAVSLGERATINC KASQHVGTHVT WYQQKPGQSVPPKALIY STSYRYS GVPDRFSGSGSGTDF TLTISSLQAEDVAVYYC QQFYSYPLT FGGGTKVEIK    (humanized)

L1:      DILLTQSPAILSVSPGERVSFSC RASQSIGTNIH WYQQRTNGSPRLLIK YASESIS GIPSRFSGGGSGTDF TLSINSVESEDIADYYC QQSNNWPLT FGAGTKLELK      (murine)
L1/A26:  EIVLTQSPDFQSVTPKEKVTITC RASQSIGTNIH WYQQKPDQSPKLLIK YASESIS GVPSRFSGSGSGTDF TLTINSLEAEDAATYYC QQSNNWPLT FGQGTKLEIK      (humanized)
L1/L15:  DIQMTQSPSSLSASVGDRVTITC RASQSIGTNIH WYQQKPEKAPKSLIY YASESIS GVPSRFSGSGSGTDF TLTISSLQPEDFATYYC QQSNNWPLT FGQGTKLEIK      (humanized)

D1:      DILMTQSPSSMSVSLGDTVSITC HASQDIGSNIG WLQQKPGKSFKGLIY HGSNLED GVPSRFSGSGSGADY SLTINSLESEDFADYYC VQFAQFPYT FGGGKLEMK       (murine)
D1/L1    DIQMTQSPSSLSASVGDRVTITC HASQDIGSNIG WFQQKPGKAPKSLIY HGSNLED GVPSRFSGSGSGTDF TLTISSLQPEDFATYYC VQFAQFPYT FGQGTKLEIK      (humanized)
```

FIGURE 20

RECOMBINANT ANTI-INTERLEUKIN-9 ANTIBODIES

This application claims the benefit under 35 U.S.C §119(e) of U.S. Provisional Application No. 60/371,728, filed Apr. 12, 2002, and U.S. Provisional Application No. 60/371,683, filed Apr. 12, 2002. Each of these applications are incorporated by reference.

FIELD OF INVENTION

The present invention relates to recombinant antibody molecules, and especially humanized and chimeric antibodies and antibody fragments, having specificity for human interleukin-9 (IL-9). The invention also concerns processes for producing such antibodies, including rational design homology alignment of murine and human antibody sequences, and successive phage display panning of framework libraries. The antibodies are useful e.g., for treating and preventing asthma attacks in human patients. The invention particularly relates to humanized and chimeric antibody molecules derived from several mouse anti-IL-9 monoclonal antibodies, MH9A3, MH9D1, and MH9L1, described infra, and the use in treating asthma and other allergic disorders, as well as disorders involving aberrant mucin production alone or in combination with other asthma drugs.

A preferred non-exclusive embodiment of the invention includes the use of the humanized and chimeric antibody molecules of the invention to treat, prevent, and/or ameliorate bronchial hyperresponsiveness, atopic allergy, and/or asthma in a patient. An additional preferred non-exclusive embodiment of the invention includes the use of the humanized and chimeric antibody molecules of the invention to treat, prevent, and/or ameliorate mucin overproduction, chronic obstructive pulmonary disorder, cystic fibrosis, epithelial cell hyperplasia, excessive T cell, B cell, eosinophil, macrophage, monocyte, neutrophil, or mast cell activity.

BACKGROUND OF INVENTION

Natural immunoglobulins have been known for many years, as have the various fragments thereof, such as the Fab, (Fab')$_2$, Fv and Fc fragments, which can be derived by enzymatic cleavage. A natural immunoglobulin consists of a Y-shaped molecule having two protein chains (heavy and light), and having an antigen-binding site towards the end of each upper arm, generally known as the variable region. The remainder of the structure, generally known as the constant region domain, mediates the effector functions associated with immunoglobulins.

Natural immunoglobulins have been used in assay, diagnosis and, to a more limited extent, therapy. However, such uses, especially in therapy, have been hindered by the polyclonal nature of natural immunoglobulins. The advent of monoclonal antibodies of defined specificity increased the opportunities for therapeutic use. However, most monoclonal antibodies are produced following immunization of a rodent host animal with the target protein, and subsequent fusion of a rodent spleen cell producing the antibody of interest with a rodent myeloma cell. They are, therefore, essentially rodent proteins and as such are naturally antigenic in humans, frequently giving rise to an undesirable immune response termed the HAMA (Human Anti-Mouse Antibody) response.

Many groups have devised techniques to decrease the immunogenicity of therapeutic antibodies. These techniques generally involve the use of recombinant DNA technology to manipulate DNA sequences encoding the polypeptide chains of the antibody molecule. Early methods involved production of chimeric antibodies in which an antigen-binding site comprising the complete variable domains of the rodent antibody is linked to constant domains derived from a human antibody. Methods for carrying out such chimerization procedures are now well known in the art. More recent chimerization procedures have resulted in heteroantibodies comprising both the variable region domain of the target specific antibody chimerized with the variable domains of an antibody specific for Fc receptor. See U.S. Pat. No. 6,071,517 (herein incorporated by reference).

Given that chimeric antibodies still contain a significant proportion of non-human amino acid sequences, i.e. the complete non-human variable domains, they may still elicit some HAMA response. Therefore, other groups developed humanized versions of antibodies wherein the complementarity determining regions (CDRs) of a rodent monoclonal antibody are grafted onto the framework regions of the variable domains of a human immunoglobulin. Winter (EP-A-0239400), for instance, proposed performing such an alteration by site-directed mutagenesis using long oligonucleotides in order to graft three complementarity determining regions (CDR 1, CDR2 and CDR3) from each of the heavy and light chain variable regions. Such CDR-grafted humanized antibodies are much less likely to give rise to a HAMA response than chimeric antibodies in view of the much lower proportion of non-human amino acid sequences that they contain.

Although humanized antibodies were less immunogenic than their natural or chimeric counterparts, many groups found that CDR grafted humanized antibodies demonstrated a significantly decreased binding affinity (e.g., Riechmann, et al. Nature 332:323-327 1988). For instance, Reichmann and colleagues found that transfer of the CDR regions alone was not sufficient to provide satisfactory antigen binding activity in the CDR-grafted product, and it was also necessary to convert a serine residue at position 27 of the human sequence to the corresponding rat phenylalanine residue. These results indicated that changes to residues of the human sequence outside the CDR regions, in particular in the loop adjacent to CDR1, may be necessary to obtain effective antigen binding activity. Even so, the binding affinity was still significantly less than that of the original monoclonal antibody.

More recently, Queen et al (U.S. Pat. No. 5,530,101, herein incorporated by reference) described the preparation of a humanized antibody that binds to the interleukin 2 receptor, by combining the CDRs of a murine MAb (anti-Tac) with human immunoglobulin framework and constant regions. The human framework regions were chosen to maximize homology with the anti-Tac MAb sequence. In addition computer modeling was used to identify framework amino acid residues which were likely to interact with the CDRs or antigen, and mouse amino acids were used at these positions in the humanized antibody. The humanized anti-Tac antibody obtained was reported to have an affinity for p55 of $3 \times 10^9$ M$^{-1}$, which was still only about one-third of that of the murine MAb.

Other groups identified further positions within the framework of the variable regions (i.e. outside the CDRs and structural loops of the variable regions) at which the amino acid identities of the residues may contribute to obtaining CDR-grafted products with satisfactory binding affinity. See, e.g., U.S. Pat. Nos. 6,054,297 and 5,929,212, herein incorporated by reference. Still, it is impossible to know before-hand how effective a particular CDR grafting arrangement will be for any given antibody of interest.

Recently, it was shown that interleukin-9 (IL-9) plays a critical role in a number of antigen-induced responses in mice including bronchial hyperresponsiveness, epithelial mucin production, eosinophilia and elevated inflammatory cell counts in bronchial lavage, including T cells, B cells, mast cells, neutrophils and eosinophils and elevated serum total IgE, typifying the allergic inflammation associated with asthma. See Levitt et al., U.S. Pat. No. 6,261,559, herein incorporated by reference. Structural similarity has been observed for the human and murine IL-9 genes, suggesting that human IL-9 would be expected to play a similar role in the indication of asthmatic immune responses. IL-9 is expressed by activated T cells and mast cells, with the protein serving as a T cell growth factor and a cytokine that mediates the growth of erythroid progenitors, B cells, eosinophils mast cells, and promoting the production of mucin by lung epithelium.

Levitt and colleagues demonstrated that pretreatment of mice with polyclonal neutralizing antibodies to murine IL-9 resulted in the complete protection of mice from antigen challenge in a mouse asthma model. It would be useful for human patients suffering from diseases or conditions associated with IL-9 expression such as asthma if antibodies having a low immunogenicity and a high binding affinity for human IL-9 could be designed for use in human therapy. The present invention provides for such antibodies, and their use in treating conditions wherein modulation and/or inhibition of IL-9 activity is therapeutically beneficial, e.g., allergic conditions such as bronchial hyperresponsivness, and atopic allergy including asthma.

SUMMARY OF THE INVENTION

The present invention provides recombinant antibody molecules comprising antigen binding regions derived from the heavy and/or light chain variable regions of a donor anti-human IL-9 antibody and having anti-IL-9 binding specificity associated with inhibition of IL-9-mediated immune cell responses. As discussed in detail infra, the donor anti-human IL-9 antibody comprises one of three rodent monoclonal antibodies (Mabs), referred to herein as MH9A3, MH9D1, or MH9L1, which are murine anti-human IL-9 monoclonal antibodies. Recombinant antibodies or fragments derived therefrom according to the invention will comprise only the variable region (VH and/or VL) or one or more CDRs or other important binding residues of such a Mab or variable regions have substantial sequence identity herewith as disclosed infra. The invention encompasses in particular both chimeric and humanized (e.g., CDR-grafted) anti-human IL-9 antibodies derived from MH9A3, MH9D1, and MH9L1. The antibodies of the present invention are preferably isolated using a rational design approach based on homology alignment, or by successive panning of a phage display framework library.

The present invention also includes methods for identifying neutralizing epitopes of IL-9, e.g. using the anti-IL-9 antibodies identified herein, and the use of such epitopes to identify peptides that bind to IL-9 or to IL-9 receptor and which inhibit binding of IL-9 to its receptor. Such epitopes may be linear or conformational according to the methods described herein. The invention further contemplates neutralizing peptides designed from such epitopes.

The present invention also encompasses the use of the neutralizing antibodies and peptides of the present invention for inhibiting or preventing at least one IL-9 response in vitro, ex vivo or in vivo. In a preferred embodiment, the invention provides methods of treating patients suffering from asthmatic symptoms comprising administering to a patient an amount of a recombinant anti-human IL-9 antibody or neutralizing peptide according to the invention effective to reduce the disease symptoms. For example, when administered prior to or during an ongoing asthma attack, the antibodies and peptides of the invention should neutralize interleukin-9, down-regulate the activity of interleukin-9, reduce bronchial hyper-responsiveness in the patient, reduce mucin expression in lung epithelia, and/or reduce eosinophilia in the lungs of the patient. The invention also encompasses inhalation devices that may be used to deliver to a patient a therapeutically effective amount of the anti-human IL-9 antibodies and peptides described herein.

Antibodies of the invention include, but are not limited to, monoclonal, multispecific, human or chimeric antibodies, single chain antibodies, Fab fragments, F(ab') fragments, antiidiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA, and IgA1) or subclass of immunoglobulin molecule. Preferably, an antibody of the invention comprises, or alternatively consists of, a VH domain, VH CDR, VL domain, or VL CDR having an amino acid or a fragment or variant thereof.

An immunoglobulin light or heavy chain variable region consists of "framework" regions interrupted by three hypervariable regions, also called the complementary determining regions (CDR's). Both the heavy and light chain variable regions contain four framework region and three CDRs (see FIG. 14). The framework regions and CDR's have been precisely defined by E. Kabat ("Sequences of Proteins of Immunological Interest," E. Kabat et al., U.S. Department of Health and Human Services, (1983); which is incorporated herein by reference).

In order to more clearly describe the invention the following definitions are provided. Otherwise all terms herein should be convinced to have their ordinary meaning as construed by one having skill in the relevant art, in the synthesis of recombinant antibodies for clinical use.

An antibody of the invention "which binds IL-9" is one which detectably binds an IL-9, preferably human IL-9. Assays which measure binding to an IL-9 include, but are not limited to, receptor binding inhibition assay or capture of soluble IL-9 from solution. BIAcore and ELISA assays detect IL-9 bound to a solid support. Neutralizing assays measure loss of IL-9 induced proliferation in a responsive cell line.

The term "variant" as used herein refers to a polypeptide that possesses a similar or identical function as an IL-9 polypeptide, a fragment of IL-9, an anti-IL-9 antibody or antibody fragment thereof, but does not necessarily comprise a similar or identical amino acid sequence of an IL-9 polypeptide, a fragment of IL-9, an anti-IL-9 antibody or antibody fragment thereof, or possess a similar or identical structure of an IL-9 polypeptide, a fragment of IL-9, an anti-IL-9 antibody or antibody fragment thereof. A variant having a similar amino acid refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of an IL-9 polypeptide, a fragment of IL-9, an anti-IL-9 antibody or antibody fragment thereof (including a VH domain, VHCDR, VL domain or (b) a polypeptide encoded by a nucleotide sequence, the complementary sequence of which hybridizes under stringent conditions to a nucleotide sequence encoding an IL-9 polypeptide a fragment of IL-9, an anti-IL-9 antibody or antibody fragment thereof (including a VH domain, VHCDR, VL domain, or VLCDR of at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, identical to the nucleotide sequence encoding an IL-9 polypeptide, a fragment of IL-9, an anti-IL-9 antibody or antibody fragment thereof (including a VH domain, VHCDR, VL domain, or VLCDR described herein. A polypeptide with similar structure to an IL-9 polypeptide, a fragment of IL-9, an anti-IL-9 antibody or antibody fragment thereof, described herein refers to a polypeptide that has a similar secondary, tertiary or quaternary structure of an IL-9 polypeptide, a fragment of IL-9, an anti-IL-9 antibody, or antibody fragment thereof, described herein. The structure of a polypeptide can determine by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity number of identical overlapping positions/ total number of positions×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul Proc. Nad. Acad. Sci. USA 87:2264-2268 (1990), modified as in Karlin and Altschul Proc. NatL Acad. Sci. US, 4 90:5873-5877 (1993). The BLASTn and BLASTx programs of Altschul, et al. J. MoL BioL 215:403-410 (1990) have incorporated such an alogrithm. BLAST nucleotide searches can be performed with the BLASTn program, score=100, wordlength=12 to obtain nucleotide sequences homologous to a nucleic acid molecules of the invention. BLAST protein searches can be performed with the BLASTx program, score=50, wordlength=3 to obtain amino acid sequences homologous to a protein molecules of the invention. To obtain gapped alignments for comparison purposes, Gapped BLAST can be utilized as described in Altschul et al. Nucleic Acids Res. 25:3389-3402 (1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used. (See http://www.ncbi.nlm.nib.gov.)

Another example of a mathematical algorithm utilized for the comparison of sequences is the algorithm of Myers and Miller, CABIOS (1989). The ALIGN program (version 2.0) which is part of the GCG sequence alignment software package has incorporated such an alogrithm. Other algorithms for sequence analysis known in the art include ADVANCE and ADAM as described in Torellis and Robotti Comput. Appl. Biosci., 10:3-5 (1994); and FASTA described in Pearson and Lipman Proc. Nad. Acad. Sci. 85:2444-8 (1988). Within FASTA, ktup is a control option that sets the sensitivity and speed of the search.

The term "derivative" as used herein, refers to a variant polypeptide of the invention that comprises, or alternatively consists of, an amino acid sequence of an IL-9 polypeptide, a fragment of IL-9, or an antibody of the invention that immunospecifically binds to IL-9, which has been altered by the introduction of amino acid residue substitutions, deletions or additions. The term "derivative" as used herein also refers to an IL-9 polypeptide, a fragment of IL-9, an antibody that immunospecifically binds to IL-9 which has been modified, e.g., by the covalent attachment of any type of molecule to the polypeptide. For example, but not by way of limitation, an IL-9 polypeptide, a fragment of IL-9, or an anti-IL-9 antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of an IL-9 polypeptide, a fragment of IL-9, or an anti-IL-9 antibody, may be modified by chemical modifications using techniques known to those of skill in the art, including, but not limited to, specific chemical cleavage, acetylation, formylation, metabolic synthesis of tunicamycin, etc. Further, a derivative of an IL-9 polypeptide, a fragment of IL-9, or an anti-IL-9 antibody, may contain one or more non-classical amino acids. A polypeptide derivative possesses a similar or identical function as an IL-9 polypeptide, a fragment of IL-9, or an anti-IL-9 antibody, described herein.

The term "epitopes" as used herein refers to portions of IL-9 having antigenic or immunogenic activity in an animal, preferably a mammal. An epitope having immunogenic activity is a portion of IL-9 that elicits an antibody response in an animal. An epitope having antigenic activity is a portion of IL-9 to which an antibody immunospecifically binds as determined by any method known in the art, for example, by the immunoassays described herein. Antigenic epitopes need not necessarily be immunogenic.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid, residues, at least 30 amino acid residues, at least 35 amino acid residues, at least 40 amino acid residues, at least 45 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 130 amino acid residues, at least 135 amino acid residues, or at least 140 amino acid residues, of human IL-9 (see U.S. Pat. No. 6,261,559 for sequence of processed (126 amino acids) and unprocessed (144 amino acids) human IL-9)), which patent is incorporated by reference herein for the amino acid sequence of IL-9.

The term "fusion protein" as used herein refers to a polypeptide that comprises, or alternatively consists of, an amino acid sequence of an anti-IL-9 antibody of the invention or a fragment or variant thereof and another moiety, e.g., a polypeptide unrelated to an antibody or antibody domain.

The term "host cell" as used herein refers to a particular cell comprising a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

BRIEF DESCRIPTION OF FIGURES

FIG. 1 contains the cDNA sequence encoding the light chain of a chimeric antibody derived from MH9A3 (SEQ ID NO: 1).

FIG. 2 contains the cDNA sequence encoding the heavy chain of the chimeric antibody derived from MH9A3 (SEQ ID NO: 2).

FIG. 3 contains the amino acid sequences of the MH9A3, MH9L1, and MH9D1 chimeric heavy chain CDRs, respectively (SEQ ID NOs: 3, 128, and 4, respectively).

FIG. 4 contains the amino acid sequences of the MH9A3, MH9L1, and MH9D1 chimeric light chain CDRs, respectively (SEQ ID NOs: 5, 129, and 6, respectively).

FIG. 6 contains the sequences of antibody heavy chains VH1-69 and VH 5-51 (SEQ ID NOs: 7 & 8) obtained via rational design optimization of the MH9A3 chimeric antibody, as compared to native MH9A3 and the homologous human H1 (1-69) (SEQ ID NO: 13) and H2 (5-51) (SEQ ID NO: 14) sequences.

FIG. 7 contains the sequence of the antibody light chain B3 obtained via rational design optimization of the MH9A3 chimeric antibody, as compared to MH9A3; as shown in the alignment, it is essentially identical to the human L1 (B3) sequence (SEQ ID NO: 11).

FIG. 9 contains the sequence of the antibody light chain L1 obtained via rational design optimization of the MH9D1 chimeric antibody, derived from MH9D1 as compared to MH9D1; as shown in the alignment, it is essentially identical to the human L1 (L1) sequence (SEQ ID NO: 12).

FIG. 11 contains the amino acid sequences of light chains obtained by rational design optimization and fine-tuning of the MH9A3(B3) light chain (SEQ ID NOs 18-25).

FIG. 15 contains the sequences of light chains (SEQ ID NOs: 26-32) obtained after three rounds of panning for MH9A3 light chain.

FIG. 17 contains the amino acid sequences of the MH9L1 heavy chain aligned against the human heavy chain sequences VH1-69 and VH5-51.

FIG. 18 contains the MH9L1 light chain aligned against the human light chain sequences A26 and L15.

FIG. 20 contain sequences of the heavy and light chain variable regions for the humanized antibodies of MH9A3, MH9L1, and MH9D1 in human antibody framework regions.

DETAILED DESCRIPTION OF THE INVENTION

Figure 5:
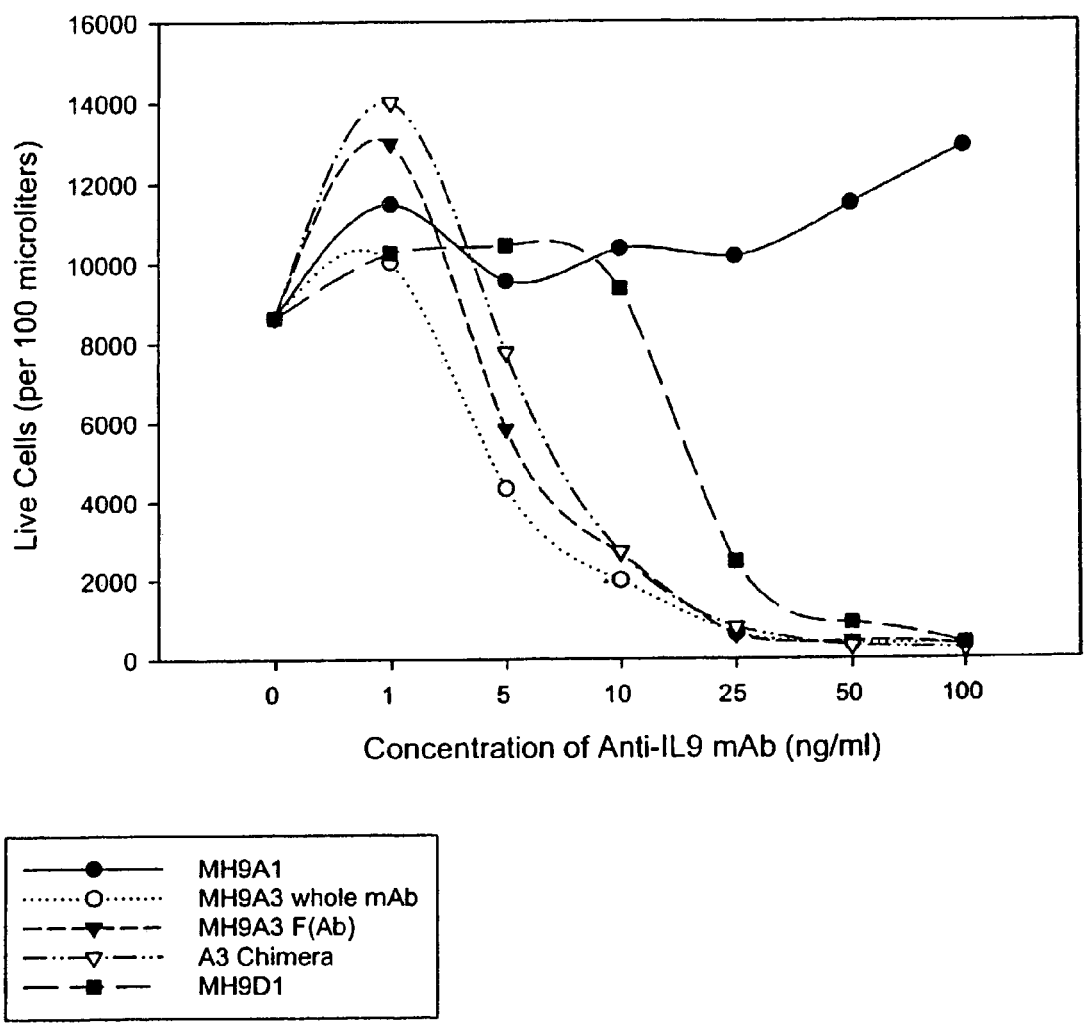
FIG. 5 contains the graph showing inhibition of TS1-RA3 proliferation by anti-IL-9 antibodies, including MH9A1 (—●—), MH9A3 whole (····○····), MH9A3 F(Ab) (--▼--), MH9A3 chimera (-·-∇-·-) and MH9D1 (- -■- -) antibodies.

The present invention encompasses antibodies (including molecules comprising, or alternatively consisting of, antibody fragments or variants thereof) that immunospecifically bind to IL-9 or a fragment or variant of IL-9. In particular, the invention provides recombinant antibodies, e.g., humanized, chimeric, and antibody fragment single chain Fvs (scFvs) derived from MH9A3, MH9D1, and MH9L1. In particular, the present invention encompasses antibodies that immunospecifically bind to a polypeptide, a polypeptide fragment or variant, or an epitope of human IL-9 or IL-9 expressed on human activated T cells or mast cells.

Antibodies of the present invention immunospecifically bind to polypeptides comprising or alternatively, consisting of, the amino acid sequence of native human IL-9 set forth below:

(SEQ ID NO: 124)
```
  1 mllamvltsa lllcsvagqg cptlagildi nflinkmqed paskchcsan vtsclclgip 61 sdnctrpcfs erlsqmtntt mqtryplifs rvkksvevlk nnkcpyfsce qpcnqttagn 121 altflkslle ifqkekmrgm rgki
``` or encoded by nucleic, acids which hybridize (e.g., under stringent hybridization conditions) to the genomic or cDNA nucleotide sequence encoding a human IL-9. Antibodies of the present invention also bind to fragments of the amino acid sequence of IL-9, or encoded by nucleic acids which hybridize (e.g., under stringent hybridization conditions) to the nucleotide sequence encoding human IL-9. This IL-9 sequence contains a signal sequence, which corresponds to the first 18 amino acids that is cleared on maturation. The cDNA sequence for human IL-9 is set forth below:

(SEQ ID NO: 125)
```
atgcttctgg ccatggtcct tacctctgcc ctgctcctgt gctccgtggc aggccagggg  60
tgtccaacct tggcggggat cctggacatc aacttcctca tcaacaagat gcaggaagat 120
ccagcttcca agtgccactg cagtgctaat gtgaccagtt gtctctgttt gggcattccc 180
tctgacaact gcaccagacc atgcttcagt gagagactgt ctcagatgac caataccacc 240
atgcaaacaa gatacccact gattttcagt cgggtgaaaa aatcagttga agtactaaag 300
aacaacaagt gtccatattt ttcctgtgaa cagccatgca accaaaccac ggcaggcaac 360
gcgctgacat ttctgaagag tcttctggaa aitticcaga agaaaagat gagagggatg 420 agaggcaaga tatga 435
```

Additionally, the amino acid and nucleic acid sequences for IL-9 receptor are set forth below:

(SEQ ID NO: 126)
```
MGLGRCIWEGWTLESEALRRDMGTWLLACICICTCVCLGVSVTGEGQGPRSRTFTCLTNNILRID

CHWSAPELGQGSSPWLLFTSNQAPGGTHKCILRGSECTVVLPPEAVLVPSDNFTITFHHCMSGRE

QVSLVDPEYLPRRHVKLDPPSDLQSNISSGHCILTWSISPALEPMTTLLSYELAFKKQEEAWEQA

QHRDHIVGVTWLILEAFELDPGFIHEARLRVQMATLEDDVVEEERYTGQWSEWSQPVCFQAPQRQ

GPLIPPWGWPGNTLVAVSIFLLLTGPTYLLFKLSPRVKRIFYQNVPSPAMFFQPLYSVHNGNFQT

WMGAHRAGVLLSQDCAGTPQGALEPCVQEATALLTCGPARPWKSVALEEEQEGPGTRLPGNLSSE

DVLPAGCTEWRVQTLAYLPQEDWAPTSLTRPAPPDSEGSRSSSSSSSSSNNNNYCALGCYGGWHL

SALPGNTQSSGPIPALACGLSCDHQGLETQQGVAWVLAGHCQRPGLHEDLQGMLLPSVLSKARSW

TF
```

(SEQ ID NO: 127)
```
  1     agcagctctg taatgcgctt gtggtttcag atgtgggcgg cctgtgtgaa cctgtcgtgc 61     aaagctcacg tcaccaactg ctgcagttat ctcctgaatc aggctgaggg tctttgctgt 121     gcacccagag atagttgggt gacaaatcac ctccaggttg gggatgcctc agacttgtga 181     tgggactggg cagatgcatc tgggaaggct ggaccttgga gagtgaggcc ctgaggcgag
```

-continued

```
241   acatgggcac ctggctcctg gcctgcatct gcatctgcac ctgtgtctgc ttgggagtct
301   ctgtcacagg ggaaggacaa gggccaaggt ctagaacctt cacctgcctc accaacaaca
361   ttctcaggat cgattgccac tggtctgccc cagagctggg acagggctcc agccctggc
421   tcctcttcac cagcaaccag gctcctggcg gcacacataa gtgcatcttg cggggcagtg
481   agtgcaccgt cgtgctgcca cctgaggcag tgctcgtgcc atctgacaat ttcaccatca
541   ctttccacca ctgcatgtct gggagggagc aggtcagcct ggtggacccg gagtacctgc
601   cccggagaca cgttaagctg gacccgccct ctgacttgca gagcaacatc agttctggcc
661   actgcatcct gacctggagc atcagtcctg ccttggagcc aatgaccaca cttctcagct
721   atgagctggc cttcaagaag caggaagagg cctgggagca ggcccagcac agggatcaca
781   ttgtcggggt gacctggctt atacttgaag cctttgagct ggacccctggc tttatccatg
841   aggccaggct gcgtgtccag atggccacac tggaggatga tgtggtagag gaggagcgtt
901   atacaggcca gtggagtgag tggagccagc ctgtgtgctt ccaggctccc cagagacaag
961   gccctctgat cccaccctgg gggtggccag gcaacaccct tgttgctgtg tccatctttc
1021  tcctgctgac tggcccgacc tacctcctgt tcaagctgtc gcccagggtg aagagaatct
1081  tctaccagaa cgtgccctct ccagcgatgt tcttccagcc cctctacagt gtacacaatg
1141  ggaacttcca gacttggatg ggggcccaca gggccggtgt gctgttgagc caggactgtg
1201  ctggcacccc acagggagcc ttggagccct gcgtccagga ggccactgca ctgctcactt
1261  gtggcccagc gcgtccttgg aaatctgtgg ccctggagga ggaacaggag ggccctggga
1321  ccaggctccc ggggaacctg agctcagagg atgtgctgcc agcagggtgt acggagtgga
1381  gggtacagac gcttgcctat ctgccacagg aggactgggc ccccacgtcc ctgactaggc
1441  cggctccccc agactcagag ggcagcagga gcagcagcag cagcagcagc agcagcaaca
1501  acaacaacta ctgtgccttg ggctgctatg ggggatggca cctctcagcc ctcccaggaa
1561  acacacagag ctctgggccc atcccagccc tggcctgtgg cctttcttgt gaccatcagg
1621  gcctggagac ccagcaagga gttgcctggg tgctggctgg tcactgccag aggcctgggc
1681  tgcatgagga cctccagggc atgttgctcc cttctgtcct cagcaaggct cggtcctgga
1741  cattctaggt ccctgactcg ccagatgcat catgtccatt tgggaaaat ggactgaagt
1801  ttctggagcc cttgtctgag actgaacctc ctgagaaggg gcccctagca gcggtcagag
1861  gtcctgtctg gatggaggct ggaggctccc ccctcaaccc ctctgctcag tgcctgtggg
1921  gagcagcctc taccctcagc atcctgg
```

Polypeptide fragments may be "free-standing," or comprised within a larger polypeptide of which the fragment forms a part or region, most preferably as a single continuous region. Representative examples of polypeptide fragments that may be bound by antibodies of the present invention, include, for example, fragments that comprise or alternatively, consist of from about amino acid residues: 1 to 15, 16-30, 31-46, 47-55, 56-72, 73-104, 105-126 the of the amino acid sequence corresponding to human IL-9 and fragments thereof. Moreover, polypeptide fragments of IL-9 that may be bound by antibodies of the present invention, can be at least 10, 20, 30, 40, 50, 60, 70, 80, 90, 100, 110 or 120 or 125 amino acids in length. In this context, "about" means the particularly recited ranges and ranges larger or smaller by several, a few, 5, 4, 3, 2 or 1 amino acid residues at either or both the amino- and carboxy-termini.

In another embodiment, the invention provides antibodies that bind a polypeptide comprising, or alternatively consisting of, an epitope-bearing portion of a polypeptide of the invention. The epitope of this polypeptide portion may be an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998-4002 (1983).

As to the selection of polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins", Scielwe, 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., Cell 37:767-778 (1984) at 777.

In specific embodiments, antibodies of the present invention bind antigenic epitope-bearing peptides and polypeptides of IL-9 and preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids contained within the amino acid sequence of an IL-9 polypeptide. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length.

IL-9 epitope-bearing peptides and polypeptides may be produced by any conventional means. See, e.g., Houghten, R. A. (1985) General method for the rapid solid-phase synthesis of large numbers of peptides: specificity of antigen-antibody interaction at the level of individual amino acids. Proc. Natl. Acad. Sci. USA 82:5131-5135; this "Simultaneous Multiple. Peptide Synthesis (SMPS)" process is further described in U.S. Pat. No. 4,631,211 to Houghten et al. (1986).

The present invention encompasses antibodies that bind polypeptides comprising, or alternatively consisting of, an epitope of the polypeptide having an amino acid sequence of IL-9, or an epitope of the polypeptide sequence encoded by a polynucleotide sequence encoding an IL-9 polypeptide or encoded by a polynucleotide that hybridizes to a cDNA sequence encoding IL-9.

The present invention also encompasses antibodies that bind polypeptides comprising, or alternatively consisting of, an epitope of an IL-9 polypeptide.

The term "epitopes," as used herein, refers to portions of a polypeptide having antigenic or immunogenic activity in an animal, preferably a mammal, and most preferably in a human. In a preferred embodiment, the present invention encompasses antibodies that bind a polypeptide comprising an epitope. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

IL-9 polypeptide fragments which function as epitopes may be produced by any conventional means. (See, e.g., Houghten, Proc. Natl. Acad. Sci. USA 82: 5131-5135 (1985), further described in U.S. patent Ser. No. 41/631, 211).

In the present invention, antibodies of the present invention bind antigenic epitopes preferably containing a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes that may be bound by antibodies of the present invention are at least 10, 15, 20, 25, 30, 35, 40, 45, 50, 55, 60, 65, 70, 75, 80, 85, 90, 95, 100, 105, 110, 115, 120 or 125 or amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically, bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985)). Preferred immunogenic epitopes include the immunogenic epitopes disclosed herein, as well as any combination of two, three, four, five or more of these immunogenic epitopes. The polypeptides comprising one or more immunogenic epitopes of IL-9 may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing IL-9 polypeptides may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, antipeptide antibody titer may be boosted by coupling the peptide to a macromolecular carrier, such as keyhole limpet hemocyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intravenous intradermal of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a, solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the antibodies of the present invention may bind polypeptides comprising an immunogenic or antigenic epitope fused to other polypeptide sequences. For example, an IL-9 polypeptide may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. Such fusion proteins may facilitate purification and may increase half-life in vivo. This has been shown for chimeric proteins consisting of the first two domains of the human CD4 polypeptide and various domains of the constant regions of the heavy or light chains of mammalian immunoglobulins. See, e.g., EP 394,827; Traunecker et al., Nature, 331:84 86 (1998). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by-Janknecht et al. allows for the ready purification of non-denatured fusion proteins expressed in human cell lines (Janknecht et al., 1991, Proc. Natl. Acad. Sci. USA 88:8972-897). In this system, the gene of interest is sub-cloned into a vaccinia recombination plasmid such that the open reading frame of the gene is transitionally fused to an amino-terminal tag consisting of six histidine residues. The tag serves as a matrix-binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

In another embodiment, the antibodies of the present invention bind IL-9 polypeptides and/or the epitope-bearing fragments thereof that are fused with a heterologous antigen (e.g., polypeptide, carbohydrate, phospholipid, or nucleic acid). In specific embodiments, the heterologous antigen is an immunogen.

In another embodiment, antibodies of the present invention bind mutant IL-9 polypeptides that have been generated by random mutagenesis of a polynucleotide encoding the IL-9 polypeptide, by error-prone PCR, random nucleotide insertion or other methods prior to recombination. In another embodiment, antibodies of the present invention bind one or more components, motifs, sections, parts, domains, fragments, etc., of IL-9 recombed with one or more components, motifs, sections, parts, domains, fragments, etc. of one or more heterologous molecules.

In another embodiment, antibodies of the present invention bind previously known variant IL-9 polypeptides described, for example, in PCT Publication No. WO98/24904.

To improve or alter the characteristics of IL-9 polypeptides, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. For instance, for many proteins, it is known in the art that one or more amino acids may be deleted from the N-terminus or C-terminus without substantial loss of biological function. For instance, Ron et al., J. Biol. Chem., 268:2984-2988 (1993) reported modified KGF proteins that had heparin binding activity even if 3, 8, or 27 amino-terminal amino acid residues were missing. Accordingly, antibodies of the present invention may bind IL-9 polypeptide mutants or variants generated by protein engineering.

Accordingly, the present invention further provides antibodies that bind polypeptides having one or more residues deleted from the amino terminus of the amino acid sequence of human IL-9. In particular, the present invention provides antibodies that bind polypeptides comprising, or alternatively consisting of, the amino acid sequence of n'-126 or human IL-9 where n' is an integer in the range of the amino acid position of amino acid residues 2-125 of the amino acid sequence in human IL-9. More in particular, the invention provides antibodies that bind polypeptides comprising, or alternatively consisting of, an amino acid sequence selected from the group consisting of residues 2-126, 3-126, 4-126, 5-126, 6-126, 7-126, 8-126, 9-126, 50-126, 51-126, 52-126, . . . 75-126, 76-126, 77-126, . . . , 100-126, 101-126, 102-126, . . . and 110-126. The present invention is also directed to antibodies that bind IL-9 polypeptides comprising, or alternatively, consisting of, a contiguous sequence of amino acid residues at least 80%, 85%, 90%, 92%, 95%, 96%, 97%, 98% or 99% identical to the amino acid sequence of IL-9 polypeptides described above.

Accordingly, the present invention further provides antibodies that bind polypeptides having one or more residues deleted from the amino terminus of the amino acid sequence of IL-9. The present invention is also directed to antibodies that bind IL-9 polypeptides comprising, or alternatively, consisting of, a contiguous sequence of amino acid residues at least 80%, 85%, 90%, 92%, 95%, 96%, 97%, 98% or 99% identical to the amino acid sequence of an IL-9 polypeptide or fragment thereof.

Highly preferred embodiments of the invention are directed to antibodies that bind polypeptides comprising, or alternatively consisting of, a polypeptide having an amino acid sequence least 80%, 85%, 90% identical and more preferably at least 95%, 96%, 97%, 98%, 99% or 100% identical to native forms of human IL-9 polypeptide.

Preferred embodiments of the invention are directed to antibodies that bind polypeptides comprising, or alternatively consisting of, a polypeptide having an amino acid sequences at least 90% identical to an IL-9 polypeptide having the amino acid sequence of human IL-9. More preferred embodiments of the invention are directed to antibodies that bind polypeptides comprising, or alternatively consisting of, a polypeptide having an amino acid sequences at least 95% identical to an IL-9 polypeptide having the amino acid sequence of a native human IL-9. More preferred embodiments of the invention are directed to antibodies that bind polypeptides comprising, or alternatively consisting of, a polypeptide having an amino acid sequences at least 96% identical to an IL-9 polypeptide having the amino acid sequence of native human IL-9.

Additionally, more preferred embodiments of the invention are directed to antibodies that bind polypeptides comprising, or alternatively consisting of, a polypeptide having an amino acid sequence at least 97% to an IL-9 polypeptide having the amino acid sequences of a native human IL-9. Additionally, more preferred embodiments of the invention are directed to antibodies that bind polypeptides comprising, or alternatively consisting of, a polypeptide having an amino acid sequence at least 98% to an IL-9 polypeptide having the amino acid sequences of a native human IL-9. Additionally, more preferred embodiments of the invention are directed to antibodies that bind polypeptides comprising, or alternatively consisting of, a polypeptide having an amino acid sequence at least 99% identical to IL-9 polypeptide having the amino acid sequence of native human IL-9.

Similarly, many examples of biologically functional C-terminal deletion polypeptides are known. For instance, Interferon gamma shows up to ten times higher activities by deleting 8-10 amino acid residues from the carboxy terminus of the protein (Dobeli et al., J Biotechnology 7:199-216 (1988). However, even if deletion of one or more amino acids from the C-terminus of a protein results in modification or loss of one or more biological functions of the protein, other functional activities may still be retained. Thus, the ability of the shortened protein to induce and/or bind to antibodies which recognize the complete or mature protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides antibodies that bind polypeptides having one or more residues deleted from the carboxy terminus of the amino acid sequence of the IL-9 polypeptide. In particular, the present invention provides antibodies that bind polypeptides comprising, or alternatively consisting of, the amino acid sequence of residues 1-n of the amino acid sequence of human IL-9, where n is any integer in the range of the amino acid position of amino acid residues 30-125 of human IL-9.

Also provided are antibodies that bind IL-9 polypeptides comprising, or alternatively consisting of, IL-9 polypeptides with one or more amino acids deleted from both the amino and the carboxyl termini, which may be described generally as having residues $n^1$-$m^1$ of human IL-9, where ni and mi are integers as defined above.

However, even if deletion of one or more amino acids from the C-terminus of a polypeptide results in modification or loss of one or more biological functions of the polypeptide, other functional activities may still be retained. Thus, the ability of the shortened polypeptide to induce and/or bind to antibodies which recognize the complete, mature or extracellular forms of the polypeptide generally will be retained when less than the majority of the residues of the complete, mature or extracellular forms of the polypeptide are removed from the C-terminus. Whether a particular polypeptide lacking C-terminal residues of the predicted extracellular domain retains such immunologic activities can readily be determined by routine methods described herein and otherwise known in the art.

Also as mentioned above, even if deletion of one or more amino acids from the C-terminus of a protein results in modification or loss of one or more functional activities (e.g., biological activity) of the protein, other functional activities may still be retained. Thus, the ability of a shortened IL-9 mutein to induce and/or bind to antibodies which recognize the complete or mature form or the extracellular domain of the polypeptide generally will be retained when less than the majority of the residues of the complete or mature form or the extracellular domain of the polypeptide are removed from the C-terminus. Whether a particular polypeptide lacking C-terminal residues of a complete polypeptide retains such immunologic activities can readily be determined by routine methods described herein and otherwise known in the art. It is not unlikely that an IL-9 mutein with a large number of deleted C-terminal amino acid residues may retain some functional (e.g., biologic or immunogenic) activities.

Accordingly, the present invention further provides in another embodiment, antibodies that bind polypeptides having one or more residues deleted from the carboxy terminus of the amino acid sequence of the IL-9.

The invention also provides antibodies that bind polypeptides having one or more amino acids deleted from both the amino and the carboxyl termini of an IL-9 polypeptide.

Antibodies of the present invention may bind fragments, derivatives or analogs of human IL-9 polypeptide such as (i) polypeptides in which one or more of the amino acid residues are substituted with a conserved or non-conserved amino acid residue (preferably a conserved amino acid residue) and such substituted amino acid residue may or may not be one encoded by the genetic code, or (ii) polypeptides in which one or more of the amino acid residues includes a substituent group, or (iii) polypeptides in which the extracellular domain of the polypeptide is fused with another compound, such as a compound to increase the half-life of the polypeptide (for example, polyethylene glycol), or (iv) polypeptides in which the additional amino acids are fused to the extracellular domain of another polypeptide, an IgG Fc fusion region peptide or leader or secretory sequence or a sequence which is employed for purification of the extracellular domain of the polypeptide or a pro-protein sequence. Such fragments, derivatives and analogs are deemed to be within the scope of those skilled in the art from the teachings herein.

Thus, the antibodies of the invention may bind IL-9 polypeptides that include one or more amino acid substitutions, deletions or additions, either from natural mutations or human manipulation. As indicated, changes are preferably of aminor nature, such as conservative amino acid substitutions that do not significantly affect the folding or activity of the protein.

In one embodiment of the invention, antibodies of the present invention bind polypeptides comprising, or alternatively consisting of, the amino acid sequence of an IL-9 polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. In one embodiment of the invention, antibodies of the present invention bind polypeptides comprising, or alternatively consisting of, the amino acid sequence of an IL-9 polypeptide having an amino acid sequence which contains at least one conservative amino acid substitution; but not more than 10, 9, 8, 7, 6, 5, 4, 3, 2 or 1 conservative amino acid substitutions.

For example, site directed changes at the amino acid level of IL-9 can be made by replacing a particular amino acid with a conservative substitution. Antibodies of the present invention may bind IL-9 amino acid sequences containing conservative substitution mutations of the polypeptide of a native human IL-9.

In another embodiment, site directed changes at the amino acid level of IL-9 can be made by replacing a particular amino acid with a conservative substitution. Antibodies of the present invention may bind IL-9 amino acid sequences containing conservative substitution mutations of the IL-9 polypeptide.

In another embodiment, site directed changes at the amino acid level of IL-9 can be made by replacing a particular amino acid with a conservative substitution. Antibodies of the present invention may bind IL-9 amino acid sequences containing conservative substitution mutations.

Amino acids in the IL-9 polypeptides that are essential for function can be identified by methods known in the art, such as site-directed mutagenesis or alanine-scanning mutagenesis (Cunningham and Wells, Science 244:1081-1085 (1989)). The latter procedure introduces single alanine mutations at every residue in the molecule. The resulting mutant molecules are then tested for functional activity, such ligand binding and the ability to stimulate lymphocyte (e.g., B cell) as, for example, proliferation, differentiation, and/or activation. Accordingly, antibodies of the present invention may bind amino acids in the IL-9 polypeptides that are essential for function. In preferred embodiments, antibodies of the present invention bind amino acids in the IL-9 polypeptides that are essential for function and inhibit IL-9 polypeptide function. In other preferred embodiments, antibodies of the present invention bind amino acids in the IL-9 polypeptides that are essential for function and enhance IL-9 polypeptide function.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al, Clin. Exp. Immunol. 2:331-340 (1967); Robbins et al., Diabetes 3 6: 838-845 (1987); Cleland et al., Crit. Rev. Therapeutic Drug Carrier Systems 10:307-377 (1993).

In another embodiment, the invention provides for antibodies that bind polypeptides having amino acid sequences containing non-conservative substitutions of the human IL-9 amino acid sequence.

In an additional embodiment, antibodies of the present invention bind IL-9 polypeptides comprising, or alternatively consisting of, an IL-9 amino acid sequence in which more than one amino acid (e.g., 2, 3, 4, 5, 6, 7, 8, 9, 10, 15, 20, 30 and 50) is replaced with a substituted amino acids as described above (either conservative or non-conservative).

In another embodiment, site directed changes at the amino acid level of IL-9 can be made by replacing a particular amino acid with a non-conservative substitution. Antibodies of the present invention may bind IL-9 amino acid sequences containing non-conservative substitution mutations.

In an additional embodiment, antibodies of the present invention bind IL-9 polypeptides comprising, or alternatively consisting of, an IL-9 amino acid sequence in which more than one amino acid (e.g., 2, 3, 4, 5, 6, 7, 8, 9, 10, 15, 20, 30 and 50) is replaced with the substituted amino acids as described above (either conservative or non-conservative).

Recombinant DNA technology known to those skilled in the art (see, for instance, DNA shuffling supra) can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than 103 the corresponding natural polypeptide, at least under certain purification and storage conditions.

Thus, the invention also encompasses antibodies that bind IL-9 derivatives and analogs that have one or more amino acid residues deleted, added, or substituted to generate IL-9 polypeptides, e.g., that are better suited for expression, scale up, etc., in the host cells. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the IL-9 polypeptides of the invention, and/or an amino acid deletion at the second position of any one or more such recognition sequences will prevent glycosylation of the IL-9 at the modified tripeptide sequence (see, e.g., Miyajimo et al., EMBO J 5(6):1193-1197).

Further antibodies of the present invention bind polypeptides including polypeptides at least 80%, or at least 85% identical, more preferably at least 90% or 95% identical, still more preferably at least 96%, 97%, 98% or 99% identical to a native human IL-9 polypeptide and also include antibodies that bind portions of said native human IL-9 polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for. determining similarity. Bestfit uses the local homology algorithm of Smith and Waterman (Advances in Applied Mathematics 2:482-489, 1981) to find the best segment of similarity between two sequences.

By a polypeptide having an amino acid sequence at least, for example, 95% "identical" to a reference amino acid sequence of an IL-9 polypeptide is intended that the amino acid sequence of the polypeptide is identical to the reference sequence except that the polypeptide sequence may include up to five amino acid alterations per each 100 amino acids of the reference amino acid of the IL-9 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence of human IL-9, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix—PAM 0, k-tuple=2, Mismatch Penalty=1, Joining Penalty=20, Randomization Group Length=O, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100-residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90-residue subject sequence is compared with a 100-residue query sequence. This time the deletions are internal deletions so there are no residues at the N- or C-termini of the subject sequence, which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

The present invention also encompasses antibodies (including molecules comprising, or alternatively consisting of, antibody fragments or variants thereof) that immunospecifically bind to IL-9 polypeptides, which antibodies comprise, or alternatively consist of, all or a portion of a heavy and/or light chain variable domain of the MH9A3, MH9D1, or MH9L1.

The present invention also encompasses methods and compositions for detecting, diagnosing and/or prognosing diseases or disorders associated with aberrant or enhanced IL-9 expression or inappropriate IL-9 receptor function in an animal, preferably a mammal, and most preferably a human, comprising using antibodies (including molecules which comprise, or alternatively consist of, antibody fragments or variants thereof) that immunospecifically bind to IL-9. Diseases and disorders which can be detected, diagnosed or prognosed with the antibodies of the invention include, but are not limited to, allergic disorders such as asthma. Also the invention embraces the treatment of conditions wherein overproduction of mucin is involved in disease pathology, i.e., by lung tissue. Examples include cystic fibrosis, emphysema and COPD.

The present invention encompasses methods and compositions for preventing, treating or ameliorating diseases or disorders associated with aberrant or enhanced IL-9 or IL-9 receptor, expression or inappropriate IL-9 or IL-9 receptor function in an animal, preferably a mammal, and most preferably a human, comprising administering to said animal an effective amount of one or more antibodies (including molecules which comprise, or alternatively consist of, antibody fragments or variants thereof) that immunospecifically bind to IL-9 according to herewith. Diseases and disorders which can be prevented, treated or inhibited by administering an effective amount of one or more antibodies or molecules of the invention include, but are not limited to, autoimmune disorders (e.g., lupus, rheumatoid arthritis, multiple sclerosis, myasthenia gravis, Hashimoto's disease, and immunodeficiency syndrome), inflammatory disorders (e.g., asthma, allergic disorders, and rheumatoid arthritis), infectious diseases (e.g., AIDS), and proliferative disorders (e.g., leukemia, carcinoma, and lymphoma). In the preferred embodiment, the subject antibodies will be used to treat asthma. In another preferred embodiment the subject antibodies will be used to treat diseases involving mucin production as a major component of pathology. Such diseases include cystic fibrosis, emphysema and COPD by way of example.

The antibodies of the present invention can be produced using phage display technology. Single chain antibody molecules ("scFvs") displayed on the surface of phage particles are screened to identify those scFvs that immunospecifically bind to IL-9, including the membrane-bound form and soluble form of IL-9.

The present invention provides antibodies (including molecules comprising, or alternatively consisting of, antibody fragments or variants thereof) that immunospecifically bind to a polypeptide or a polypeptide fragment of IL-9. In particular, the invention provides antibodies derived from the variable domains of MH9A3, MH9D1, and MH9L1. The antibody sequences of these antibodies are contained in FIGS. 1 and 2 (light and heavy of MH9A3) and FIG. 3 (heavy and light of MH9D1 and MH9L1). Such variable domains may routinely be "converted" to immunoglobulin molecules by inserting, for example, the nucleotide sequences encoding the VH and/or VL domains of these antibodies into an expression vector containing the constant domain sequences and engineered to direct the expression of the immunoglobulin molecule.

In one embodiment, the invention provides antibodies (including molecules comprising, or alternatively consisting of, antibody fragments or variants thereof) wherein said antibodies comprise, or alternatively consist of, a polypeptide having an amino acid sequence of any one of the VH domains of MH9A3, MH9D1, or MH9L1. The present invention also provides antibodies that immunospecifically bind to a polypeptide, or polypeptide fragment of human IL-9, wherein said antibodies comprise, or alternatively consist of, a polypeptide having an amino acid sequence of any one, two, three, or more of the VH CDRs of MH9A3, MH9D1, or MH9L1. Molecules comprising, or alternatively consisting of, these antibodies, or antibody fragments or variants thereof, that immunospecifically bind to IL-9 or an IL-9 fragment are also encompassed by the invention, as are nucleic acid molecules encoding these antibodies, molecules, fragments and/or variants.

In one embodiment of the present invention, antibodies (including molecules comprising, or alternatively consisting of, antibody fragments or variants thereof) that immunospecifically bind IL-9, comprise, or alternatively consist of, a polypeptide having the amino acid sequence of a VH CDR of MH9A3, MH9D1, or MH9L1. In a preferred embodiment, antibodies that immunospecifically bind IL-9, comprise, or alternatively consist of a polypeptide having the amino acid sequence of a VH CDR3 contained in MH9A3, MH9D1, or MH9L1. In yet another embodiment, antibodies that immunospecifically bind IL-9, comprise, or alternatively consist of, a polypeptide having the amino acid sequence of a VH CDR1 contained in MH9A3, MH9D1, or MH9L1; a VH CDR2 contained in MH9A3, MH9D1, or MH9L1 and/or a VH CDR3 contained in MH9A3, MH9D1, or MH9L1. Preferably, antibodies of the invention comprise, or alternatively consist of, VH CDRs that are derived from the same variable domains. Molecules comprising, or alternatively consisting of, fragments or variants of these antibodies that immunospecifically bind to IL-9 are also encompassed by the invention, as are nucleic acid molecules encoding these antibodies, molecules, fragments or variants.

The present invention provides antibodies (including molecules comprising, or alternatively consisting of, antibody fragments or variants) that immunospecifically bind to a polypeptide, or polypeptide fragment of IL-9. In particular, the invention provides antibodies wherein said antibodies comprise, or alternatively consist of, a VL domain having an amino acid sequence of a VL domain of MH9A3, MH9D1, or MH9L1. The present invention also provides antibodies that immunospecifically bind to a polypeptide or polypeptide fragment of IL-9, wherein said antibodies comprise, or alternatively consist of, a VL CDR having an amino acid sequence of any one, two, three, or more of the VL CDRs contained in the MH9A3, MH9D1, or MH9L1 sequences. Molecules comprising, or alternatively consisting of, fragments or variants of these antibodies that immunospecifically bind to IL-9 are also encompassed by the invention, as are nucleic acid molecules encoding these antibodies, molecules, fragments or variants.

In one embodiment of the present invention, antibodies (including molecules comprising, or alternatively consisting of, antibody fragments or variants thereof) that immunospecifically bind IL-9, comprise, or alternatively consist of, a polypeptide having the amino acid sequence of a VL CDR of MH9A3, MH9D1, or MH9L1. In particular, the invention provides antibodies that immunospecifically bind IL-9, comprising, or, alternatively consisting of, a polypeptide having the amino acid sequence of a VL CDRI contained in MH9A3, MH9D1. or MH9L1. In another embodiment, antibodies that immunospecifically bind IL-9 comprise, or alternatively consist of, a polypeptide having the amino acid sequence of a VL CDR2 contained in MH9A3, MH9D1, or MH9L1. In a preferred embodiment, antibodies comprise, or alternatively consist of, a polypeptide having the amino acid sequence of a VL CDR3 contained in MH9A3, MH9D1, or MH9L1. In yet another embodiment, antibodies that immunospecifically bind IL-9 comprise, or alternatively consist of a polypeptide having the amino acid sequence of a VL CDRI contained in MH9A3, MH9D1, or MH9L1; a VL CDR2 of MH9A3, MH9D1, or MH9L1; and a VL CDR3 contained MH9A3, MH9D1, or MH9L1. Preferably, antibodies of the invention comprise, or alternatively consist of, VL CDRs that are derived from the same variable domains of MH9A3, MH9D1, or MH9L1. Molecules comprising, or alternatively consisting of, fragments or variants of these antibodies, that immunospecifically bind to IL-9 are also encompassed by the invention, as are nucleic acid molecules encoding these antibodies, molecules, fragments or variants.

The present invention also provides antibodies (including molecules comprising, or alternatively consisting of, antibody fragments or variants thereof) that immunospecifically bind to a polypeptide or a polypeptide fragment of IL-9, wherein said antibodies comprise, or alternatively consist of, a VH domain of one of the variable domains MH9A3, MH9D1, or MH9L1 combined with a VL domain of one of the variable domains of MH9A3, MH9D1, or MH9L1, or other VL domain. The present invention further provides antibodies that immunospecifically bind to a polypeptide or a polypeptide fragment of IL-9, wherein said antibodies comprise, or alternatively consist of, a VL domain of one of the variable domains disclosed infra combined with a VH domain of one of the scFvs disclosed infra, or other VH domain. In a preferred embodiment, antibodies that immunospecifically bind to a polypeptide or a polypeptide fragment of IL-9, comprise, or alternatively consist of, a polypeptide having the amino acid sequence of a VH domain of MH9A3, MH9D1, or MH9L1 and a VL domain of MH9A3, MH9D1, or MH9L1. In a further preferred embodiment, the antibodies of the invention comprise, or alternatively consist of, a VH and a VL domain from the same variable domain. Molecules comprising, or alternatively consisting of, fragments or variants of these antibodies, that immunospecifically bind to IL-9 are also encompassed by the invention, as are nucleic acid molecules encoding these antibodies, molecules, fragments or variants.

The present invention also provides antibodies (including molecules comprising, or alternatively consisting of, antibody fragments or variants) that immunospecifically bind to a polypeptide or polypeptide fragment of IL-9, wherein said antibodies comprise, or alternatively consist of, one, two, three, or more VH CDRs and one, two, three or more VL CDRs, of MH9A3, MH9D1, or MH9L1. In particular, the invention provides for antibodies that immunospecifically bind to a polypeptide or polypeptide fragment of IL-9, wherein said antibodies comprise, or alternatively consist of, a VH CDRI and a VL CDR1, a VH CDRI and a VL CDR2, a VH CDRI and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs of MH9A3, MH9D1, or MH9L1. In a preferred embodiment, one or more of these combinations are from the same variable domain. Molecules comprising, or alternatively consisting of, fragments or variants of these antibodies, that immunospecifically bind to IL-9 are also encompassed by the invention, as are nucleic acid molecules encoding these antibodies, molecules, fragments or variants.

The term "antibody," as used herein, refers to immunoglobulin molecules and immunologically active portions of immunoglobulin molecules, i.e., molecules that contain an antigen binding site that immunospecifically binds an antigen. As such, the term "antibody" encompasses not only whole antibody molecules, but also antibody fragments, as well as variants (including derivatives) of antibodies and antibody fragments. Antibodies of the invention include, but are not limited to, monoclonal, multispecific, human or chimeric antibodies, single chain antibodies, single chain Fvs (scFvs), Fab fragments, F(ab')2 fragments, Fd fragments, disulfide-linked Fvs (sdFvs), antiidiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Preferably, an antibody of the invention comprises, or alternatively consists of, a polypeptide having an amino acid sequence of a VH domain, VH CDR, VL domain, or VL CDR of the MH9A3, MH9D1, and MH9L1 antibody sequences disclosed infra. Antibodies of the invention also include molecules comprising, or alternatively consisting of, fragments or variants of the above antibodies that immunospecifically bind IL-9.

Most preferably the antibodies of the present invention are whole antibodies or antibody fragments that immunospecifically bind human IL-9. Antibody fragments of the invention that immunospecifically bind human IL-9 include, but are not limited to, Fab, Fab' and F(ab')2, Fd fragments, single-chain Fvs (scFv), single-chain antibodies, disulfide-linked Fvs (sdFvs), fragments comprising, or alternatively consisting of, either a VL or VH domain, and epitope binding fragments of any of the above.

IL-9-binding antibody fragments, including single-chain antibodies, may comprise, or alternatively consist of, the variable region(s) alone or in combination with the entirety or a portion of the following: hinge region, CH1, CH2, and CH3 domains. In a preferred embodiment, the antibodies of the invention comprise, or alternatively consist of a polypeptide that immunospecifically binds to IL-9, said polypeptides comprise, or alternatively consist of, one, two, three, four, five, six or more CDRs contained in MH9A3, MH9D1, or MH9L1, preferably a polypeptide having an amino acid sequence of a VH CDR3 and/or a VL CDR3 of MH9A3, MH9D1, or MH9L1. Most preferably, antibodies of the invention comprise, or alternatively consist of, one, two, three, four, five, six or more CDRs from the same scFv, of MH9A3, MH9D1, or MH9L1. As used herein, "human" antibodies include antibodies having the amino acid sequence of a human immunoglobulin and include antibodies isolated from human immunoglobulin libraries and xenomic or other organisms that have been genetically engineered to produce human antibodies. For a detailed discussion of a few of the technologies for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; and Lonberg and Huszar, Int. Rev. Immunol. 13:65-93 (1995), which are incorporated by reference herein in their entirety. Human antibodies or "humanized" chimeric monoclonal antibodies can be produced using techniques described herein or otherwise known in the art. For example, methods for producing chimeric antibodies are known in the art. See, for review the following references which are hereby incorporated in their entirety: Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); 121 Neuberger et al, Nature 314:268 (1985). In addition, companies such as Abgenix, Inc. (Freemont, Calif.) and Genpharm (San Jose, Calif.) can be engaged to provide human antibodies directed against a selected antigen using technology similar to that described above.

The antibodies of the present invention may be monovalent, bivalent, trivalent or multivalent. For example, monovalent scFvs can be multimerized either chemically or by association with another protein or substance. An scFv that is fused to a hexahistidine tag or a Flag tag can be multimerized using Ni-NTA agarose (Qiagen) or using anti-Flag antibodies (Stratagene, Inc.).

The antibodies of the present invention may be monospecific, bispecific, trispecific or of greater multispecificity. Multispecific antibodies may be specific for different epitopes of an IL-9 polypeptide, or fragment thereof, or may be specific for both an IL-9 polypeptide, or fragment thereof, and a heterologous epitope, such as a heterologous polypeptide or solid support material. See, e.g., PCT publications WO 93/17715; WO 92/08802; WO 91/00360; WO 92/05793; Tutt, et al, J. Immunol. 147:60 69 (1991); U.S. Pat. Nos. 4,474,893; 4,714,681; 4,925,648; 5,573,920; 5,601,819; Kostelny et al, J. Immunol. 148:1547-1553 (1992).

The antibodies of the invention (including molecules comprising, or alternatively consisting of, antibody fragments or variants thereof) may bind immunospecifically to human IL-9.

Antibodies of the present invention may also be described or specified in terms of their cross-reactivity. Antibodies that do not bind any other analog, ortholog, or homolog of an IL-9 polypeptide are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art, and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under hybridization conditions (as described herein).

In preferred embodiments, the antibodies of the present invention (including molecules comprising, or alternatively consisting of, antibody fragments or variants thereof), immunospecifically bind to IL-9 and do not cross-react with any other antigens.

The present invention also provides for a nucleic acid molecule, generally isolated, encoding an antibody of the invention (including molecules comprising, or alternatively consisting of, antibody fragments or variants thereof). In one embodiment, a nucleic acid molecule of the invention encodes an antibody comprising, or alternatively consisting of, a VH domain having an amino acid sequence of any one of the VH domains of MH9A3, MH9D1, or MH9L1. In another embodiment, a nucleic acid molecule of the present invention encodes an antibody comprising, or alternatively consisting of, a VH CDR1 having an amino acid sequence of MH9A3, MH9D1, or MH9L1. In another embodiment, a nucleic acid molecule of the present invention encodes an antibody comprising, or alternatively consisting of, a VH CDR2 having an amino acid sequence of any one of the VH CDR2 of MH9A3, MH9D1, or MH9L1. In yet another embodiment, a nucleic acid molecule of the present invention encodes an antibody comprising, or alternatively consisting of, a VH CDR3 having an amino acid sequence of MH9A3, MH9D1, or MH9L1. Nucleic acid molecules encoding antibodies that immunospecifically bind IL-9 and comprise, or alternatively consist of, fragments or variants of the VH domains and/or VH CDRs are also encompassed by the invention.

In another embodiment, a nucleic acid molecule of the invention encodes an antibody (including molecules comprising, or alternatively consisting of, antibody fragments or variants thereof), comprising, or alternatively consisting of, an VL domain having an amino acid sequence of any one of the VL, domains of MH9A3, MH9D1, or MH9L1. In another embodiment, a nucleic acid molecule of the present invention encodes an antibody comprising, or alternatively consisting of, a VL CDR1 having amino acid sequence of any one of the VL CDR1 of MH9A3, MH9D1, or MH9L1. In another embodiment, a nucleic acid molecule of the present invention encodes an antibody comprising, or alternatively consisting of, a VL CDR2 having an amino acid sequence of any one of the VL CDR2 of MH9A3, MH9D1, or MH9L1. In yet another embodiment, a nucleic acid molecule of the present invention encodes an antibody comprising, or alternatively consisting of, a VL CDR3 having an amino acid sequence of any, one of the VL CDR3 of MH9A3, MH9D1, or MH9L1. Nucleic acid encoding antibodies that immunospecifically bind IL-9 and comprise, or alternatively consist of, fragments or variants of the VL domains and/or VLCDR(s) are also encompassed by the invention.

In another embodiment, a nucleic acid molecule of the invention encodes an antibody comprising, or alternatively consisting of, a VH domain having an amino acid sequence of any one of the VH domains of MH9A3, MH9D1, or MH9L1 and a VL domain having an amino acid sequence of any one of the VL domains of MH9A3, MH9D1, or MH9L1. In another embodiment, a nucleic acid molecule of the invention encodes an antibody comprising, or alternatively consisting of, a VH CDR1, a VL CDR1, a VH CDR2, a VL CDR2, a VH CDR3, a VL CDR3, or any combination thereof having an amino acid sequence of MH9A3, MH9D1, or MH9L1. Nucleic acid encoding antibodies that immunospecifically bind IL-9 and comprise, or alternatively consist of, fragments or variants of the VL and/or domains and/or VHCDR(s) and/or VLCDR(s) are also encompassed by the invention.

The present invention also provides antibodies that comprise, or alternatively consist of, variants (including derivatives) of the VH domains, VH CDRs, VL domains, and VL CDRs described herein, which antibodies immunospecifically bind to IL-9. Standard techniques known to those of skill in the art can be used to introduce mutations in the nucleotide sequence encoding a molecule of the invention, including, for example, site-directed mutagenesis and PCR-mediated mutagenes is which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. In specific embodiments, the variants encode substitutions of VHCDR3. In a preferred embodiment, the variants have conservative amino acid substitutions at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind IL-9). Following mutagenesis, the encoded protein may routinely be expressed and the functional and/or biological activity of the encoded protein, (e.g., ability to immunospecifically bind IL-9) can be determined using techniques described herein or by routinely modifying techniques known in the art.

The antibodies of the invention include derivatives (i.e., variants) that are modified, e.g., by the covalent attachment of any type of molecule to the antibody such that covalent attachment does not affect the ability of the antibody to immunospecifically bind to IL-9. For example, but not by way of limitation, derivatives of the invention include antibodies that have been modified, e.g., by glycosylation, acetylation, pegylation, phosphorylation, amidation, derivatization by known protecting/blocking groups, proteolytic cleavage, linkage to a cellular ligand or other protein, etc.

Any of numerous chemical modifications may be carried out by known techniques, including, but not, limited to, specific chemical cleavage, acetylation, formulation, metabolic synthesis of tunicamycin, etc. Additionally, the derivative may contain one or more non-classical amino acids.

In a specific embodiment, an antibody of the invention (including a molecule comprising, or alternatively consisting of, an antibody fragment or variant thereof), that immunospecifically binds IL-9, comprises, or alternatively consists of, an amino acid sequence encoded by a nucleotide sequence that hybridizes to a nucleotide sequence that is complementary to that encoding one of the VH or VL domains of MH9A3, MH9D1, or MH9L1 under stringent conditions, e.g., hybridization to filter-bound DNA in 6× sodium chloride/sodium citrate (SSQ at about 45° C. followed by one or more washes in 0.2×SSC/0.1% SDS at about 50°-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, Current Protocols in Molecular Biology, Vol. 1, Green Publishing 126 Associates, Inc. and John Wiley & Sons, Inc., New York at pages 6.3.1-6.3.6 and 2.10.3).

In another embodiment, an antibody of the invention that immunospecifically binds to IL-9, comprises, or alternatively consists of, an amino acid sequence encoded by a nucleotide sequence that hybridizes to a nucleotide sequence that is complementary to that encoding one of the VH CDRs or VL CDRs of MH9A3, MH9D1, or MH9L1 under stringent conditions, e.g., hybridization under conditions as described above, or under other stringent hybridization conditions which are known to those of skill in the art. In another embodiment, an antibody of the invention that immunospecifically binds to IL-9, comprises, or alternatively consists of, an amino acid sequence encoded by a nucleotide sequence that hybridizes to a nucleotide sequence that is complementary to that encoding one of the VH CDR3 of MH9A3, MH9D1, or MH9L1 under stringent conditions e.g., hybridization under conditions as described above, or under other stringent hybridization conditions which are known to those of skill in the art. Nucleic acid molecules encoding these antibodies are also encompassed by the invention.

In another embodiment, an antibody (including a molecule comprising, or alternatively consisting of, an antibody fragment or variant thereof), that immunospecifically binds to IL-9 comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VH domains of MH9A3, MH9D1, or MH9L1. In another embodiment, an antibody of the invention that immunospecifically binds to IL-9 comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VH CDRs of MH9A3, MH9D1, or MH9L1. In another embodiment, an antibody of the invention that immunospecifically binds to IL-9 comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to any one of the VH CDR3 of MH9A3, MH9D1, or MH9L1. Nucleic acid molecules encoding these antibodies are also encompassed by the invention.

In another embodiment, an antibody of the invention (including a molecule comprising, or alternatively consisting of, an antibody fragment or variant thereof), that immunospecifically binds to IL-9 comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL domains of MH9A3, MH9D1, or MH9L1. In another embodiment, an antibody of the invention that immunospecifically binds to IL-9 comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL CDRs of MH9A3, MH9D1, or MH9L1. In another embodiment, an antibody of the invention that immunospecifically binds to IL-9 comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL CDR3 of MH9A3, MH9D1, or MH9L1. Nucleic acid molecules encoding these antibodies are also encompassed by the invention.

Antibodies of the present invention (including molecules comprising, or alternatively consisting of, antibody fragments or variants thereof) may also be described or specified in terms of their binding affinity for to IL-9 polypeptides or fragments or variants of IL-9 polypeptides.

In specific embodiments, antibodies of the invention bind IL-9 polypeptides, or fragments or variants thereof, with a dissociation constant or $K_d$ of less than or equal to $5\times10^{-2}$M, $10^{-2}$ M, $5\times10^{-3}$M, $10^{-3}$M, $5\times10^{-4}$M, $10^{-4}$ M, $5\times10^{-5}$M, or $10^{-5}$ M. More preferably, antibodies of the invention bind IL-9 polypeptides or fragments or variants thereof with a dissociation constant or $K_d$ less than or equal to $5\times10^{-6}$ M, $10^{-6}$ M, $5\times10^{-7}$M, $10^{-7}$M, $5\times10^{-8}$M, or $10^{-8}$M. Even more preferably, antibodies of the invention bind IL-9 polypeptides or fragments or variants thereof with a dissociation constant or $K_d$ less than or equal to $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times-10^{-13}$M, $10^{-13}$M, $5\times10^{-14}$M, $10^{-14}$M, $5\times10^{-15}$ M, or $10^{-15}$M.

The invention encompasses antibodies that bind IL-9 polypeptides with a disassociation constant or $K_d$ that is within any one of the ranges that are between each of the individual recited values.

In specific embodiments, antibodies of the invention bind IL-9 polypeptides or fragments or variants thereof with an off rate (koff) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, antibodies of the invention bind IL-9 polypeptides or fragments or variants thereof with an off rate equal to or less than or equal to $5\times10^{-4}$ sec$^{-1}$, $10^{-4}$ sec$^{-1}$, $5\times10^{-5}$ sec$^{-1}$, or $10^{-5}$ sec$^{-5}$, $5\times10^{-6}$ sec$^{-1}$, $10^{-6}$ sec$^{-1}$, $5\times10^{-7}$ sec$^{-1}$ or $10^{-7}$ sec$^{-1}$. The invention encompasses antibodies that bind IL-9 polypeptides with an off rate (koff) that is within any one of the ranges that are between each of the individual recited values.

In other embodiments, antibodies of the invention bind IL-9 polypeptides or fragments or variants thereof with an on rate (Kon) greater than or equal to $10^{-3}$ $M^{-1}$ $sec^{-1}$, $5 \times 10^{-3}$ $M^{-1}$ $sec^{-1}$, $10^{-4}$ $M^{-1}$ $sec^{-1}$ or $5 \times 10^{-4}$ $M^{-1}$ $sec^{-1}$. More preferably, antibodies of the invention bind IL-9 polypeptides or fragments or variants thereof with an on rate, (Kon), of greater than or equal to $10^5$ $M^{-1}$, $sec^{-1}$, $5 \times 10^5$ $M^{-1}$ $sec^{-}$, $10^6$ $M^{-1}$ $sec^{-1}$, or $5 \times 10^6$ $M^{-1}$ $sec^{-1}$ or $10^7$ $M^{-1}$ $sec^{-1}$. The invention encompasses antibodies that bind IL-9 polypeptides with on rate, (Kon) that is within any one of the ranges that are between each of the individual recited values.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to IL-9 and/or an antigenic and/or epitope region of IL-9), the ability to substantially block IL-9/IL-9 receptor binding, or the ability to block IL-9 mediated biological activity. Optionally, the antibodies of the invention will bind to the same epitope as at least one of the antibodies specifically referred to, herein. Such epitope binding can be routinely determined using assays known in the art. To date, the antibodies which are neutralizing bind to the same epitope as determined by competitive binding studies (ELISA, BIA Core).

The present invention also provides for antibodies (including molecules comprising, or alternatively consisting of, antibody fragments or variants thereof), that neutralize IL-9 or a fragment thereof, said antibodies comprising, or alternatively consisting of, a portion (i.e., a VH domain, VL domain, VH CDRI, VH CDR2, VH CDR3, VL CDRI, VL CDR2, or VL CDR3) of an scFv of MH9A3, MH9D1, or MH9L1 or a fragment or variant thereof. By an antibody that neutralizes IL-9 or a fragment thereof is meant an antibody that diminishes or abolishes the ability of IL-9 to bind to its receptor or another biological activity of IL-9. In one embodiment, an antibody that neutralizes IL-9 or a fragment thereof, comprises, or alternatively consists of, a polypeptide having the amino acid sequence of, a VH domain of MH9A3, MH9D1, or MH9L1, or a humanized version thereof, or a fragment or variant thereof.

In another embodiment, an antibody that neutralizes IL-9 or a fragment thereof, comprises, or alternatively consists of, a polypeptide having the amino acid sequence of a VL domain of MH9A3, MH9D1, or MH9L1, or a fragment or variant thereof. In another embodiment, an antibody that neutralizes IL-9 or a fragment thereof, comprises, or alternatively consists of, a polypeptide having the amino acid sequence of a VH CDR domain of MH9A3, MH9D1, or MH9L1, or a fragment or variant thereof. In a preferred embodiment, an antibody that neutralizes IL-9 or a fragment thereof, comprises, or alternatively consists of, a polypeptide having the amino acid sequence of a VH CDR3 MH9A3, MH9D1, or MH9L1, or a fragment or variant thereof. In another embodiment, an antibody that neutralizes IL-9 or a fragment thereof, comprises, or alternatively consists of, a polypeptide having the amino acid sequence of a VL CDR domain contained in MH9A3, MH9D1, or MH9L1, or a fragment or variant thereof. In another preferred embodiment, an antibody that neutralizes IL-9 or a fragment thereof, comprises, or alternatively consists of, a polypeptide having the amino acid sequence of a VL CDR3 contained in MH9A3, MH9D1, or MH9L1, or a fragment or variant thereof. Nucleic acid molecules encoding these antibodies are also encompassed by the invention.

The present invention also provides for antibodies (including molecules comprising, or alternatively consisting of, antibody fragments or variants thereof), that inhibit (i.e., diminish or abolish) IL-9 mediated cell proliferation as determined by any method known in the art such as, for example, the assays described in the examples infra, said antibodies comprising, or alternatively consisting of, a portion (e.g., a VH domain, VL domain, VH CDRI, VH CDR2, VH CDR3, VL CDR1, VL CDR2, or VL CDR3) of an scFv having an amino acid sequence of MH9A3, MH9D1, or MH9L1 fragment or variant thereof. In one embodiment, an antibody that inhibits IL-9 mediated cell proliferation, comprises, or alternatively consists of, a polypeptide having the amino acid sequence of a VH domain contained in MH9A3, MH9D1, or MH9L1, or a fragment or variant thereof. In another embodiment, an antibody that inhibits IL-9 mediated cell proliferation comprises, or alternatively consists of, a polypeptide having the amino acid sequence of a VL domain contained in MH9A3, MH9D1, or MH9L1, or a fragment or variant thereof. In a preferred embodiment, an antibody that inhibits IL-9 mediated cell proliferation, comprises, or alternatively consists of, a polypeptide having the amino acid sequence of a VH CDR3 contained in MH9A3, MH9D1, or MH9L1, or a fragment or variant thereof. In another preferred embodiment, an antibody that inhibits IL-9 mediated cell proliferation, comprises, or alternatively consists of, a polypeptide having the amino acid sequence of a VL CDR3 contained MH9A3, MH9D1, or MH9L1, or a fragment or variant thereof. Nucleic acid molecules encoding these antibodies are also encompassed by the invention.

The present invention also provides for antibodies (including molecules comprising, or alternatively consisting of, antibody fragments or variants thereof), that enhance the activity of IL-9 or a fragment thereof, said antibodies comprising, or alternatively consisting of, a portion (i.e., a VH domain, VL domain, VH CDRI, VH CDR2, VH CDR3, VL CDRI, VL CDR2, or VL CDR3) of an scFv derived from MH9A3, MH9D1, or MH9L1, or a fragment or variant thereof. By an antibody that "enhances the activity of IL-9 or a fragment thereof is meant an antibody increases the ability of IL-9 to bind to its receptor. In one embodiment, an antibody that enhances the activity of IL-9 or a fragment thereof, comprises, or alternatively consists of, a polypeptide having the amino acid sequence of a VH domain contained of MH9A3, MH9D1, or MH9 L1 or variant thereof. In another embodiment, an antibody that enhances the activity of IL-9 or a fragment thereof, comprises, or alternatively consists of, a polypeptide having the amino acid sequence of a VL domain contained in MH9A3, MH9D1, or MH9L1, or a fragment or variant thereof. In another embodiment, an antibody that enhances the activity of IL-9 or a fragment thereof, comprises, or alternatively consists of, a polypeptide having the amino acid sequence of a VH CDR domain contained in MH9A3, MH9D1, or MH9L1, or a fragment or variant thereof. In a preferred embodiment, an antibody that enhances the activity of IL-9 or a fragment thereof, comprises, or alternatively consists of, a polypeptide having the amino acid sequence of a VH CDR3 contained in MH9A3, MH9D1, or MH9L1, or a fragment or variant thereof. In another embodiment, an antibody that enhances IL-9 or a fragment thereof, comprises, or alternatively consists of, a polypeptide having the amino acid sequence of a VL CDR domain contained in MH9A3, MH9D1, or MH9L1, or a fragment or variant thereof.

The present invention also provides for fusion proteins comprising, or alternatively consisting of, an antibody (including molecules comprising, or alternatively consisting of, antibody fragments or variants thereof), that immunospecifically binds to IL-9, and a heterologous polypeptide. Preferably, the heterologous polypeptide to which the antibody is fused to or is useful to target the antibody to desired cells. In another embodiment, the heterologous polypeptide to which the antibody is fused is albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, antibodies of the present invention (including fragments or variants thereof) are fused with the mature form of human serum albumin. In another preferred embodiment, antibodies of the present invention (including fragments or variants thereof) are fused with polypeptide fragments comprising, or alternatively consisting of, amino acid residues 1-x of human serum albumin, where x is an integer from 1 to 575 and the albumin fragment has human serum albumin activity. In another preferred embodiment, antibodies of the present invention (including fragments or variants thereof) are fused with polypeptide fragments comprising, or alternatively consisting of, amino acid residues 1-Z of human serum albumin, where z is an integer from 369 to 419, as described in U.S. Pat. No. 5,766,883 herein incorporated by reference in its entirety. Antibodies of the present invention (including fragments or variants thereof) may be fused to either the N- or C-terminal end of the heterologous protein (e.g., immunoglobulin Fc polypeptide or human serum albumin polypeptide).

In one embodiment, a fusion protein of the invention comprises, or alternatively consists of, a polypeptide having the amino acid sequence of any one or more of the VH domains of MH9A3, MH9D1, or MH9L1 or the amino acid sequence of any one or more of the VL domains of MH9A3, MH9D1, or MH9L1 or fragments or variants thereof, and a heterologous polypeptide sequence. In another embodiment, a fusion protein of the present invention comprises, or alternatively consists of, a polypeptide having the amino acid sequence of any one, two, three, or more of the VH CDRs of MH9A3, MH9D1, or MH9L1, or the amino acid sequence of any one, two, three, or more of the VL CDRs of MH9A3, MH9D1, or MH9L1, or fragments or variants thereof, and a heterologous polypeptide sequence. In a preferred embodiment, the fusion protein comprises, or alternatively consists of, a polypeptide having the amino acid sequence of, a VH CDR3 of MH9A3, MH9D1, or MH9L1, or fragment or variant thereof, and a heterologous polypeptide sequence, which fusion protein immunospecifically binds to IL-9. In another embodiment, a fusion protein comprises, or alternatively consists of a polypeptide having the amino acid sequence of at least one VH domain of MH9A3, MH9D1, or MH9L1 and the amino acid sequence of at least one VL domain MH9A3, MH9D1, or MH9L1 or fragments or variants thereof, and a heterologous polypeptide sequence. Preferably, the VH and VL domains of the fusion protein correspond to the same scFv. In yet another embodiment, a fusion protein of the invention comprises, or alternatively consists of a polypeptide having the amino acid sequence of any one, two, three or more of the VH CDRs of MH9A3, MH9D1, or MH9L1 and the amino acid sequence of any one, two, three or more of the VL CDRs of MH9A3, MH9D1, or MH9L1 or fragments or variants thereof, and a heterologous polypeptide sequence. Preferably, two, three, four, five, six, or more of the VHCDR(s) or VLCDR(s) correspond to the same antibody. Nucleic acid molecules encoding these fusion proteins are also encompassed by the invention.

The present invention also provides for mixtures of antibodies (including scFvs and other molecules comprising, or alternatively consisting of, antibody fragments or variants thereof) that immunospecifically bind to IL-9, wherein the mixture has at least one, two, three, four, five or more different antibodies of the invention.

The present invention also provides for panels of antibodies (including scFvs and other molecules comprising, or alternatively consisting of, antibody fragments or variants thereof) that immunospecifically bind to IL-9, wherein the panel has at least one, two, three, four, five or more different antibodies of the invention. In particular, the invention provides for panels of different antibodies that immunospecifically bind to the soluble form of IL-9, the membrane-bound form of IL-9, and/or both the membrane bound form and soluble form of IL-9. In specific embodiments, the invention provides for panels of antibodies that have different affinities for IL-9, different specificities for IL-9, or different dissociation rates. The invention provides panels of at least 10, preferably at least 25, at least 50, at least 75, at least 100, at least 125, at least 150, at least 175, at least –200, at least 250, at least 300, at least 350, at least 400, at least 450, at least 500, at least 550, at least 600, at least 650, at least 700, at least 750, at least 800, at least 850, at least 900, at least 950, or at least 1000, antibodies. Panels of antibodies can be used, for example, in 96 well plates for assays such as ELISAs.

The present invention provides for compositions comprising, one or more antibodies (including scFvs and other molecules comprising, or alternatively consisting of antibody fragments or variants of the invention). In one embodiment, a composition of the present invention comprises, one, two, three, four, five, or more antibodies that comprise or alternatively consist of, a polypeptide having an amino acid sequence of any one or more of the VH domains contained of MH9A3, MH9D1, or MH9L1, or a variant thereof. In another embodiment, a composition of the present invention comprises, one, two, three, four, five, or more antibodies that comprise, or alternatively consist of, a polypeptide having an amino acid sequence of any one or more of the VH CDR1 contained in MH9A3, MH9D1, or MH9L1 or a variant thereof. In another embodiment, a composition of the present invention comprises, one, two, three, four, five or more antibodies that comprise, or alternatively consist of, a polypeptide having an amino acid sequence of any one or more of the VH CDR2 contained in MH9A3, MH9D1, or MH9L1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3 contained in MH9A3, MH9D1, or MH9L1, as shown in FIGS. 1-4.

The present invention further provides for compositions comprising, one or more antibodies (including scFvs and other molecules comprising, or alternatively consisting of antibody fragments or variants of the invention). In one embodiment, a composition of the present invention comprises, one, two, three, four, five, or more antibodies that comprise or alternatively consist of, a polypeptide having an amino acid sequence of any one or more of the VH domains contained in MH9A3, MH9D1, or MH9L1, or a variant thereof. In another embodiment, a composition of the present invention comprises, one, two, three, four, five, or more antibodies that comprise, or alternatively consist of, a polypeptide having an amino acid sequence of any one or more of the VH CDR1s contained in MH9A3, MH9D1, or MH9L1, or a variant thereof. In another embodiment, a composition of the present invention comprises, one, two, three, four, five or more antibodies that comprise, or alternatively consist of, a polypeptide having an amino acid sequence of any one or more of the VH CDR2 contained in MH9A3, MH9D1, or MH9L1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3 contained in MH9A3, MH9D1, or MH9L1 or a variant thereof.

The present invention further provides for compositions comprising, one or more antibodies (including scFvs, or molecules comprising, or alternatively consisting of antibody fragments or variants of the invention). In one embodiment, a composition of the present invention comprises, one, two, three, four, five, or more antibodies that comprise or alternatively consist of, a polypeptide having an amino acid sequence of any one or more of the VH domains contained in MH9A3, MH9D1, or MH9L1, or a variant thereof. In another embodiment, a composition of the present invention comprises, one, two, three, four, five, or more antibodies that comprise, or alternatively consist of, a polypeptide having an amino acid sequence of any one or more of the VH CDR1 contained in MH9A3, MH9D1, or MH9L1, or a variant thereof. In another embodiment, a composition of the present invention comprises, one, two, three, four, five or more antibodies that comprise, or alternatively consist of, a polypeptide having an amino acid sequence of any one or more of the VH CDR2 contained in MH9A3, MH9D1, or MH9L1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3 contained in MH9A3, MH9D1, or MH9L1 or a variant thereof.

Other embodiments of the present invention providing for compositions comprising, one or more antibodies (including scFvs and other molecules comprising, or alternatively consisting of antibody fragments or variants of the invention) are listed below. In another embodiment, a composition of the present invention comprises, one, two, three, four, five, or more antibodies that comprise, or alternative consist of, a polypeptide having an amino acid sequence of any one or more of the VL domains contained in MH9A3, MH9D1, or MH9L1, or a variant thereof. In another embodiment, a composition of the present invention comprises, one, two, three, four, five, or more antibodies that comprise, or alternatively consist of, a polypeptide having an amino acid sequence of any one or more of the VL CDR1 contained in MH9A3, MH9D1, or MH9L1, or a variant thereof. In another embodiment, a composition of the present invention comprises, one, two, three, four, five, or more antibodies that comprise, or alternatively consist of, a polypeptide having an amino acid sequence of any one or more of the VL CDR2 contained in MH9A3, MH9D1, or MH9L1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3 contained in MH9A3, MH9D1, or MH9L1, or a variant thereof.

Other embodiments of the present invention providing for compositions comprising, one or more antibodies (including scFvs and other molecules comprising, or alternatively consisting of antibody fragments or variants of the invention) are listed below. In another embodiment, a composition of the present invention comprises, one, two, three, four, five, or more antibodies that comprise, or alternatively consist of, a polypeptide having an amino acid sequence of any one or more of the VL domains contained in MH9A3, MH9D1, or MH9L1, or a variant thereof. In another embodiment, a composition of the present invention comprises, one, two, three, four, five, or more antibodies that comprise, or alternatively consist of, a polypeptide, having an amino acid sequence of any one or more of the VL CDR1s contained in MH9A3, MH9D1, or MH9L1, or a variant thereof. In another embodiment, a composition of the present invention comprises, one, two, three, four, five, or more antibodies that comprise, or alternatively consist of, a polypeptide having an amino acid sequence of any one or more of the VL CDR2 of MH9A3, MH9D1, or MH9L1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3 contained in MH9A3, MH9D1, or MH9L1, or a variant thereof.

Other embodiments of the present invention providing for compositions comprising, one or more antibodies (including, scFvs and other molecules comprising, or alternatively consisting of antibody fragments or variants of the invention) are listed below. In another embodiment, a composition of the present invention comprises, one, two, three, four, five, or more antibodies that comprise, or alternatively consist of, a polypeptide having an amino acid sequence of any one or more of the VL domains contained in MH9A3, MH9D1, or MH9L1, or a variant thereof. In another embodiment, a composition of the present invention comprises, one, two, three, four, five, or more antibodies that comprise, or alternatively consist of, a polypeptide having an amino acid sequence of any one or more of the VL CDR1s contained in MH9A3, MH9D1, or MH9L1, or a variant thereof. In another embodiment, a composition of the present invention comprises, one, two, three, four, five, or more antibodies that comprise, or alternatively consist of, a polypeptide having an amino acid sequence of any one or more of the VL CDR2 of MH9A3, MH9D1, or MH9L1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3 contained in MH9A3, MH9D1, or MH9L1, or a variant thereof. In a preferred embodiment, a composition of the present invention comprises, one, two, three, four, five, or more antibodies that comprise, or alternatively consist of, a polypeptide having an amino acid sequence of any one or more of the VH domains of MH9A3, MH9D1, or MH9L1, or a variant thereof, and an amino acid sequence of any one or more of the VL domains of MH9A3, MH9D1, or MH9L1, or a variant thereof wherein the VH and VL domains are from scFvs with the same specificity. In yet another embodiment, a composition of the present invention comprises one or more fusion proteins.

As discussed in more detail below, a composition of the invention may be used either alone or in combination with other compositions. The antibodies (including scFvs and other molecules comprising, or alternatively consisting of antibody fragments or variants of the present invention) may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Antibodies of the present invention (including scFvs and other molecules comprising, or alternatively consisting of antibody fragments or variants of the present invention) may be used, for example, but not limited to, to purify and detect IL-9, and to target the polypeptides of the present invention to cells expressing membrane-bound IL-9 or IL-9 receptor, including both in vitro and in vivo diagnostic and therapeutic methods. For example, the antibodies have use in immunoassays for qualitatively and quantitatively measuring levels of IL-9 in biological samples. See, e.g., Harlow et al., Antibodies: A Laboratory Manual, (Cold Spring Harbor Laboratory Press, 2nd ed. 1988) (incorporated by reference herein in its entirety).

The antibodies of the invention (including scFvs and other molecules comprising, or alternatively consisting of antibody fragments or variants of the invention.) can be produced by any method known in the art for the synthesis of antibodies, in particular, by chemical synthesis or preferably, by recombinant expression techniques.

Single chain Fvs that immunospecifically bind IL-9 may be generated using phage display methods known in the art. In phage display methods, functional antibody domains are displayed on the surface of phage particles: which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by a scFv linker by PCR and cloned into a phagemid vector. The vector is electroporated in $E.$ $coli$ and the $E.$ $coli$ is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., IL-9 or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 18 79-18 (1997); Burton et al., Advances in Immunology 57:191-280 (1994); PCT application No. PCT/GB91/01 134; PCT publications WO 90/02809; WO 91/10737; WO 92/01047; WO 92/18619; WO 93/11236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427, 908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication WO 92/22324; Mullinax et al., BioTechniques 12(6):864 869 (1992); Sawai et al., AJR1 34:26-34 (1995); and Better et al., Science 240:1041-1043 (1988) (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

In other preferred embodiments, the invention provides antibodies that competitively inhibit binding of an antibody comprising a fragment (e.g., VH domain, VL domain, VHCDR1, VHCDR2, VHCDR3, VLCDRI, VLCDR2, or VLCDR3) or variant of a variable domain of MH9A3, MH9D1, or MH9L1 to an IL-9 polypeptide. In preferred embodiments, the invention provides antibodies that reduce the binding of an antibody comprising a fragment (e.g., VH domain, VL domain, VHCDRI, VHCDR2, VHCDR3, VLCDRI, VLCDR2, or VLCDR3) or variant of an scFv of MH9A3, MH9D1, or MH9L1 to an IL-9 polypeptide by between 1% and 10% in a competitive inhibition assay. In preferred embodiments, the invention provides antibodies that reduce the binding of an antibody comprising a fragment (e.g., VH domain, VL domain, VHCDR1, VHCDR2, VHCDR3, VLCDRI, VLCDR2, or VLCDR3) or variant of a variable domain of MH9A3, MH9D1, or MH9L1 IL-9 polypeptide by between 1% and 10% in a competitive inhibition assay.

In preferred embodiments, the invention provides antibodies that reduce the binding of an antibody comprising a fragment (e.g., VH domain, VL domain, VHCDRI, VHCDR2, VHCDR3, VLCDRI, VLCDR2, or VLCDR3) or variant of an scFv derived from MH9A3, MH9D1, or MH9L1 to an IL-9 polypeptide by at least 10% and up to 20% in a competitive inhibition assay.

In preferred embodiments, the invention provides antibodies that reduce the binding of an antibody comprising a fragment (e.g., VH domain, VL domain, VHCDR1, VHCDR2, VHCDR3, VLCDR1, VLCDR2, or VLCDR3) or variant of a variable domain derived from MH9A3, MH9D1, or MH9L1 to an IL-9 polypeptide by at least 20% and up to 30% in a competitive inhibition assay.

In preferred embodiments, the invention provides antibodies that reduce the binding of an antibody comprising a fragment (e.g., VH domain, VL domain, VHCDR1, VHCDR2, VHCDR3, VLCDRI, VLCDR2, or VLCDR3) or variant of a variable domain derived from MH9A3, MH9D1, or MH9L1 to an IL-9 polypeptide by at least 30% and up to 40% in a competitive inhibition assay.

In preferred embodiments, the invention provides antibodies that reduce the binding of an antibody comprising a fragment (e.g., VH domain, VL domain, VHCDR1, VHCDR2, VHCDR3, VLCDRI, VLCDR2, or VLCDR3) or variant of a variable domain derived from MH9A3, MH9D1, or MH9L1 to an IL-9 polypeptide by at least 40% and up to 50% in a competitive inhibition assay.

In preferred embodiments, the invention provides antibodies that reduce the binding of an antibody comprising a fragment (e.g., VH domain, VL domain, VHCDR1, VHCDR2, VHCDR3, VLCDR1, VLCDR2, or VLCDR3) or variant of a variable domain derived from MH9A3, MH9D1, or MH9L1 to an IL-9 polypeptide by at least 50% and up to 60% in a competitive inhibition assay.

In preferred embodiments, the invention provides antibodies that reduce the binding of an antibody comprising a fragment (e.g., VH domain, VL domain, VHCDRI, VHCDR2, VHCDR3, VLCDRI, VLCDR2, or VLCDR3) or variant of a variable domain derived from MH9A3, MH9D1, or MH9L1 to an IL-9 polypeptide by at least 60% and up to 70% in a competitive inhibition assay.

In preferred embodiments, the invention provides antibodies that reduce the binding of an antibody comprising a fragment (e.g., VH domain, VL domain, VHCDRI, VHCDR2, VHCDR3, VLCDRI, VLCDR2, or VLCDR3) or variant of a variable domain derived from MH9A3, MH9D1, or MH9L1 to an IL-9 polypeptide by at least 70% and up to 80% in a competitive inhibition assay.

In preferred embodiments, the invention provides antibodies that reduce the binding-of an antibody comprising a fragment (e.g., VH domain, VL domain, VHCDRI, VHCDR2, VHCDR3, VLCDRI, VLCDR2, or VLCDR3) or variant of a variable domain derived from MH9A3, MH9D1, or MH9L1 IL-9 polypeptide by at least 80% and up to 90% in a competitive inhibition assay.

In preferred embodiments, the invention provides antibodies that reduce the binding of an antibody comprising a fragment (e.g., VH domain, VL domain, VHCDRI, VHCDR2, VHCDR3, VLCDRI, VLCDR2, or VLCDR3) or variant of a variable domain derived from MH9A3, MH9D1, or MH9L1 to an IL-9 polypeptide by at least 90% and up to 100% in a competitive inhibition assay.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. In a specific embodiment, antibodies of the present invention comprise one or more VH and VL domains corresponding to the human variable domains of the invention and framework regions from another immunoglobulin molecule, preferably a human immunoglobulin molecule. In a specific embodiment, antibodies of the present invention comprise one or more CDRs corresponding to the human variable domains of the invention and framework regions from another immunoglobulin molecule, preferably a human immunoglobulin molecule. In other embodiments, an antibody of the present invention comprises one, two, three, four, five, six or more VL CDRs or VH CDRs corresponding to one or more of the human variable domains derived from MH9A3, MH9D1, or MH9L1, or fragments or variants thereof, and framework regions (and, optionally CDRs not derived from the variable domains of MH9A3, MH9D1, or MH9L1) from a human immunoglobulin molecule. In a preferred embodiment, an antibody of the present invention comprises a VH CDR3, VL CDR3, or both, corresponding to the same variable domains or fragments or variants thereof, and framework regions from a human immunoglobulin.

A chimeric antibody is a molecule in which different portions of the antibody are derived from different immunoglobulin molecules such as antibodies having a variable region derived from a human antibody and a non-human immunoglobulin constant region. Methods for producing chimeric antibodies are known in the art. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a canine or feline immunoglobulin molecule) can be produced using a variety of techniques known in the art including, for example, CDR-grafting (EP 239,400; PCT publication WO 91/09967; U.S. Pat. Nos. 5,225,539; 5,530,101; and 5,585, 089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 96:969-973 (1994)), and chain shuffling (U.S. Pat. No. 5,565,332). In a preferred embodiment, chimeric antibodies comprise a human CDR3 having an amino acid sequence of any one of the VH CDR3 or VL CDR3 of MH9A3, MH9D1, or MH9L1, or a variant thereof, and non-human framework regions or human framework regions different from those of the frameworks in the corresponding scFv of MH9A3, MH9D1, or MH9L1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.)

Further, the antibodies of the invention can, in turn, be utilized to generate anti-idiotype antibodies that "mimic" IL-9 polypeptides using techniques well known to those skilled in the art. (See, e.g., Greenspan & Bona, FASEB 17(5):437-444 (1993); and Nissinoff, J. Immunol. 147(8): 2429-2438 (1991)). For example, antibodies of the invention which bind to IL-9 and competitively inhibit the binding of IL-9 to its receptor (as determined by assays well known in the art such as, for example, that disclosed, infra) can be used to generate anti-idiotypes that "mimic" an IL-9 ligand/receptor-binding domain and, as a consequence, bind to and neutralize IL-9 receptors. Such neutralizing anti-idiotypes (including molecules comprising, or alternatively consisting of, antibody fragments or variants, such as Fab fragments of such anti-idiotypes) can be used in therapeutic regimens to neutralize IL-9. For example, such anti-idiotypic antibodies can be used to bind IL-9 ligands/receptors, and thereby block IL-9 mediated biological activity. Alternatively, anti-idiotypes that "mimic" an IL-9 binding domain may bind to IL-9 receptor(s) and induce IL-9 receptor mediated signaling. Such agonistic anti-idiotypes (including agonistic Fab fragments of these anti-idiotypes) can be used in therapeutic regimens to induce or enhance IL-9 receptor mediated signaling. For example, such anti-idiotypic antibodies can be used to bind IL-9 ligands/receptors, and thereby stimulate IL-9 mediated biological activity.

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. Since the amino acid sequences of the scFv antibodies and VH domains, VL domains and CDRs thereof, are known (as described in Table 1), nucleotide sequences encoding these antibodies can be determined using methods well known in the art, i.e., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al, BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody—(including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions. In a specific embodiment, one or more of the VH and VL domains of MH9A3, MH9D1, or MH9L1, or fragments or variants thereof, is inserted within framework regions using recombinant DNA techniques known in the art. In a specific embodiment, one, two, three, four, five, six, or more of the CDRs of MH9A3, MH9D1, or MH9L1, or fragments or variants thereof, is inserted within framework regions using recombinant DNA techniques known in the art. The framework regions may be naturally occurring or consensus framework regions, and preferably human framework regions (see, e.g., Chothia et al., J. Mol. Biol. 278: 457-479 (1998) for a listing of human framework regions, the contents of which are hereby incorporated by reference in its entirety). Preferably, the polynucleotides generated by the combination of the framework regions and CDRs encode an antibody (including molecules comprising, or alternatively consisting of, antibody fragments or variants thereof) that specifically binds to IL-9. Preferably, as discussed supra, polynucleotides encoding variants of antibodies or antibody fragments having one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

Recombinant Expression of an Antibody

Recombinant expression of an antibody of the invention (including scFvs and other molecules comprising, or alternatively consisting of, antibody fragments or variants thereof (e.g., a heavy or light chain of an antibody of the invention or a portion thereof or a single chain antibody of the invention)), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable, domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is (are) transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody of the invention, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected, with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA, expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al, Gene 45:101 (1986); Cockett et al, Bio/Technology 8:2 (1990)).

In bacterial systems, a number of expression vectors may be advantageously selected depending upon the use intended for the antibody molecule being being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al, EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. Also, vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. Such vectors are optionally designed to include thrombin or factor Xa protease cleavage sites so that the cloned target gene product can be released from the GST moiety.

In an insect system, *Autographa californica* nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 8 1:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al, Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, W138, and in particular, breast cancer cell lines such as, for example, BT483, Hs578T, HTB2, BT20 and T47D, and normal mammary gland cell line such as, for example, CRL7030 and HsS78Bst.

For long-term, high-yield production of recombinant proteins, stable expression is preferred. For example, cell lines which stably express the antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant, plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al, Cell 11:223 (1977)), hypoxanthineguanine phosphoribosyltransferase (Szybalski & Szybalski, Proc. Natl. Acad. Sci. USA 48:202 (1992)), and adenine phosphoribosyltransferase (Lowy et al, Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al, Natl. Acad. Sci. USA 77:357 (1980); OHare et al, Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260: 926-932 (1993); and Morgan and Anderson, Ann. Rev. Biochem. 62: 191-217 (1993); TIB TECH 11 (5):155-215 (May 1993)); andhygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al (eds), Current Protocols in Human Genetics, John Wiley & Sons, NY (1994); Colberre-Garapin et al, J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al. Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci., USA 77:2197 (1980)). The coding sequences for the heavy and light chains may comprise cDNA or genomic DNA.

Once an antibody molecule of the invention has been produced by recombinant expression, it may be purified by any method known in the art for purification of an immunoglobulin molecule, or more generally, for purification of a protein, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide: sequences described herein or otherwise known in the art to facilitate purification.

Antibodies of the present invention (including scFvs and other molecules comprising, or alternatively consisting of, antibody fragments or variants thereof) may be characterized in a variety of ways. In particular, antibodies and related molecules of the invention may be assayed for the ability to immunospecifically bind to IL-9 or a fragment of IL-9 using techniques described herein or routinely modifying techniques known in the art. IL-9 or IL-9 fragments that may be immunospecifically bound by the compositions of the invention include, but are not limited to, native human IL-9 or fragments or variants thereof. Preferably compositions of the invention bind human IL-9 or fragments thereof. Assays for the ability of the antibodies of the invention to immunospecifically bind IL-9 or a fragment of IL-9 may be performed in solution (e.g., Houghten, Bio/Techniques 158 13:412-421(1992)), on beads (e.g., Lam, Nature 354:82-84 (1991)), on chips (e.g., Fodor, Nature 364:555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249:404-406 (1990); Cwirla et al., Proc. Natl. Acad. Sci. USA 87:6378-6382 (1990); and Felici, J. Mol. Biol. 222:301-310 (1991)) (each of these references is incorporated herein in its entirety by reference). Antibodies that have been identified to immunospecifically bind to IL-9 or a fragment of IL-9 can then be assayed for their specificity and affinity for IL-9 or a fragment of IL-9 using or routinely modifying techniques described herein or otherwise known in the art.

The antibodies of the invention may be assayed for immunospecific binding to IL-9 and cross-reactivity with other antigens by any method known in the art. In particular, the ability of an antibody to immunospecifically bind to the soluble form or membrane-bound form of IL-9 and the specificity of the antibody, fragment, or variant for IL-9 polypeptide from a particular species (e.g., murine, monkey or human, preferably human) may be determined using or routinely modifying techniques described herein or otherwise known in art.

Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradionietric; assays, fluorescent immunoassays, and protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, 159 aprotinin, sodium vanadate), adding the antibody of interest to the cell lysate, incubating for a period of time (e.g., to 4 hours) at 40 degrees C., adding protein A and/or protein G sepharose beads to the cell lysate, incubating for about an hour or more at 40 degrees C., washing the beads in lysis buffer and re-suspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide get (e.g., 8%-20% SDS-PAGE depending on the molecular weight of the antigen), transferring the protein sample from the polyacrylamide get to a membrane such as nitrocellulose, PVDF or nylon, blocking the membrane, in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{12}P$ or $^{121}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, CinTent Protocols in Molecular Biology, Vol. 1, John Wiley & Sons, Inc., New York at 10.8.1.

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including a scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., $^{3}H$ or $^{121}I$) with the antibody of interest in the presence of increasing amounts of unlabeled antigen, and the detection of the antibody bound to the labeled antigen. The affinity of the antibody of the present invention for IL-9 and the binding off-rates can be determined from the data by Scatchard plot analysis. Competition with a second antibody can also be determined using radioimmunoassays. In this case, IL-9 is incubated with an antibody of the present invention conjugated to a labeled compound (e.g., $^{3}H$ or $^{125}I$) in the presence of increasing amounts of an unlabeled second anti-IL-9 antibody.

In a preferred embodiment, BIAcore kinetic analysis is used to determine the binding on and off rates of antibodies (including a scFv or other molecule comprising, or alternatively consisting of, antibody fragments or variants thereof) to IL-9, or fragments of IL-9. BIAcore kinetic analysis comprises analyzing the binding and dissociation of IL-9 from chips with immobilized antibodies on their surface.

The antibodies of the invention (including scFvs and other molecules comprising, or alternatively consisting of, antibody fragments or variants thereof) can also be assayed for their ability to inhibit, increase, or not significantly alter, the binding of IL-9 to an IL-9 receptor using techniques known to those of skill in the art. For example, cells expressing a receptor for IL-9 can be contacted with IL-9 in the presence or absence of an antibody, and the ability of the antibody to inhibit, increase, or not significantly alter, IL-9 binding to the cells can be measured. IL-9 binding to cells can be measured by, for example, flow cytometry or a scintillation assay. IL-9 or the antibody can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between IL-9 and an IL-9 receptor and/or IL-9 and an antibody of the invention. Alternatively, the ability of antibodies of the invention to inhibit, increase, or not significantly alter, IL-9 binding to an IL-9 receptor can be determined in cell-free assays. For example, native or recombinant IL-9 or a fragment thereof can be contacted with an antibody and the ability of the antibody to inhibit, increase, or not significantly alter, IL-9 from binding to an IL-9 receptor can be determined. Preferably, the antibody is immobilized on a solid support and IL-9 or an IL-9 fragment is labeled with a detectable compound. Alternatively, IL-9 or an IL-9 fragment is immobilized on a solid support and the antibody is labeled with a detectable compound. IL-9 may be partially or completely purified (e.g., partially or completely free of other polypeptides) or part of a cell lysate. Further, the IL-9 polypeptide may be a fusion protein comprising IL-9 or a biologically active portion thereof and a domain such as an Immunoglobulin Fe or glutathionine-S-transferase. Alternatively, IL-9 can be biotinylated using techniques well known to those of skill in the art (e.g., biotinylation kit, Pierce Chemicals; Rockford, Ill.).

The antibodies of the invention (including scFvs or other molecules comprising, or alternatively consisting of, antibody fragments or variants thereof), can also be assayed for their ability to inhibit, stimulate, or not significantly alter, IL-9-induced cell proliferation using techniques known to those of skill in the art. Further, the antibodies of the invention, or fragments or variants thereof, can be assayed for their ability to block, stimulate, or not significantly alter, IL-9-induced activation of cellular signaling molecules and transcription factors.

The antibodies of the invention, or fragments or variants thereof can also be assayed for their ability to neutralize, enhance, or not significantly alter, IL-9 activity. For example, antibodies or fragments or variants thereof, may be routinely tested for their ability to inhibit IL-9 from binding to cells expressing the receptor for IL-9.

The present invention encompasses antibodies (including scFvs and other molecules comprising, or alternatively consisting of, antibody fragments or variants thereof), recombinantly fused or chemically conjugated (including both covalent and non covalent conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies of the invention may be used to target heterologous polypeptides to particular cell types, either in vitro or in vivo, by fusing or conjugating the heterologous polypeptides to antibodies of the invention or which bind antigens that bind particular cell. Antibodies fused or conjugated to heterologous polypeptides may also be used in in-vitro immunoassays and purification methods using methods known in the art. See e.g., Harbor et al., supra, and PCT publication WO 93/21232; EP 439,095; Narainura. et al., Immunol. Lett. 39:91-99 (1994); U.S. Pat. No. 5,474,981; Gillies et al., PNAS 89:1428-1432 (1992); Fell et al., J. Immunol. 146:2446 2452 (1991), which are incorporated by reference in their entities.

The present invention farther includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab)2 fragment, or a portion thereof. Methods for fusing or conjugating polypeptides to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al, Proc. Natl. Acad. Sci. USA 88: 10535-10539 (1991); Zheng et al, J. Immunol. 154:5590 5600 (1995); and Vil et al, Proc. Natl. Acad. Sci. USA 89:11337-11341 (1992) (said references incorporated by reference in their entities).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including scFvs and other molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830,721; 5,834,252; and 5,837,458, and Patten et al, Curr. Opinion Biotechnol. 8:724 33 (1997); Harayama, Trends Biotechnol. 16(2):76-82 (1998); Hansson, et al, J. Mol. Biol. 287:265-76 (1999); and Lorenzo and Blasco, Biotechniques 24(2):308-13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions immunospecifically bind to IL-9 may be recombined with one or more components, motifs, sections, parts, domains, fragments, etc. of one or more heterologous molecules.

Moreover, the antibodies of the present invention (including scFvs; and other molecules comprising, or alternatively consisting of, antibody fragments or variants thereof), can be fused to marker sequences, such as a polypeptides to facilitate purification. In preferred embodiments, the marker amino acid sequence is a hexa histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the "flag" tag (DYKDDDDK, (SEQ 1D No: 3238) Stratagene, La Jolla, Calif.).

The present invention further encompasses antibodies (including scFvs and other molecules comprising, or alternatively consisting of, antibody fragments or variants, thereof), conjugated to a diagnostic or therapeutic agent. The antibodies can be used diagnostically to, for example, monitor or prognose the development or progression of a tumor as part of a clinical testing procedure to, e.g., determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidinTbiotin and avidin/biotin; examples of suitable fluorescent materials include, but are not limited to, 169 umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin; and examples of suitable radioactive material include, but are not limited to, radioactive species of iodine, carbon ($^{14}C$), sulfur ($^{35}S$), tritium ($^{3}H$), indium ($^{115m}In$, $^{113m}In$, $^{112m}In$,), and technetium, thallium, gallium ($^{67}Ga$), palladium, molybdenum, xenon ($^{133}Xe$), fluorine Rc, Bi, Lu, La, Yb, Ho, Ru, Sr, Sc, Sn, Gd, and Y.

Further, an antibody of the invention (including an scFv or other molecule comprising, or alternatively consisting of, antibody fragments or variants thereof), may be conjugated to a therapeutic moiety such as a cytotoxin, e.g., a cytostatic or cytocidal agent, a therapeutic agent or a radioactive metal ion, e.g., alpha-emitters such as, for example, $^{213}Bi$. In specific embodiments, antibodies of the invention are attached to macrocyclic chelators useful for conjugating radiometal ions, to polypeptides. In preferred embodiments, the radiometal ion associated with the macrocyclic chelators attached to antibodies of the invention is in. In preferred embodiments, the radiometal ion associated with the macrocyclic chelators attached to antibodies of the invention is $^{90}Y$. In specific embodiments, the macrocyclic chelator is 1,4,7,10-tetraazacyclododecane-N,N',N'',N'''-tetraacetic acid (DOTA). In other specific embodiments, the DOTA is attached to the antibody of the invention via a linker molecule. Examples of linker molecules useful for conjugating DOTA to a polypeptide are commonly known in the art—see, for example, DeNardo et al., Clin Cancer Res. 4(10):2483-90, 1998; Peterson et al., Biocoujug. Chem. 10(4):553-7, 1999; and Zimmerman et al, Nucl. Med. Biol. 26(8):943-50, 1999 which are hereby incorporated by reference in their entirety.

A cytotoxin or cytotoxic agent includes any agent that is detrimental to cells and includes such molecules as small molecule toxins and enzymatically active toxins of bacterial, fungal, plant, or animal origin, or fragments thereof. Examples include, but are not limited to, paclitaxol, cytochalasin B, gramicidin D, ethidiurn bromide, emetine, mitomycin, etoposide (VP-16), tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof. Therapeutic agents include, but are not limited to, antimetabolites (e.g., methotrexate, 6-mercaptopurine, 6-thioguanine, cytarabine, 5 fluorouracil decarbazine), alkylating agents (e.g., mechlorethamine, thioep4 chlorambucil, melphalan, carmustine (BSNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine), improsulfan, pipo-sulfan, benzodopa, carboquone, meturedopa, uredopa, altre-tamine, triet4ylenemetamine, trietylenephosphoramide, triethylenethiophosphaoraminde trimethylolomelamine, chlornaphazine, cholophosphamide, estramustine, ifosfamide, novembichin, phenesterine, prednimustine, trofosfamide, uracil mustard, chlorozotocin, flutemustine, nimustine, ranimustine, aclacinomysins, azaserine, cactinomycin, calichearnicin, carabicin, caminomycin, carzinophilin, chromomycins, detorubicin, 6-diazo-5-oxo-norleucine, epirubicin, esorubicin, idarubicin, marcellomycin, mycophenolic acid, nogalamycin, olivomycins, peplomycin, potfiromycin, quelamycin, rodorubicin, streptonigrin, tubercidin, ubenimex, zinostatin, zorubicin, denopterin, pteropterin, trimetrexate, fludarabine, thiamiprine, ancitabine, azacitidine, 6-azauridine, carmofur, dideoxyuridine, doxifluridine, enocitabine, floxuridine, 5-FU, calusterone, dromostanolone propionate, epitiostanol, mepitiostane, testolactone, aminoglutethimide, mitotane, trilostane, frolinic acid, aceglatone, aldophosphamide glycoside, aminolevulinic acid, arnsacrine, bestrabucil, bisantrene, edatraxate, defofamine, dernecolcine, diaziquone, elformithine, elliptiniurn acetate, etoglucid, gallium nitrate, hydroxyurea, lentinan, lonidamine, mitoguazone, mopidamol, nitracrine, pentostatin, phenamet, pirarubicin, podophyllinic acid, 2-ethylhydrazide, procarbazine, PSKO, razoxane, sizofuran, spirogermanium, tenuazonic acid, triaziquone, 2,2',2''-trichlorotriethylamine, urethan, vindesine, dacarbazine, mannomustine, mitobronitol, mitolactol, pipobroman, gacytosine, arabinoside ("Ara-C"), taxoids, e.g. paclitaxel (TAXOL", Bristol-Myers Squibb Oncology, Princeton, N.J.) doxetaxel (TAXOTERE", Rhone-Poulenc Rorer, Antony, France), gemcitabine, ifosfamide, vinorelbine, navelbine, novantrone, teniposide, aminopterin, xeloda, ibandronate, CPT-11, topoisomerase inhibitor RFS 2000, difluoromethylornithine (DMFO), retinoic acid, esperamicins, capecitabine, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, LY 117018, onapristone, toremifene (Fareston), and anti-androgens such as flutamide, nilutamide, bicalutamide, leuprolide, and goserelin, and pharmaceutically acceptable salts, acids or derivatives of any of the above.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudornonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF beta, AIM I (see, International Publication No. WO 97/33899), AIM II (see, International Publication No. WO 97/34911), Fas Ligand (Takahashi et al., Int. Immunol., 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-I (IL-1), interleukin-2 (IL-2), interleukin 6 (IL-6), granulocyte macrophage colony stimulating factor (GM-CSF), granulocyte colony stimulating factor (G-CSF), or other growth factors.

Antibodies of the invention (including scFvs and other molecules comprising, or alternatively consisting of, antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom. et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: At Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an scFv or and other molecule comprising, or alternatively consisting of, an antibody fragment or variant thereof), with or without a therapeutic moiety conjugated to it, administered alone or in combination with cytotoxic factor(s) and/or cytokine(s) can be used as a therapeutic.

The present invention provides antibodies (including scFvs and other molecules comprising, or alternatively consisting of, antibody fragments or variants thereof), that can be used to identify epitopes of IL-9. In particular, the antibodies of the present invention can be used to identify epitopes of human IL-9. Fragments which function as epitopes may be produced by any conventional means. (See, e.g., Houghten, Proc. Natl. Acad. Sci. USA 82:5131-5135 (1985), further described in U.S. Pat. No. 4,631,211.) Diagnostic Uses of Antibodies Labeled antibodies of the invention (including molecules comprising, or alternatively consisting of, antibody fragments or variants thereof) which specifically bind to IL-9 can be used for diagnostic purposes to detect, diagnose, prognose, or monitor diseases and/or disorders associated with the aberrant expression and/or activity of IL-9 or IL-9 receptor. The invention provides for the detection of aberrant expression of IL-9 comprising: (a) assaying the expression of IL-9 in a biological sample from an individual using one or more antibodies of the invention that immunospecifically binds to IL-9; and (b) comparing the level of IL-9 with a standard level of IL-9, e.g., in normal biological samples, whereby an increase or decrease in the assayed level of IL-9 compared to the standard level of IL-9 is indicative of aberrant expression.

By "biological sample" is intended any fluids and/or cells obtained from an individual, body fluid, body tissue, body cell, cell line, tissue culture, or other source which may contain IL-9 protein or mRNA. Body fluids include, but are not limited to, sera, plasma, urine, synovial fluid, bronchial alveolar lavage fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

The invention also provides for the detection of aberrant expression of IL-9 receptor comprising (a) assaying the expression of IL-9 receptor in a biological sample from an individual using one or more antibodies or fragments or variants thereof that immunospecifically binds only to soluble IL-9, but does not inhibit IL-9/IL-9 receptor binding.

Antibodies of the invention (including molecules comprising, or alternatively consisting of, antibody fragments or variants thereof) which specifically bind to IL-9 can be used for diagnostic purposes to detect, diapose, propose, or monitor autoimmune disorders and/or immunodeficiencies, and/or diseases or conditions associated therewith. The invention provides for the detection of aberrant expression of IL-9 comprising: (a) assaying the expression of IL-9 in a biological sample from an individual using one or more antibodies of the invention that immunospecifically binds to IL-9; and (b) comparing the level of IL-9 with a standard level of IL-9, e.g., in normal biological samples, whereby an increase or decrease in the assayed level of IL-9 compared to the standard level of IL-9 is indicative of an autoimmune disorder or disease and/or an immunodeficiency. In specific embodiments, an increase in the assayed level of IL-9 is indicative of an allergic disorder or disease such as autoimmune. In other specific embodiments, a decrease in the assayed level of IL-9 is indicative of an immunodeficiency. Aberrant IL-9 or IL-9 receptor production can be seen in myeloid, lymphoid and/or epithelial tissues.

Antibodies of the invention (including molecules comprising, or alternatively consisting of, antibody fragments or variants thereof) which specifically bind to IL-9 but, do not inhibit IL-9/IL-9 receptor binding can be used for diagnostic purposes to detect, diagnose, prognose, or monitor autoimmune disorders and/or immunodeficiencies, and/or diseases or conditions associated therewith. The invention provides for the detection of aberrant expression of IL-9 receptor comprising: (a) assaying the expression of IL-9 receptor in a biological sample from an individual using one or more antibodies of the invention that immunospecifically binds to IL-9; and (b) comparing the level of IL-9 receptor with a standard level of IL-9 receptor, e.g., in normal biological samples, whereby an increase or decrease in the assayed level of IL-9 receptor compared to the standard level of IL-9 receptor is indicative of an autoimmune disorder or disease and/or an immunodeficiency. In specific embodiments, an increase in the assayed level of IL-9 receptor is indicative of anautoimmune disorder or disease. In other specific embodiments, a decrease in the assayed level of IL-9 receptor is indicative of an immunodeficiency.

One aspect of the invention is the detection and diagnosis of a disease or disorder associated with aberrant expression of IL-9 or IL-9 receptor in an animal, preferably a mammal and most preferably a human. In one embodiment, diagnosis comprises: a) administering (for example, parenterally, subcutaneously, or intraperitoneally) to a subject an effective amount of a labeled antibody of the invention (including molecules comprising, or alternatively consisting of, antibody fragments or variants thereof) that immunospecifically binds to IL-9; b) waiting for a time interval following the administering for permitting the labeled antibody to preferentially concentrate at sites in the subject where IL-9 is expressed (and for unbound labeled molecule to be cleared to background level); c) determining background level; and d) detecting the labeled antibody in the subject, such that detection of labeled antibody or fragment thereof above the background level and above or below the level observed in a person without the disease or disorder indicates that the subject has a particular disease or disorder associated with aberrant expression of IL-9 or IL-9 receptor. Background level can be determined by various methods including, comparing the amount of labeled molecule detected to a standard value previously determined for a particular system. As noted above aberrant expression of IL-9 can occur particularly in lymphoid and myeloid cell types. Aberrant expression of IL-9 receptor can occur in lymphoid and epithelial tissues.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds, Masson Publishing Inc. (1982). [03851 Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to hours. In another embodiment the time interval following administration is 5 to 20 days or 5 to 10 days.

In an embodiment, monitoring of the disease or disorder is carried out by repeating the method for diagnosing the disease or disorder, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

The antibodies of the invention (including molecules comprising, or alternatively consisting of, antibody fragments or variants thereof) may be utilized for immunophenotyping of cell lines and biological samples by their IL-9 expression or IL-9 receptor expression. Various techniques can be utilized using antibodies, fragments, or variants of the invention to screen for cellular populations (that express IL-9 and/or IL-9 receptor, particularly immune cells, i.e., T and B lymphocytes, mast cells, eosinophils, macrophages, neutrophils and epithelial cells or IL-9 receptor, and include magnetic separation using antibody-coated magnetic beads, "panning" with antibody attached to a solid matrix (i.e., plate), and flow cytometry (see, e.g., U.S. Pat. No. 5,985, 660; and Morrison et al, Cell, 96:737-49 (1999)).

These techniques allow for the screening of particular populations of cells, such as might be found with hematological malignancies (i.e., minimal residual disease (MRD) in acute leukemic patients) and "non-self cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

The present invention is further directed to antibody-based therapies which involve administering antibodies of the invention (including molecules comprising, or alternatively consisting of, antibody fragments or variants thereof) to an animal, preferably a mammal, and most preferably a human, patient for treating one or more of the disclosed diseases, disorders, or conditions. Therapeutic compounds of the invention include, but are not limited to, antibodies of the invention and nucleic acids encoding antibodies (and anti-idiotypic antibodies) of the invention as described herein. The antibodies of the invention can be used to treat, ameliorate or prevent diseases, disorders or conditions associated with aberrant expression and/or activity of IL-9 or IL-9 receptor, including, but not limited to, any one or more of the diseases, disorders, or conditions described herein. The treatment and/or prevention of diseases, disorders, or conditions associated with aberrant IL-9 expression and/or activity or aberrant IL-9 receptor expression and/or activity includes, but is not limited to, alleviating symptoms associated with those diseases, disorders or conditions. Antibodies of the invention may be provided in pharmaceutically acceptable compositions as known in the art or as described herein.

Antibodies of the present invention (including molecules comprising, or alternatively consisting of, antibody fragments or variants thereof) that function as agonists or antagonists of IL-9, preferably of IL-9-induced signal transduction, can be administered to an animal to treat, prevent or ameliorate a disease or disorder associated with aberrant IL-9 expression, lack of IL-9 function, aberrant IL-9 receptor expression, or lack of IL-9 receptor function or any disease or candidate wherein modulation of IL-9 is therapeutically beneficial. For example, antibodies of the invention which disrupt the interaction between IL-9 and its receptor may be administered to an animal to treat, prevent or ameliorate a disease or disorder associated with aberrant IL-9 expression, excessive IL-9 function, aberrant IL-9 receptor expression, or excessive IL-9 receptor function.

One or more antibodies of the present invention (including molecules comprising, or alternatively consisting of, antibody fragments or variants thereof) that immunospecifically bind to IL-9 may be used locally or systemically in the body as a therapeutic. The antibodies of this invention (including molecules comprising, or alternatively consisting of, antibody fragments or variants thereof) may also be advantageously utilized in combination with other monoclonal or chimeric antibodies, or with lymphokines.

Additionally, the subject antibodies may be administered in conjunction with other asthma therapeutic agents. Examples thereof are asthma agents listed in the Table 1 below:

TABLE 1

| | |
|---|---|
| leukotriene receptor antagonist | montelukast |
| | zafirlukast |
| | zileuton |
| Corticosteroids Adrenocorticoids, glucocorticoids | beclomethasone |
| | budesonide |
| | flunisolide |
| | fluticasone |
| | triamcinolone |
| | methlyprednisolone |
| | prednisolone |
| | prednisone |
| Beta2-agonists | albuterol |
| | bitolterol |
| | fenoterol |
| | isoetharine |
| | metaproterenol |
| | Pirbuterol |
| | Salbutamol |
| | terbutaline |
| | formoterol |
| | salmeterol |
| | salbutamol |
| | terbutaline |
| Anti-cholinergics | ipratropium bromide |
| | oxitropium bromide |
| Anti-IgE | |
| Soluble IL-4 | |
| Anti-IL-5 | |
| Anti-IL-4 | |
| PDE4-inhibitor | |
| IL-4 mutein | |
| NF-Kappa-B inhibitor | |
| VLA-4 inhibitor | |
| Anti-IL-13 | |
| CpG | |
| Anti-CD23 | |
| Selectin antagonist (TBC 1269) | |
| Tryptase inhibitors | |
| Cysteine protease inhibitor | |
| C3a receptor antagonist, including antibodies | |

The antibodies of the invention (including molecules comprising, or alternatively consisting of, antibody fragments or variants thereof) may be administered alone or in combination with other types of treatments (e.g., radiation therapy, chemotherapy, hormonal therapy, immunotherapy, anti-tumor agents, anti-angiogenesis and anti-inflammatory agents). Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

Antibodies of the present invention include humanized antibodies in which the CDRs of antibody MH9A3, MH9D1, or MH9L1 are combined with human framework regions, using methods well known in the art, as illustrated in the examples, below. These human framework regions are divided into four regions for convenience sake. The first framework region precedes (is N-terminal to) the first CDR, the second framework region occurs between the first and second CDRs, the third framework region occurs between the second and third CDRs, and the fourth framework region occurs after (is C-terminal to) the third CDR. Table 2, below, lists known framework sequences for the heavy and light chains. The first column lists the VH regions of the heavy chains which include the first, second, and third framework regions, with the first and second germline CDRs (i.e., heavy chain framework 1, CDR1, framework 2, CDR2, framework 3). The 44 VH sequences are reported in a study that sequenced the entire human Igh gene locus (Matsuda, F., et al., 1998, J. Exp. Med. 188:1973, which is hereby incorporated by reference in its entirety). The second column lists the various JH regions, which provide the fourth heavy chain framework region. The third column lists V1 regions which include the lambda light chain first, second, and third framework regions, with the first and second germline CDRs (i.e., lambda light chain framework 1—CDR 1—framework 2—CDR2—framework 3). These lambda sequences are reported in locus Kawasaki K, 1997, Genome Res. March; 7(3):250-61, which is hereby incorporated by reference in its entirety. The fourth column lists kappa light chain framework regions which include the kappa light chain first, second, and third framework regions, with the first and second germline CDRs (i.e., kappa light chain framework 1—CDR1—framework 2—CDR2—framework 3). These kappa sequences are reported in Kawasaki K, et al., Eur. J. Immunol. 2001 April; 31(4):1017-28; Schable K F and Zachau H G, 1993, Biol. Chem. Hoppe Seyler 1993 November; 374(11):1001-22. Brensing-Kuppers J. et al., 1997 Gene 1997 Jun. 3; 191(2):173-81 each of which is hereby incorporated by reference in its entirety. The fifth column lists the various Jκ regions, which provide the fourth light chain framework region.

Thus to generate a humanized heavy chain, framework regions 1, 2, and 3, from the sequences referenced in the first column and a framework region 4 from the second column are combined with heavy chain CDRs from antibody MH9A3, MH9D1, or MH9L1. The germline CDRs of the of these framework sequences are preferably omitted and replaced with the MH9A3, MH9D1, or MH9L1 CDRs. Similarly, to generate a humanized lambda light chain, framework regions 1, 2, and 3, from the sequences referenced in the third column and a light chain framework region 4 from the fifth column are combined with light chain CDRs from antibody MH9A3, MH9D1, or MH9L1. Alternatively, to generate a humanized kappa light chain, framework regions 1, 2, and 3, from the sequences referenced in the fourth column and a light chain framework region 4 from the fifth column are combined with light chain CDRs from antibody MH9A3, MH9D1, or MH9L1. The framework regions 1, 2, and 3 can all be from the same sequence (e.g. all from VH1-18 for heavy, or all from V1-11 for lambda) or can be combined from different framework sources (e.g., framework 1 from VH1-18, framework 2 from VH1-2, and framework 3, from VH1-24 for heavy chains). This example is for illustrative purpose only, and should not in any way be considered limiting as to the combinations of framework regions that can be generated. In a similar manner, the light chain framework regions can be combined from different lambda or different kappa framework sources. The amino acid sequences of the heavy chain framework regions of the first column, the lambda chain framework sequences of the third column, and the kappa chain framework sequences of the fourth column can be found at the National Library of Medicine database at http://www.ncbi.nlm.nih.gov/igblast/showGermline.cgi, and are each sequence is hereby incorporated by reference in its entirety. Thus, the invention encompasses humanized antibodies and antibody fragments in which one, two, three, four, five or all six of the CDRs of antibodies MH9A3, MH9D1, or MH9L1 are combined with the framework regions of each individual framework listed in Table 2, as well as mixed combinations of the framework regions listed in Table 2.

TABLE 2

| Heavy Chain Frameworks | | Light Chain Frameworks | | |
|---|---|---|---|---|
| Heavy Chain Framework Regions 1, 2, 3 (with germline CDRs 1 and 2) | Heavy Chain Framework Region 4 | Lambda Light Chain Framework Regions 1, 2, 3 (with germline CDRs 1 and 2) | Kappa Light Chain Framework Regions 1, 2, 3 (with germline CDRs 1 and 2) | Light Chain Framework Region 4 |
| VH1-18 | JH1 (SEQ ID NO:130) | V1-11 | A1 | Jκ1 (SEQ ID NO:136) |
| VH1-2 | JH2 (SEQ ID NO:131) | V1-13 | A10 | Jκ2 (SEQ ID NO: 137) |
| VH1-24 | JH3 (SEQ ID NO:132) | V1-16 | A11 | Jκ3 (SEQ ID NO: 138) |
| VH1-3 | JH4 (SEQ ID NO:133) | V1-17 | A14 | Jκ4 (SEQ ID NO: 139) |
| VH1-45 | JH5 (SEQ ID NO:134) | V1-18 | A17 | Jκ5 (SEQ ID NO: 140) |
| VH1-46 | JH6 (SEQ ID NO:135) | V1-19 | A18 | |
| VH1-58 | | V1-2 | A19 | |
| VH1-69 | | V1-20 | A2 | |
| VH1-8 | | V1-22 | A10 | |
| VH2-26 | | V1-3 | A23 | |
| VH2-5 | | V1-4 | A26 | |
| VH2-70 | | V1-5 | A27 | |
| VH3-11 | | V1-6 | A3 | |
| VH3-13 | | V1-7 | A30 | |
| VH3-15 | | V1-9 | A5 | |
| VH3-16 | | V2-1 | A7 | |
| VH3-20 | | V2-11 | B2 | |
| VH3-21 | | V2-13 | B3 | |
| VH3-23 | | V2-14 | L1 | |
| VH3-30 | | V2-15 | L10 | |
| VH3-33 | | V2-17 | L11 | |
| VH3-35 | | V2-19 | L12 | |
| VH3-38 | | V2-6 | L14 | |
| VH3-43 | | V2-7 | L15 | |
| VH3-48 | | V2-8 | L16 | |
| VH3-49 | | V3-2 | L18 | |
| VH3-53 | | V3-3 | L19 | |
| VH3-64 | | V3-4 | L2 | |
| VH3-66 | | V4-1 | L20 | |

TABLE 2-continued

| Heavy Chain Frameworks | | Light Chain Frameworks | | |
|---|---|---|---|---|
| Heavy Chain Framework Regions 1, 2, 3 (with germline CDRs 1 and 2) | Heavy Chain Framework Region 4 | Lambda Light Chain Framework Regions 1, 2, 3 (with germline CDRs 1 and 2) | Kappa Light Chain Framework Regions 1, 2, 3 (with germline CDRs 1 and 2) | Light Chain Framework Region 4 |
| VH3-7 | | V4-2 | L22 | |
| VH3-72 | | V4-3 | L23 | |
| VH3-73 | | V4-4 | L24 | |
| VH3-74 | | V4-6 | L25 | |
| VH3-9 | | V5-1 | LV/18a | |
| VH4-28 | | V5-2 | L5 | |
| VH4-31 | | V5-4 | L6 | |
| VH4-34 | | V5-6 | L8 | |
| VH4-39 | | | L9 | |
| VH4-4 | | | O1 | |
| VH4-59 | | | O11 | |
| VH4-61 | | | O12 | |
| VH5-51 | | | O14 | |
| VH6-1 | | | O18 | |
| VH7-81 | | | O2 | |
| | | | O4 | |
| | | | O8 | |

It is preferred to use high affinity and/or potent in vivo inhibiting and/or neutralizing antibodies of the invention (including molecules comprising, or alternatively consisting of, antibody fragments or variants thereof) that immunospecifically bind to IL-9, or polynucleotides encoding antibodies that immunospecifically bind to IL-9, for both immunoassays directed to and therapy of disorders related to IL-9 polynucleotides or polypeptides, including fragments thereof. Such antibodies will preferably have an affinity for IL-9 and/or IL-9 fragments. Preferred binding affinities include those with a dissociation constant or $K_d$ less than or equal to $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, or $10^{-5}$ M. More preferably, antibodies of the invention bind IL-9 polypeptides or fragments or variants thereof with a dissociation constant or $K_d$ less than or equal to $5 \times 10^{-6}$ M, $10^{-6}$ M, $5 \times 10^{-7}$ M, $10^{-7}$ M, $5 \times 10^{-8}$ M, or $10^{-8}$ M. Even more preferably, antibodies of the invention bind IL-9 polypeptides or fragments or variants thereof with a dissociation constant or $K_d$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$. The invention encompasses antibodies that bind IL-9 polypeptides with a dissociation constant or $K_d$ that is within any one of the ranges that are between each of the individual recited values. In a preferred embodiment, antibodies of the invention neutralize IL-9 activity. In, another preferred embodiment, antibodies of the invention inhibit IL-9 mediated cell proliferation.

In a preferred embodiment, antibodies of the invention (including molecules comprising, or alternatively consisting of, antibody fragments or variants thereof) inhibit or reduce binding of the soluble form of IL-9 to an IL-9 receptor. In another preferred embodiment antibodies of the invention inhibit or reduce cell proliferation induced by the soluble form of IL-9.

In another embodiment, therapeutic or pharmaceutical compositions of the invention are administered to an animal to treat, prevent or ameliorate bronchial hyperresponsivness, atopic allergy including asthma, and other allergic disorders, lung disorders, and autoimmune disorders. Autoimmune disorders include e.g, arthritis, graft rejection, Hashimoto's thyroiditis, insulin-dependent diabetes, lupus, idiopathic—thrombocytopenic purpura, systemic lupus erythrematosus and multiple sclerosis), elective IgA deficiency, ataxia-telangiectasia, common variable immunodeficiency (CVID), X linked agammaglobulinemia, severe combined immunodeficiency (SCID), Wiskott Aldrich syndrome, idiopathic hyper-eosinophilic syndrome, monocytic leukemoid reaction, monocytic leukocytosis, monocytic leukopenia, monocytopenia, monocytosis, and graft or transplant rejection. Allergic disorders include in particular asthma.

Autoimmune disorders and conditions associated with these disorders that may be treated, prevented, ameliorated, diagnosed and/or proposed with the therapeutic and pharmaceutical compositions of the invention include, but are not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomeralonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitus, and autoimmune inflammatory eye disease.

Additional autoimmune disorders and conditions associated with these disorders that may be treated, prevented, ameliorated, diagnosed and/or proposed with the therapeutic and pharmaceutical compositions of the invention include, but are not limited to, autoimmune thyroiditis, hypothyroidism (i.e., Hashimoto's thyroiditis) (often characterized, e.g., by cell-mediated and humoral thyroid cytotoxicity), systemic lupus erythematosus (often characterized, e.g., by circulating and locally generated immune complexes), discoid lupus, Goodpasture's syndrome (often characterized, e.g., by anti basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoiMmune hemolytic anemia (often characterized, e.g., by phagocytosis of antibody-sensitized RBCs), autoimmune thrombocytopenic purpura (often characterized, e.g., by phagocytosis of antibody sensitized platelets.

Additional autoimmune disorders and conditions associated with these disorders that may be treated, prevented, ameliorated, diagnosed and/or prognosed with the therapeutic and pharmaceutical compositions of the invention include, but are not limited to, rheumatoid arthritis (often characterized, e.g., by immune complexes in joints), schleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell mediated adrenal cytotoxicity, infertility (often characterized, e.g., by antispermatozoal antibodies), glomerulonephritis (often characterized, e.g., by glomerular basement membrane antibodies or immune complexes) such as primary glomerulonephritis and IgA nephropathy bullous peniphigoid (often characterized, e.g., by IgG and complement in basement membrane), Sj6gren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies), chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic; dermatitis (often characterized, e.g., by IgG and IgM antibodies to IgE), asthma (often characterized, e.g., by IgG and IgM antibodies to IgE), inflammatory myopathies, and many other inflammatory, granulomatous, degenerative, and atrophic disorders.

In a preferred embodiment, therapeutic or pharmaceutical compositions of the invention are administered to an animal to treat, prevent or ameliorate bronchial hyperresponsivness or allergic disease or conditions. Examples of such allergic conditions include, but are not limited to, asthma, rhinitis, eczema, chronic urticaria, and atopic dermatitis, and preferably comprise allergic asthma. In another preferred embodiment the compositions will be used to treat disorders involving abnormal mucin production such as emphysema, COPD and cystic fibrosis.

In a specific embodiment, nucleic acids comprising sequences encoding antibodies or functional derivatives thereof, are administered to treat, inhibit or prevent a disease or disorder associated with aberrant expression and/or activity of IL-9 and/or its receptor, by way of gene therapy. Gene therapy refers to therapy performed by the administration to a subject of an expressed or expressible nucleic acid. In this embodiment of the invention, the nucleic acids produce their encoded protein that mediates a therapeutic effect. Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention or fragments or variants thereof are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr I gene to hernatopoietic stem cells in order to make the stem cells more resistant to chemotherapy. Other references illustrating the use of retroviral vectors in gene therapy are: Clowes et al., J. Clin. Invest. 93:644-651(1994); 219 Klein et al., Blood 83:1467-1473 (1994); Salmons and Gunzberg, Human Gene Therapy 4:129-141 (1993); and Grossman and Wilson, Curr. Opin. in Genetics and Devel. 3:110 114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775 783 (1995). In a preferred embodiment, adenovirus vectors are used. Adeno-associated virus (AAV) has also been proposed for use in gene, therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell mediated gene transfer, spheroplast fusion, etc. Numerous techniques are known in the art for the introduction of foreign genes into cells (see, e.g., Loeffler and Behr, Meth. 220 Enzymol. 217:599-618 (1993); Cohen et al, Meth. Enzymol. 217:618-644 (1993); Clin. Pharma. Ther. 29:69-92 in (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stein or progenitor cells, in particular hematopoietic stem or progenitor cells, e.g., as obtained from bone marrow, umbilical cord blood, peripheral blood, fetal liver, etc. In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans.

Antibodies or compositions of the present invention for use in therapy can be tested for their toxicity in suitable animal model systems, including but not limited to rats, mice, chicken, cows, monkeys, and rabbits. For in vivo testing of an antibody or composition's toxicity any animal model system known in the art may be used.

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer antibody or fragment or variant thereof of the invention, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of introduction include, but are not limited to, intradermal, 224 intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527-1533 (1990); Treat et al, in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the composition can be delivered in a controlled release system. In one embodiment, a pump may be used (see Langer, supra; Sefton, CRC Crit. Ref. Biomed. Eng. 14:20 1 (1987); Buchwald et al, Surgery 88:507 (1980); Saudek et al, N. Engl. J. Med. 321:574 (1989)).

In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); 225 Ranger and Peppas, J., Macromol. Sci. Rev. Macromol. Chem. 23:61 (1983); see also Levy et al, Science 228:190 (1985); During et al, Ann. Neurol. 25:35 1 (1989); Howard et al, J. Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

In a specific embodiment where the composition of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al, Proc. Natl. Acad.-Sci. USA 88:1864-1868 (1991)), etc. Alternatively, a nucleic acid can be introduced intracellularly and incorporated within host cell DNA for expression, by homologous, recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable. pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a, patient is between 0.1 mg/kg and −20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

The antibodies and antibody compositions of the invention may be administered alone or in combination with other adjuvants. Adjuvants that may be administered with the antibody and antibody compositions of the invention include, but are not limited to, alum, alum plus deoxycholate (ImmunoAg), MTP-PE (Biocine Corp.), QS21 (Genentech, Inc.), BCG, and MPL. In a specific embodiment, antibody and antibody compositions of the invention are administered in combination with alum. In another specific embodiment, antibody, and antibody compositions of the invention are administered in combination with QS-21. Further adjuvants that may be administered with the antibody and antibody compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the antibody and antibody compositions of the invention include, but are not limited to, vaccines directed toward protection against N4MR (measles, mumps, 228 rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23. Combinations maybe administered either concomitantly, e.g., as an admixture, separately but simultaneously or concurrently; or sequentially. This includes presentations in which the combined agents are administered together as a therapeutic mixture, and also procedures in which the combined agents are administered separately, but simultaneously, e.g., as through separate intravenous lines into the same individual. Administration "in combination" further includes the separate administration of one of the compounds or agents given first, followed by the second.

The antibody and antibody compositions of the invention may be administered alone or in combination with other therapeutic agents, including but not limited to, chemotherapeutic agents, antibiotics, anti-virals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alternative embodiment, a kit comprises an antibody fragment that immunospecifically binds to IL-9. In a specific embodiment, the kits of the present invention contain a substantially isolated IL-9 polypeptide as a control. Preferably, the kits of the present invention further comprise a control antibody which does not react with IL-9. In another specific embodiment, the kits of the present invention contain a means for detecting the binding of an antibody to IL-9 (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized IL-9. The IL-9 provided in the kit may also be attached to a solid support. In a more specific embodiment the detecting means of the above-described kit includes a solid support to which IL-9 is attached. Such a kit may also include a non-attached reporter-labeled anti-human antibody. In this embodiment, binding of the antibody to IL-9 can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with IL-9, and means for detecting the binding of IL-9 to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

PREFERRED EMBODIMENTS OF THE INVENTION

Thus, the present invention encompasses recombinant anti-human interleukin 9 (IL-9) antibodies that inhibit IL-9 responses of human immune cells, particularly cells involved in asthma immune reactions. In particular, the invention is directed to recombinant anti-human IL-9 antibodies derived from three murine anti-human IL-9 antibodies referred to as MH9A3, MH9D1, and MH9L1, the production of which are disclosed in the examples infra. Such recombinant anti-human IL-9 antibodies include those selected from the group consisting of chimeric antibodies, humanized antibodies, F(Ab) fragments, F(Ab)$_2$ fragments, Fv fragments and human antibodies. Typically, chimeric anti-human IL-9 antibodies of the invention comprise rodent, i.e., murine or rat, variable chain sequences. Such antibodies may preferably comprise human Ig constant region domain sequences. Most preferred are human IgG1 constant regions as described in U.S. Pat. No. 5,824,307, herein incorporated by reference in its entirety.

Particularly preferred chimeric anti-human IL-9 antibodies of the invention have heavy chain CDR sequences essentially having at least 90% sequence identify either SEQ ID NO: 3, SEQ ID NO: 4, or SEQ ID NO: 128 (sequences of the MH9A3, MH9D1, or MH9L1 chimeric heavy chains, respectively) (FIG. 3), and light chain CDR sequences at least 90% sequence identify to identical to either SEQ ID NO: 5, SEQ ID NO: 6, or SEQ ID NO: 129 (sequences of MH9A3, MH9D1, or MH9L1 chimeric light chains, respectively) (FIG. 4). "Essentially identical" means antibodies having heavy and light chains having essentially the same sequences as SEQ ID NOs: 3, 4 or 128, and 5, 6 or 129, respectively, including antibodies with inconsequential changes in the sequences that retain at least one the IL-9 inhibitory function of the antibody.

Also included in the present invention are DNA molecules encoding the antibody heavy chain and light chain sequences described herein. For instance, SEQ ID NO: 1 is a DNA sequence encoding the light chain of the chimeric MH9A3 antibody (FIG. 1), and SEQ ID NO: 2 is a DNA sequence encoding the MH9A3 heavy chain (FIG. 2). Vectors comprising such sequences, as well as host cells comprising such sequences and vectors are also included.

Figure 8:
FIG. 8 contains the sequences of antibody heavy chains VH1-69 and VH 3-21 (SEQ ID NOs: 9 & 10) obtained via rational design optimization of the MH9D1 chimeric antibody, as compared to MD9D1 and the homologous human H1 (1-69) (SEQ ID NO: 15) and H2 (3-21) (SEQ ID NO: 16) sequences.
Figure 10:
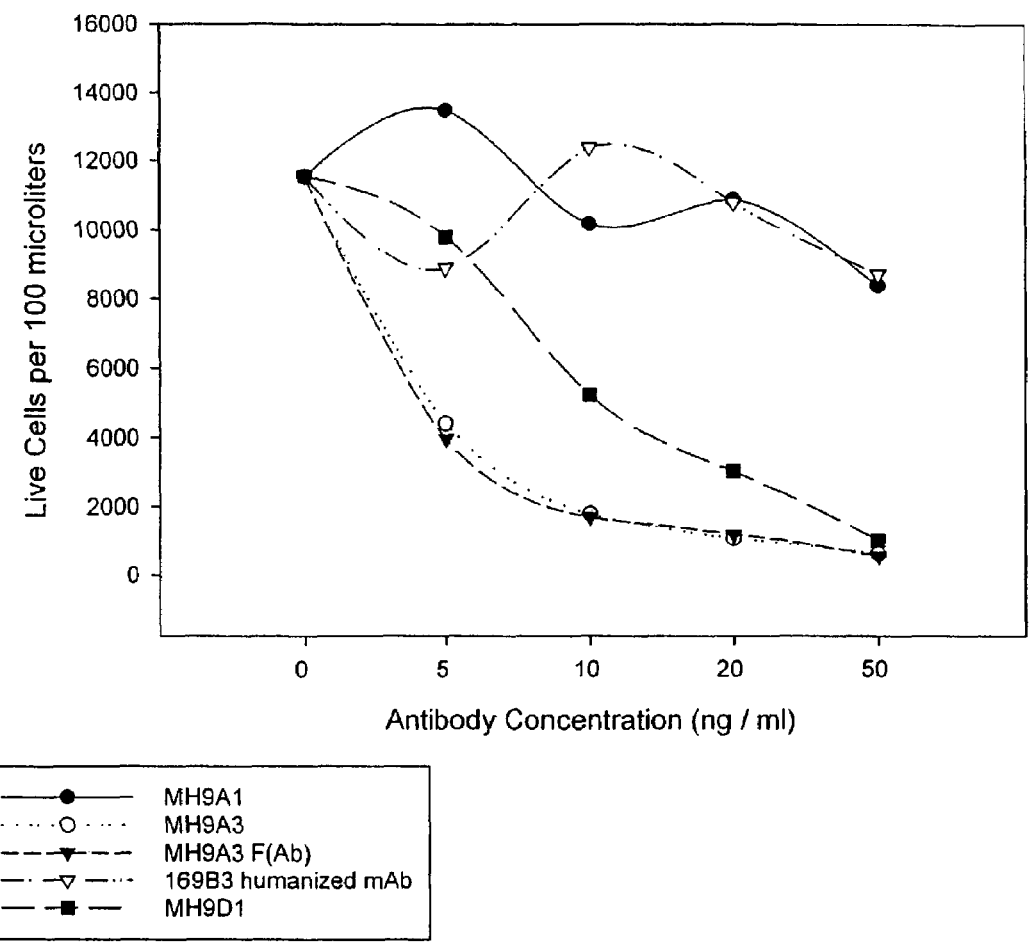
FIG. 10 contains the graph showing inhibition of TS1-RA3 proliferation by anti-IL-9 antibodies, including MH9A1 (-●-), MH9A3 whole (····○····), MH9A3 F(Ab) (--▼--), 1-69 (B3) humanized (-·-∇-·-) and MH9D1 (- -■- -) antibodies.
Figure 12:
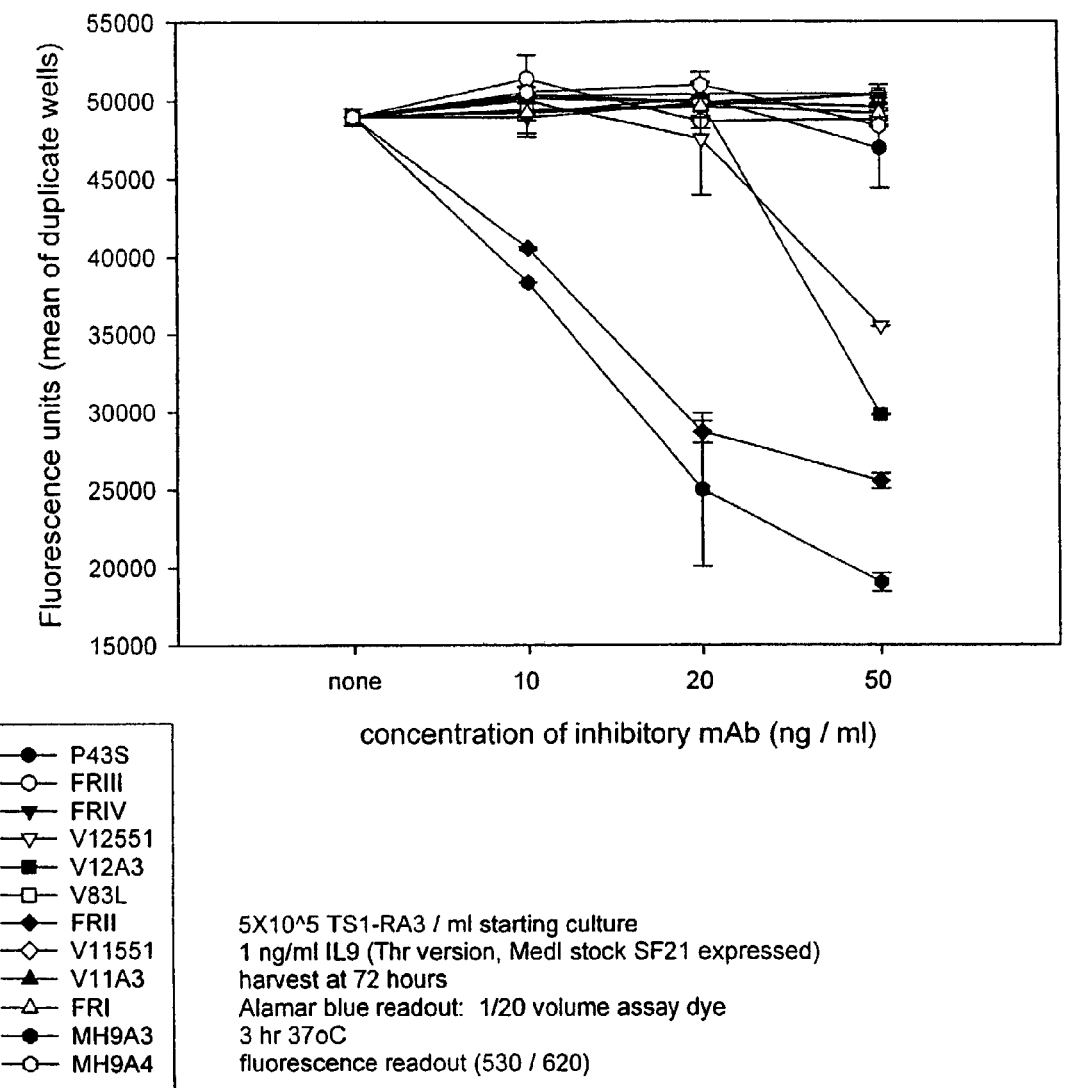
FIG. 12 contains a graph showing inhibition of TS1-RA3 proliferation by anti-IL-9 antibodies, including P43S (the P43S light chain variant paired with the original MH9A3 heavy chain) (-●-), FRIII (the FRIII light chain variant paired with the original MH9A3 heavy chain) (-○-), FRIV (the FRIV light chain variant paired with the original MH9A3 heavy chain) (-▼-), V12551 (the V12 light chain paired with the humanized MH9A3 5-51 heavy chain) (-∇-), V12A3 (the V12 light chain paired with the original MH9A3 heavy chain) (-■-), V83L (the V83L light chain variant paired with the original MH9A3 heavy chain) (-□-), FRII (the FRII light chain variant paired with the original MH9A3 heavy chain) (-♦-), V11551 (the V11 light chain paired with the humanized MH9A3 5-51 heavy chain) (-◇-), V 11A3 (the V11 light chain paired with the original MH9A3 heavy chain) (-▲-), FRI (the FRI light chain variant paired with the original MH9A3 heavy chain) (-▼-), and MH9A3 (●) and MH9A4 (○) antibodies.

Particularly preferred humanized anti-human IL-9 antibodies of the invention are made by PCR-based mutagenesis of a murine anti-human antibody IL-9 based on homology matching to a human antibody (rational design based on homology matching). Such antibodies in particular have a heavy chain sequence selected from the group consisting of SEQ ID NOs: 7 (A3-1-69), 8 (A3-5-51), 9 (D1-1-69) and 10 (D1-3-21) (representing the heavy chain sequences for the two humanized versions for each of A3 and D1 made in this manner) (FIGS. 6 and 8). Heavy chains having the sequences of SEQ ID NOs: 7 and 8 will be preferably paired with light chains having essentially the sequence of SEQ ID NO: 11 (B3, the humanized light chain sequence for MH9A3 derivatives) (FIG. 6). Heavy chains having the sequences of SEQ ID NOs: 9 and 10 will be preferably paired with light chains having essentially the sequence of SEQ ID NO: 12 (L1, the humanized light chain sequence for MH9D1 derivatives) (FIG. 8).

An alternative approach for isolating the humanized anti-human IL-9 antibodies of the invention is by successive panning of a phage display framework library. This approach is based on the method disclosed in Rader et al., 1998, Proc. Natl. Acad. Sci. USA 95: 8910-15, which is herein incorporated by reference in its entirety. The method generally entails producing a phagemid vector library of humanized molecules using nucleic acid sequences amplified from human germline heavy and light chains, and successively panning the phagemid vector library for phages that display antibody sequences that bind to immobilized human IL-9. Particularly preferred antibodies identified in this manner have a light chain sequence selected from the group consisting of SEQ ID NOs: 13-18 (there were six different light chain sequences for A3 identified after 3 rounds of panning).

The present invention also includes methods of identifying neutralizing epitopes of IL-9, comprising identifying the epitopes recognized by the antibodies described herein. Such epitopes may be identified by binding the antibodies to a library of peptide fragments, i.e., as displayed on the surface of a phage such as M13, and identifying the fragments to which the antibodies bind. Such a library may consist of random peptide fragments, or a library of IL-9 fragments. When IL-9 fragments are used, such fragments may be either contiguous, i.e., linear, or non-contiguous, i.e., conformational or made up of smaller non-linear peptides.

The neutralizing epitopes of the present invention may also be identified by binding the antibodies of the present invention to a library of mutated IL-9 proteins or peptides. A preferred library consists of proteins and peptides wherein potentially exposed residues are mutated into alanine residues. Binding to the antibodies of the invention to IL-9 may be tested by various methods e.g., by ELISA and/or calorimetry and/or BIAcore.

The present invention also encompasses compositions comprising the anti-human IL-9 antibodies and/or peptides of the invention, particularly pharmaceutical compositions that also include an appropriate pharmaceutical carrier and optionally other pharmaceutical compounds, for instance those useful for the treatment of asthma or other conditions wherein modulation or inhibition of IL-9 activity are therapeutically beneficial. Also included are methods of inhibiting or preventing an IL-9 response of a cell in vitro by adding to a culture either the antibodies or the peptides or the compositions of the invention, as well as methods of inhibiting or preventing such responses in vivo by administering to a patient the antibodies or peptides or compositions of the invention. The recombinant antibodies of the invention derived from MH9A3, MH9D1, and MH9L1 may be used to treat and/or prevent any disease condition wherein modulation of IL-9 expression and/or at least one IL-9 function is beneficial.

In particular the subject antibodies may inhibit mucin production, the infiltration of inflammatory cells such as T cells, B cells, mast cells, eosinophils and neutrophils, and/or inhibit epithelial cell hyperplasia.

In a preferred embodiment, the in vivo methods of the present invention will be used to treat a patient with bronchial hyperresponsivness related to COPD, cystic fibrosis, or other chronic respiratory conditions, or a patient suffering with atopic allergy including asthma symptoms. Such methods will comprise administering to a patient with bronchial hyperresponsivnessan or suffering with a form of atopic allergy, including but not limited to asthma, an amount of recombinant anti-human IL-9 antibody or peptide effective to reduce the symptoms. The antibody or peptide may exhibit a variety of functional effects, including the neutralization of interleukin-9 in the patient, the down-regulation of one or more activities of interleukin-9 in the patient (discussed above), the reduction of bronchial hyperresponsiveness in the patient, and/or the reduction of eosinophilia in the lungs of the patient. Such effects have been shown by the administration of polyclonal anti-murine IL-9 antibodies to asthmatic mice. It is anticipated that similar results will occur upon administration the subject of anti-human IL-9 antibodies to human patients given the conservation of this protein between humans and mice and the expected advantageous of such antibodies (low immunogenicity high affinity for IL-9). See U.S. Pat. No. 5,824,307, herein incorporated by reference.

In the therapeutic methods of the present invention, the antibody or peptide may be administered by any suitable route, including those selected from the group consisting of intravenous, intraperitoneal, inhalation, intramuscular, subcutaneous and oral. A particularly preferred route of administration for treating patients suffering with rhinnitis or asthma is via the inhalation route, and as such the invention also encompasses inhalation devices that may be used to deliver to patients a therapeutically effective amount of the recombinant anti-human IL-9 antibodies described herein.

In a preferred embodiment the subject antibodies will be used in conjunction with other asthma therapies. Examples thereof include steroids, anti-inflammatories, antibodies to other lymphokines such as IL-13, IL-4 and IL-5 therapeutics, xolair, C3a antagonists, leukotrien inhibitor etc. Preferred compounds for combination therapy with the subject antibodies include leukotrien inhibitors, anti-IL-13, and anti-adrevin agents, alone or in combination.

The following examples are illustrative, but not limiting, of the present invention.

EXAMPLE 1

Isolation of Neutralizing Murine Anti-Human IL-9 Antibodies

SJL mice are immunized with Baculovirus-expressed recombinant IL-9 purchased from R+D Systems, complexed with Ovalbumin from Sigma. A proprietary adjuvant from Glaxo Smith Kline called SBAS-1C was used in this procedure. Several IL-9-specific antibodies are isolated, including three neutralizing antibodies (MH9A3, MH9D1, and MH9L1). Sera and monoclonal antibodies derived from immunized mice are screened first in an ELISA assay for reactivity with the R+D Systems recombinant human IL-9. Positive sera and mAbs are subsequently tested for in vitro neutralization activity by testing the antibodies for the ability to inhibit TS 1-RA3 proliferation as described below.

Production of Chimeric Antibodies

For each neutralizing antibody, chimeras are constructed with Cγ1 Synagis and Cκ Synagis by grafting the variable region sequences onto a human IgG1 constant background (Synagis). Cloning was carried out using standard PCR protocols. XmaI/BsiWI and XbaI/ApaI restriction sites were used for cloning the light and heavy chains, respectively, into the expression vectors. FIGS. 1 and 2 provide the DNA sequences of the MH9A3 chimeric constructions for the light and heavy chain, respectively. The following oligonucleotides are used (restriction sites underlined):

For the MH9A3 Light Chain:

```
5'-TATATATATATATATACCCCGGGGCCAAATGTGACATTGTGATGACCCAGTCTC-3'    (SEQ D NO: 33)

5'-TATATATATATATACGTACGTPTCAGCTCCAGCTTGGTCCCAGC-3'              (SEQ ID NO:34)
```

For the MH9A3 Heavy Chain:

```
5'TATATATATATATATCTAGACATATATATGGGTGACAATGACATCCACTTTG    (SEQ ID NO: 35)
CCTTTCTCTCCACAGGTGTCCACTCCCAGGTTCAGCTGCAGCAGTC-3'
```

-continued

```
5'GCCAGGGGGAAGACCGATGGGCCCTTGGTGGAGGCTGAGGAGACTGTGAGA    (SEQ ID NO: 36)
GTGGTGCCTTGGCCCCAGTAGTC-3'
```

For the MH9D1 Light Chain:

```
                                            (SEQ ID NO: 37)
  5'-TCGCTACCCGGGGCCAAATGTGACATCCTGATGACCCAA-3'

(SEQ ID NO: 38)
  5'-AGCCACCGTACGTTTCATTTCCAGCTTGGT-3'
```

For the MH9D1 Heavy Chain:

```
5'GCTTGCGGTCTAGACATATATATGGGTGACAATGACATCCACTTTGCCTTTC    (SEQ ID NO: 39)
TCTCCACAGGTGTCCACTCCCAGGTCCAGCTGCAGCAG-3'

5'-GTATCCGATGGGCCCTTGGTGGAGGCTGCAGAGACAGTGACCAG-3'         (SEQ ID NO: 40)
```

MH9A3 and MH9D1-derived chimeras were transfected into 293 cells, purified on protein A columns and tested for activity using the in vitro neutralization assay described below. Amino acid sequences of the CDR regions of the heavy chains of the MH9A3 and MH9D1 antibodies are shown in FIG. 3. Amino acid sequences of the CDR regions of the light chains of the MH9A3 and MH9D1 antibodies are shown in FIG. 4.

In Vitro Neutralization Assay

TS1-RA3 is a murine T cell line, TS1, that has been genetically modified to overexpress the human IL9 receptor alpha (IL9Ra). The resulting cell line, TS1-RA3, is absolutely dependent on recombinant human IL9 for its growth. To test the effectiveness of anti-IL9 antibodies, TS1-RA3 cells are grown in a known concentration of recombinant IL9, in the presence of anti-IL9 antibodies. If the anti-IL9 antibodies are neutralizing, that the TS1-RA3 cells die over a period of 48 to 72 hours. Non-neutralizing antibodies have no effect on TS1-RA3 growth.

As shown in FIG. 5, antibody MH9A3, both whole and F(Ab) fragments, and antibody MH9D1 (hereinafter D1) are neutralizing in that exposure of TS1-RA3 cells to these antibodies results in a dose-dependent decrease in viable cells after 72 hours in culture. The chimeric version of A3 also is neutralizing. Antibody MH9A1, on the other hand, does not neutralize IL-9 because it exhibits no effect on TS1-RA3 cell viability.

EXAMPLE 2

Humanization by Rational Design Homology Matching

For both MH9A3 and MH9D1, the variable regions of the heavy and light chains are aligned against the NCBI human germline database. Frameworks that best matched the donor sequence (homology matching) and retain the maximum number of key canonical residues (functional matching) are identified. Humanization is carried out using a PCR-based mutagenesis approach (PCR by overlap extension) and standard protocols to introduce the necessary changes into the murine sequence (See FIGS. 6-9).

The following oligonucleotides are used:

For the Humanization of the MH9A3 Light Chain into Germline B3:

```
5'GCAGCCACAGCCCGTTTGATCTCGACCTTGGTCCCACCACCGAACGTGAGAG      (SEQ ID NO: 41)
GATAGCTGTA-3'

5'TTCACTCTCACCATCAGTAGTTTGCAGGCTGAAGACGTGGCAGTGTATTACT      (SEQ ID NO: 42)
GTCAGCAATTTTAC-3'

5'GTAAAATTGCTGACAGTAATACACTGCCACGTCTTCAGCCTGCAAACTACTG      (SEQ ID NO: 43)
ATGGTGAGAGTGAA-3'

5'-CCCTGATCGCTTCAGTGGCAGTGGATC-3'                           (SEQ ID NO: 44)

5'-GATCCACTGCCACTGAAGCGATCAGGG-3'                           (SEQ ID NO: 45)

5'-CAGAAACCAGGGCAACCCCCTAAACTGCTGATTTACTCG-3'               (SEQ ID NO: 46)

5'-CGAGTAAATCAGCAGTTTAGGGGGTTGCCCTGGTTTCTG-3'               (SEQ ID NO: 47)

5'GTGATGACCCAGTCTCCCGACAGCCTGGCTGTCTCACTGGGAGAGAGGGCT      (SEQ ID NO: 48)
ACCATCAATTGCAAGGCCAGTCAG-3'

5'-TATATATATATATATACCCCGGGGCCAAATGTGACATTGTGATGACCCAGTCTC-3' (SEQ ID NO: 49)
```

-continued

5'GCAGCCACCGTACGTTTGATCTCGACCTTGGTCCCACCACCGAACGTGAGAG GATAGCT-3' (SEQ ID NO: 50)

For the Humanization of the MH9A3 Heavy Chain into Germline 1-69:

5'-CTCAGCAGCCTGCGCTCTGAGGACACAGCCGTCTATTACTGTGCAAGAGCG-3' (SEQ ID NO: 51)

5'-GGAGGCTGAGGAGACTGTGACCAGGGTGCTTGGCCCCAG-3' (SEQ ID NO: 52)

5'CGCTCTTGCACAGTAATAGACGGCTGTGTCCTCAGAGCGCAGGCTGCTGAG-3' (SEQ ID NO: 53)

5'GAGAAGTTCAAGGGCCGCGTCACAATCACAGCAGATAAATCCACATCTACA GCCTACATGGAACTCAGC-3' (SEQ ID NO: 54)

5'GCTGAGTTCCATGTAGGCTGTAGATGTGGATTTATCTGCTGTGATTGTGACG CGGCCCTTGAACTTCTC-3' (SEQ ID NO: 55)

5'CTGGATAGAGTGGGTCCGCCAGGCTCCTGGACAGGGCCTTGAGTGGATGGG AGAGATTTTACC-3' (SEQ ID NO: 56)

5'GGTAAAATCTCTCCCATCCACTCAAGGCCCTGTCCAGGAGCCTGGCGGACCC ACTCTATCCAG-3' (SEQ ID NO: 57)

5'TCTGGAGCTGAGGTCAAAAAGCCTGGGTCTTCAGTGAAGGTCTCCTGCAAG GCTTCTGGCTACACATTC-3' (SEQ ID NO: 58)

5'GAATGTGTAGCCAGAAGCCTTGCAGGAGACCTTCACTGAAGACCCAGGCTT TTTGACCTCAGCTCCAGA-3' (SEQ ID NO: 59)

5'-AAGCTTGTTGACTAGTGAGATC-3' (SEQ ID NO: 60)

5'TATATATATATAGGGCCCTTGGTGGAGGCTGAGGAGACTGTGACCAGGGTG CCTTGGCCCC-3' (SEQ ID NO: 61)

5'-CAGGTTCAGCTGGTCCAGTCTGGAGCTGAG-3' (SEQ ID NO: 62)

5'-CTCAGCTCCAGACTGGACCAGCTGAACCTG-3' (SEQ ID NO: 63)

For the Humanization of the MH9A3 Heavy Chain into Germline 5-51:

5'TATATATATATAGGGCCCTTGGTGGAGGCTGAGGAGACTGTGACCAGGGTG CCTTGGCCCC-3' (SEQ ID NO: 64)

5'-AGCAGCCTGAAAGCTTCTGACACAGCCATGTATTACTGTGCAAGAGCG-3' (SEQ IQ NO: 65)

5'-CGCTCTTGCACAGTAATACATGGCTGTGTCAGAAGCTTTCAGGCTGCT-3' (SEQ ID NO: 66)

5'AAGTTCAAGGGCCAGGTCACAATCTCTGCAGATAAATCCATCTCTACAGCCT ACCTGCAATGGAGCAGCCTG-3' (SEQ ID NO: 67)

5'CAGGCTGCTCCATTGCAGGTAGGCTGTAGAGATGGATTTATCTGCAGAGATT GTGACCTGGCCCTTGAACTT-3' (SEQ ID NO: 68)

5'CTGGATAGAGTGGGTCCGCCAGATGCCTGGAAAAGGCCTTGAGTGGATGGG AGAGATTTTACC-3' (SEQ ID NO; 69)

5'GGTAAAATCTCTCCCATCCACTCAAGGCCTTTTCCAGGCATCTGGCGGACCC ACTCTATCCAG-3' (SEQ ID NO: 70)

5'TCTGGAGCTGAGGTCAAAAAGCCTGGGGAATCACTGAAGATCTCCTGCAAG GGGTCTGGCTACACATTC-3' (SEQ ID NO: 71)

5'GAATGTGTAGCCAGACCCCTTGCAGGAGATCTTCAGTGATTCCCCAGGCTTT TTGACCTCAGCTCCAGA-3' (SEQ ID NO: 72)

5'-AAGCTTGTTGACTAGTGAGATC-3' (SEQ ID NO: 73)

5'-GGTGTCCACTCCGAAGTTCAGCTGGTCCAGTCTGGAGCT-3' (SEQ ID NO: 74)

5'-AGCTCCAGACTGGACCAGCTGAACTTCGGAGTGGACACC-3' (SEQ ID NO: 75)

For the Humanization of the MH9D1 Light Chain into Germline L1:

5'TGGCTCCCCGGGGCCAAATGTGACATCCAGATGACCCAGTCTCCATCCTCAC  (SEQ ID NO: 76)
TGTCTGCATCTGTAGG-3'

5'GCAAGTCAGGACATTGGCAGTAATATAGGGTGGTTTCAGCAGAAACCAGGG  (SEQ ID NO: 77)
AAAGCCCC-3'

5'GGATCCAATTTGGAAGATGGGGTCCCATCAAGGTTCAGCGGCAGTGGATCT  (SEQ ID NO: 78)
GGGACAGATTTCACTCTCACC-3'

5'-TACTGCGTACAGTTTGCTCAGTTTCCGTACACTTTTGGCCAGGGG-3'  (SEQ ID NO: 79)

5'CTGCCAATGTCCTGACTTGCATGACAAGTGATGGTGACTCTGTCTCCTACAG  (SEQ ID NO: 80)
ATGCAGACAGTGAGG-3'

5'ATCTTCCAAATTGGATCCATGATAGATCAGGGACTTAGGGGCTTTCCCTGGT  (SEQ ID NO: 81)
TTCTGC-3'

5'GCAAACTGTACGCAGTAATAAGTGCAAAATCTTCAGGCTGCAGGCTGCTG  (SEQ ID NO: 82)
ATGGTGAGAGTGAAATCTGTCCC-3'

5'-GCCACCGTACGTTTGATCTCCAGCTTGGTCCCCTGGCCAAAAGTGTACGG-  (SEQ ID NO: 83)
3'

For the Humanization of the MH9D1 Heavy Chain into Germline VH 1-69:

5'TTGAGGTCTAGACATATATATGGGTGACAATGACATCCACTTTGCCTTTCTCT(SEQ ID NO: 84)
CCACAGGTGTCCACTCC-3'

5'GAAGAAGCCTGGGTCCTCGGTGAAGGTCTCCTGCAAGGCTTCTGGAGGCAC  (SEQ ID NO: 85)
CTTCAGCAACTACTACATAGGTTGGG-3'

5'GGAGATATTTACCCTGGAAGTACTTATATTAACTACAATGAGAAGTTCAAGG  (SEQ ID NO: 86)
GCAGAGTCACG-3'

5'GAGCTGAGCAGCCTGAGATCTGAGGACACGGCCGTGTATTACTGTGCGAGA  (SEQ ID NO: 87)
TCGGATGATGGTTACTACGGGTTTCC-3'

5'CGAGGACCCAGGCTTCTTCACCTCAGCCCCAGACTGCACCAGCTGCACCTGG  (SEQ ID NO: 88)
GAGTGGACACCTGTGG-3'

5'AGGGTAAATATCTCCCATCCACTCAAGCCCTTGTCCAGGGGCCTGTCGCACC  (SEQ ID NO: 89)
CAACCTATGTAGTAG-3'

5'TCAGGCTGCTCAGCTCCATGTAGGCTGTGCTCGTGGATTTGTCCGCGGTAAT  (SEQ ID NO: 90)
CGTGACTCTGCCCTTG-3'

5'ACCGATGGGCCCTTGGTGGAGGCTGAAGAGACAGTGACCAGAGTCCCTTGG  (SEQ ID NO: 91)
CCCCAGTAAGGAAACCCGTAGTAACC-3'

For the Humanization of the MH9D1 Heavy Chain into Germline VH 3-21:

5'CTTGAGGTCTAGACATATATATGGGTGACAATGACATCCACTTTGCCTTTCT  (SEQ ID NO: 92)
CTCCACAGGTGTCCACTCCG-3'

5'GGGGGGTCCCTGAGACTCTCCTGTGCAGCCTCTGGATTCACCTTCAGTAACT  (SEQ ID NO: 93)
ACTACATAGGTTGGGTCCGCCAGG-3'

5'GGAAGTACTTATATTAACTACAATGAGAAGTTCAAGGGCCGATTCACCATCT  (SEQ ID NO: 94)
CCAGAGACAACGCCAAGAAC-3'

5'CGGCTGTGTATTACTGTGCGAGATCGGATGATGGTTACTACGGGTTTCCTTA  (SEQ ID NO: 95)
CTGGGGC-3'

5'TCTCAGGGACCCCCCAGGCTTGACCAGGCCTCCCCCAGACTCCACCAGCTGC  (SEQ ID NO: 96)
ACCTCGGAGTGGACACCTGTGG-3'

5'AATATAAGTACTTCCAGGGTAAATATCTGAGACCCACTCCAGCCCCTTCCCT  (SEQ ID NO: 97)
GGAGCCTGGCGGACCCAACC-3'

-continued

5'CAGTAATACACAGCCGTGTCCTCGGCTCTCAGGCTGTTCATTTGCAGATACA GTGAGTTCTTGGCGTTGTCTC-3' (SEQ ID NO: 98)

5'GACCGATGGGCCCTTGGTGGAGGCTGAAGAGACAGTGACCAGAGTCCCTTG GCCCCAGTAAGGAAACCCG-3' (SEQ ID NO: 99)

For each MH9A3 and MH9D1, two humanized versions with different heavy/light chain pairing are generated and tested for activity: For MH9A3: VH1-69/B3 and VH5-51/B3 and for MH9D1: VH1-69/L1 and VH3-21/L1

The different constructions are transfected into 293 cells, purified on protein A columns and tested for activity using the TS1-RA3 neutralization assay. Humanized versions based on initial homology matching reduce the neutralizing activity of the original and chimeric antibodies. For instance, as shown in FIG. 10, 1-69/B3 (169B3) does not neutralize IL-9-dependent TS1-RA3 growth, and shows similar activity to the non-neutralizing antibody MH9A1. Further fine-tuning of the antibody sequence results in recovery of some neutralizing activity.

Fine-Tuning Optimization of Humanized Antibodies Based on Homology Matching

B3 is a fully humanized light chain but it leads to loss of binding/activity (see FIG. 10). Therefore, to enhance binding activity the light chain is "fine tuned". Several new constructs are designed having the light chain sequences shown in FIG. 11 (SEQ ID NOs: 18-25), as compared to original MH9A3 chimeric and MH9A3 (B3) humanized versions. As can bee seen from the in vitro inhibition results in FIG. 12. As shown in FIG. 12, FRII and L46A constructs in particular shows increased neutralizing activity. Moreover, as also shown in FIG. 12, the FRII construct (which contains the light chain sequence of SEQ ID NO: 19 matched to the heavy chain sequence of A3) shows neutralizing activity approaching that of the original MH9A3 antibody.

Humanization by Phage Display

This approach was designed after the method of Rader et al., *Proc. Natl. Acad. Sci. USA* 95, 1998, 8910-8915 and was applied to the A3 anti-IL9 inhibitory monoclonal antibody.

A—Cloning of MH9A3 into a Phagemid Vector

A scFv version of MH9A3 is cloned into the pCANTAB5E phagemid vector (Pharmacia, APB Biotech) (see FIG. 13) as a SfiI/NotI fragment using standard PCR protocols (PCR by overlap extension) and the following oligonucleotides (SfiI and NotI sites underlined):

B—Heavy and Light Chains Library Construction

Light Chain

I (a)—Inactivation of the MH9A3 Light Chains.

The MH9A3 light chain was mutagenized by introduction of 2 stop codons using the QuikChange XL site-directed mutagenesis kit from Stratagene and the following oligonucleotides:

(SEQ ID NO: 104)
5'-ACCTGGTATCAACAGTAATAAGGGCAATCTCCTAAAG-3'

(SEQ ID NO: 104)
5'-CTTTAGGAGATTGCCCTTATTACTGTTGATACCAGGT-3'

The construction generated is named pCANTAB5E/A3VH-A3VL(TAA) thereafter.

I (b)—Construction of a Library of Human Germline Light Chains.

Total RNA is extracted from human bone marrow (Poietic technology) as follows: 2.5 ml of marrow was transferred into a PAXgene Blood RNA tube (PreAnalytiX, Inc.), mixed gently and incubated for more than two hours at room temperature. Total RNA is extracted exactly as described in the PAXgene Blood RNA Kit handbook. First strand cDNA is synthesized using SuperScript First-Strand Synthesis System for RT-PCR (Invitrogen) with oligo(dT) priming as described in the manufacturer's manual. The cDNA is then amplified using the oligonucleotides listed below:

5'TATATATATATATATATATA<u>GGCCCAGCCGGCC</u>CAGGTTCAGCTGCAGCAGT CTGGAGCTGAG-3' (SEQ ID NO: 100)

5'TATATATATATATATATATA<u>GCGGCCGC</u>AGCCCGTTTCAGCTCCAGCTTGGT CCCAGC-3' (SEQ ID NO: 101)

5' GGTGGAGGCGGTTCAGGCGGAGGTGGCTCTGGCGGTGGCGGATCGGACATT GTGATGACCCAGTCTCAAAAATTC-3' (SEQ ID NO: 102)

5'CGATCCGCCACCGCCAGAGCCACCTCCGCCTGAACCGCCTCCACCTGAGGA GACTGTGAGAGTGGTGCCTTGGCCCC-3' (SEQ ID NO: 103)

```
5'-GCGGTGGCGGATCGGAGATCCAGWTGACCCAGTCTCC-3' Primer 1          (SEQ ID NO: 106)

5'-GCGGTGGCGGATCGGAGATCGTGATGACYCAGWCTCC-3' Primer 2          (SEQ ID NO: 107)

5'-GCGGTGGCGGATCGGAGATCGTGWTGACRCAGTCTCC-3' Primer 3          (SEQ ID NO: 108)

5'-GCGGTGGCGGATCGGAGATCACACTCACGCAGTCTCC-3' Primer 4          (SEQ ID NO: 109)

5'-CGTGAGAGGATAGCTGTAAAATTGCTGACAGTAATACACTGCAAAATCTC-3' Primer 5   (SEQ ID NO: 110)

5'-CGTGAGAGGATAGCTGTAAAATTGCTGACAGTAATAAACCCCARCATCCTC-3' Primer 6  (SEQ ID NO: 111)

5'-CGTGAGAGGATAGCTGTAAAATTGCTGACAGTAATAAGTTGCAAAATCTTC-3' Primer 7  (SEQ ID NO: 112)
```

Different combinations are used: 1/5, 1/6, 1/7, 2/5, 2/6, 2/7, 3/5, 3/6, 3/7, 4/5, 4/6 and 4/7. All amplifications are performed under standard PCR conditions using Platinum Taq DNA polymerase (Invitrogen) and annealing temperature 55-60° C. Equal amounts (around 200 ng) of the different PCR products were mixed together to serve as template in a 5-cycle PCR reaction containing the following oligonucleotides (BSU36I and NotI restriction sites underlined):

```
5'TATATATATATATACCTCAGGTGGAGGCGGTTCAGGCGGAGGTGGCTCTGGC (SEQ ID NO: 113)
GGTGGCGGATCGGAG-3'

5'TATATATATATATAGCGGCCGCAGCCCGTTTGATCTCCAGCTTGGTCCCCTG (SEQ ID NO: 114)
ACCGAACGTGAGAGGATAGCTGTA-3'
```

About 8 μg of pCANTAB5E/A3VH-A3VL(TAA) and 1.5 μg of mixed PCR products are digested with BSU36I and NotI and purified using the QIAquick gel purification kit (Qiagen). 5 μg of digested pCANTAB5E/A3VH-A3VL (TAA) and 1 μg of digested PCR products are set up for ligation for 18 hours at 15° C. using 4000 units of T4 DNA ligase (NEB) in a final volume of 100 μl. The ligation product is purified using the QIAquick gel purification kit (Qiagen) and eluted in 50 μl of water (pH 8.0). The mixture is transformed into TG1 electrocompetent cells (in 5 μl aliquot/200 μl competent TG1) in a 2.5 kV field using 200Ω resistance and 25 μF capacitance. After each electroporation, cells are resuspended in 2 ml ice cold SOC medium and added to 50 ml SOC medium (Invitrogen). After incubation for 45 nm at 37° C. with gentle shaking, cells are pelleted by centrifugation at 3 Krpm for 25 nm, resuspended in 500 ml of 2×YT medium containing 100 μg/ml ampicilin and 75 μl of helper phage (around $10^{11}$ pfu) and incubated at 37° C. with shaking overnight. Library diversity is estimated by titration of transformed cells immediately after electroporation on LB plates containing $100^{11}$ μg/ml ampicilin. Diversity up to $1\times10^7$ is achieved.

II—Heavy Chain.

II (a)—Inactivation of the MH9A3 Heavy Chain.

The MH9A3 heavy chain is mutagenized by introduction of 2 stop codons using the QuikChange XL site-directed mutagenesis kit from Stratagene and the following oligonucleotides:

```
                                            (SEQ ID NO: 115)
   5'-CTTGAGTGGCTTGGATAATAATTACCTGGAAGTGGT-3'

(SEQ ID NO: 116)
   5'-ACCACTTCCAGGTAATTATTATCCAAGCCACTCAAG-3'
```

A phagemid containing the inactivated heavy chain and the light chain identified after panning of the light chain library is then constructed. The construction generated is named pCANTAB5E/A3VH(TAA)-VL(Germ) thereafter.

II (b)—Construction of the Library of Human Germline Heavy Chains.

This library is constructed essentially as described in section IIa using the oligonucleotides listed below:

```
5'-TATATATATATAGGCCCAGCCGGCCCAGRTGCAGCTGGTGCAGTCTGG-3' Primer 1    (SEQ ID NO: 117)

5'-TATATATATATAGGCCCAGCCGGCCCAGATCACCTTGAAGGAGTCTGG-3' Primer 2    (SEQ ID NO: 118)

5'-TATATATATATAGGCCCAGCCGGCCGAGGTGCAGCTGKTGSAGTCTGG-3' Primer 3    (SEQ ID NO: 119)

5'-TATATATATATAGGCCCAGCCGGCCCAGGTGCAGCTGCAGGAGTCGGG-3' Primer 4    (SEQ ID NO: 120)

5'-GACGTAACTACTACCGTAGTAATCCGCTCTCGCACAGTAATACADGGCCYTGTC-3' Primer 5  (SEQ ID NO: 121)
```

Different combinations were used: 1/5, 2/5, 3/5 and 4/5. All amplifications are performed under standard PCR conditions using Platinum Taq DNA polymerase (Invitrogen) and annealing temperature 55-60° C. Equal amounts (around 200 ng) of the different PCR products are mixed together to serve as template in a 5-cycle PCR reaction containing the following oligonucleotides (SfiI and StyI restriction sites underlined):

```
5'-TATATATATATAGGCCCAGCCGGCC-3'                                    (SEQ ID NO: 122)

5'TATATATATATATACCTTGGCCCCAGTAGTCAAACTTGACGTAACTACTACCGTAGTA-3'   (SEQ ID NO: 123)
```

About 8 μg of pCANTAB5E/A3VH(TAA)-A3VL(Germ) and 1.5% g of mixed PCR products are digested with SfiI and StyI and purified using the QIAquick gel purification kit (Qiagen). 5 μg of digested pCANTAB5E/A3VH(TAA)-A3VL(Germ) and 1 μg of digested PCR products are set up for ligation for 18 hours at 15° C. using 4000 units of T4 DNA ligase (NEB) in a final volume of 100 μl. Electroporation of the library is then performed essentially as described in section IIb.

C—Panning of the Libraries.

Figure 14:
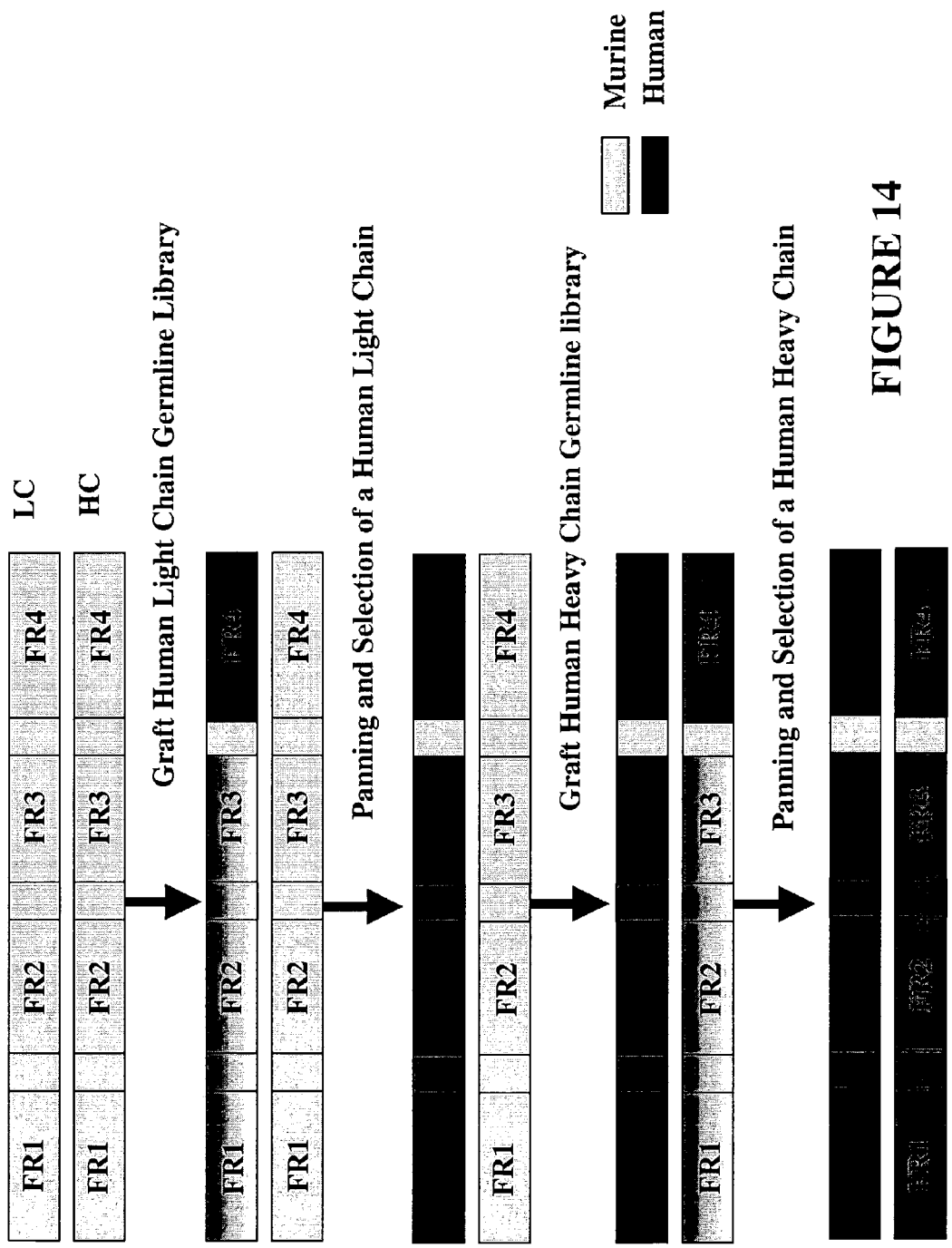
FIG. 14 contains a schematic that depicts the grafting and panning process used in the phage display technique.
Figure 16:
FIG. 16 contains a comparison of sequences of CDR regions from original MH9A3 chimeric heavy chain (SEQ ID NO: 3), derived from MH9A3 heavy chain humanized versions VH1-69 (SEQ ID NO: 7) and VH5-51 (SEQ ID NO: 8), CDR regions from MH9A3 chimeric light chain (SEQ ID NO: 5), MH9A3 light chain humanized version B3 (SEQ ID NO: 11), MH9A3 rational design optimized humanized light chain versions FRII (SEQ ID NO: 20) and L46A (SEQ ID NO: 24), and MH9A3 humanized light chain versions V12 (SEQ ID NO: 29) and L2 (SEQ ID NO: 32) obtained by phage display panning.

Libraries are screened as follows. Typically, 100 μl of a 100 ng/μl solution of the non-inhibitory anti-IL9 antibody A4 is added to 24 individual wells of a 96-wellmicrotiter plate and incubated overnight at 4° C. in PBS buffer. Wells are washed with 250 μl of PBS 3 times and blocked with 250 μl of PBS/3% milk for 2 h at 37° C. 100 μl of a 0.2 ng/μl solution of recombinant human IL9 (R & D) is then added to each well. After incubation for 1 h at room temperature, wells are washed with 250 μl of PBS 3 times. 100 μl of recombinant phage (about $10^{11}$ pfu) in PBS/4% milk/0.1% tween 20 are added to each well and incubated for 90-120 nm at room temperature under agitation. Wells were washed 10 times with PBS and 10 times with PBS containing 0.1% Tween 20 for the first round of panning. Number of washes are increased up to 15 and 20 times for the second and third round of panning, respectively. Exponentially growing TG1 E. coli cells are added (200 μl cells/well) to the wells and incubated for 1 hour at 37° C. Infected cells are transferred to 200 ml of 2×YT medium supplemented with 100 μg/ml ampicillin/$10^{11}$ pfu of VCSM13 helper phage and incubated overnight at 37° C. After electroporation and each round of panning, phage are precipitated with 20% PEG 8000/5M NaCl (1/5 v/v) and resuspended in 5 ml PBS/0.1% tween 20. A diagram of the panning process is shown in FIG. 14. The sequences of seven different A3 light chains (SEQ ID NOs: 26-32) obtained after three rounds of panning are shown in FIG. 16. For comparison purposes, an alignment of the original MH9A3 light chain, the humanized version B3, the optimized humanized versions FRII and L46A, and the phage display-derived versions V12 and L2, is provided in FIG. 16

EXAMPLE 3

Isolation, Chimerization and Characterization of MH9L1 Anti-Human IL-9 Antibody

Isolation of Neutralizing Murine Anti-Human IL-9 Antibodies

SJL mice are immunized with Baculovirus-expressed recombinant IL-9 purchased from R+D Systems, complexed with Ovalbumin from Sigma. A neutralizing antibody (MH9L1) is generated using a commercially-available adjuvant called ImmuneEasy (Qiagen). Sera and monoclonal antibodies derived from immunized mice were screened first in an ELISA assay for reactivity with the R+D Systems recombinant human IL-9. Positive sera and mAbs are subsequently tested for in vitro neutralization activity by testing the antibodies for the ability to inhibit TS1-RA3 proliferation as described below.

Production of Chimeric Antibodies

Using the MH9L1 murine antibody, chimeras are constructed using the Cγ1 Synagis and Cκ Synagis by grafting the variable region sequences onto a human IgG1 constant background (Synagis). Cloning is carried out using standard PCR protocols. XmaI/BsiWI and XbaI/ApaI restriction sites are used for cloning the light and heavy chains, respectively, into the expression vectors.

MH9L1 derived chimeras are transfected into 293 cells, purified on protein A columns and tested for activity using the in vitro neutralization assay described below. Amino acid sequences of the CDR regions of the heavy chains of the MH9L1 are shown in FIG. 3. Amino acid sequences of the CDR regions of the light chain MH9L1 of the antibody are shown in FIG. 4.

In Vitro Neutralization Assay

TS1-RA3 was developed at the Ludwig Institute. It is a murine T cell line, TS1 that has been genetically modified to overexpress the human IL9 receptor alpha (IL9Ra). The resulting cell line, TS1-RA3, is absolutely dependent on recombinant human IL9 for its growth. To test the effectiveness of anti-IL9 antibodies, we grow TS1-RA3 cells in a known concentration of recombinant IL9, in the presence of anti-IL9 antibodies. If the anti-IL9 antibody is neutralizing, we observe that the TS1-RA3 cells die over a period of 48 to 72 hours. Non-neutralizing antibodies have no effect on TS1-RA3 growth.

Figure 19:
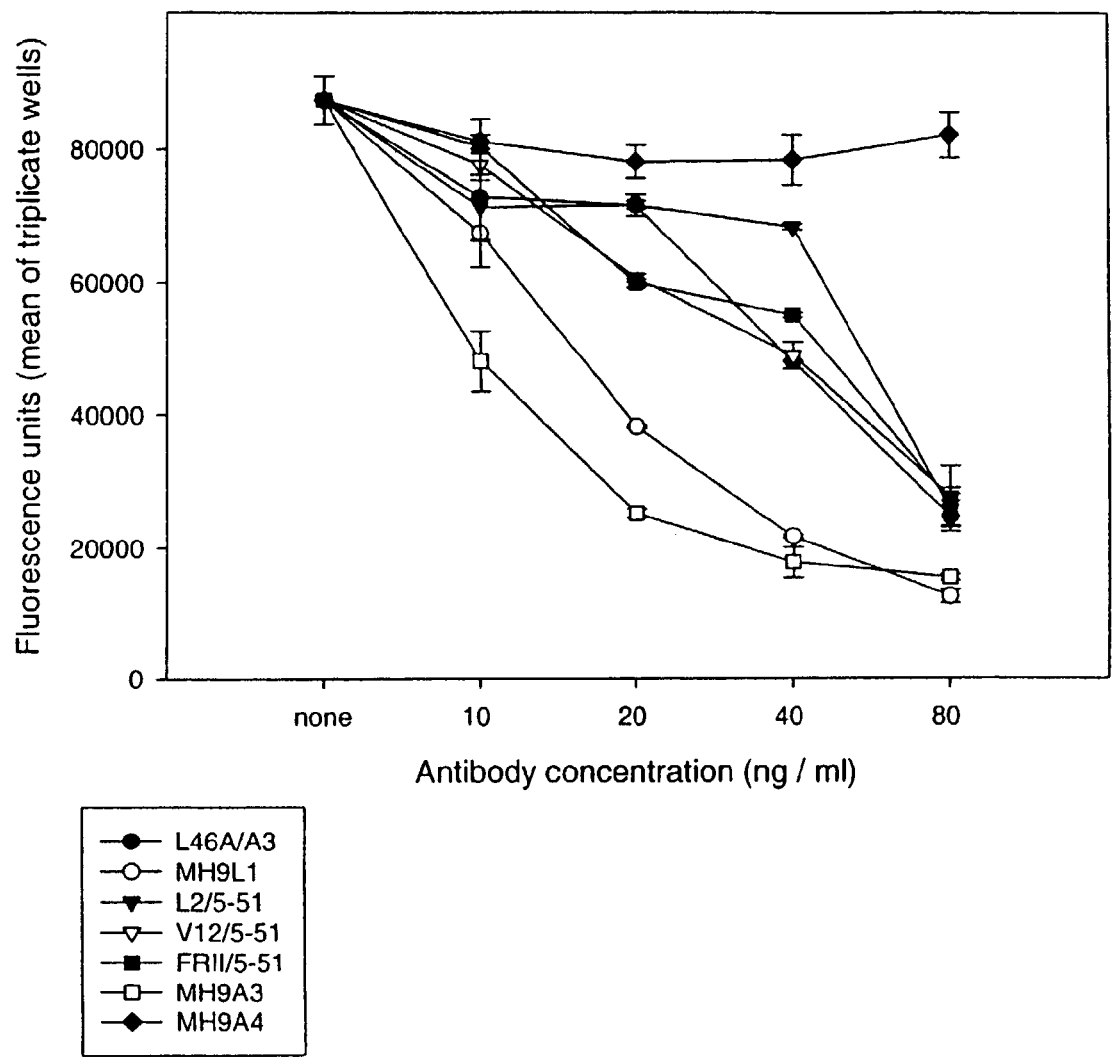
FIG. 19 contains a graph containing data that compares the ability of various anti-IL9 antibodies to inhibit TS1-RA3 proliferation, including MH9L1 and MH9A3.

Upon exposure of TS1-RA3 cells to MH9L1. Using this assay system, MH9L1 is found to neutralize IL-9 activity (See FIG. 19). This neutralization activity is observed in a dose-dependent decrease in viable cells after 72 hours in culture. The chimeric version of MH9L1 is also neutralizing using this assay.

EXAMPLE 4

Humanization of Anti-Human IL-9 Antibodies

Humanization by Rational Design Homology Matching

The variable regions of the heavy and light chains of MH9L1 are aligned against the NCBI human germline database. Frameworks that best matched the donor sequence (homology matching) and retain the maximum number of key canonical residues (functional matching) are identified.

Humanization is carried out using a PCR-based mutagenesis approach (PCR by overlap extension) and standard protocols to introduce the necessary changes into the murine sequence. As shown in FIG. 17, the MH9L1 heavy chain shows substantial sequence identity to the human genomic heavy chain sequences VH1-69 and VH5-51. As shown in FIG. 18 and the MH9L1 light chain sequence shows substantial sequence identity to the human genomic sequences A26 and L15

Different constructions produced by the above-described method are transfected into 293 cells, purified on protein A columns and tested for activity using the TS1-RA3 neutralization assay. Humanized versions based on initial homology matching are evaluated for their neutralizing activity relative the original murine antibody and chimeric MH9L1 antibodies. Further fine-tuning of the antibody sequence will result in enhanced neutralizing activity.

Humanization by Phage Display

This approach was designed after the method of Rader et al., *Proc. Natl. Acad. Sci. USA* 95, 1998, 8910-8915 and is applied to the MH9L1 anti-human IL9 inhibitory monoclonal antibody.

A—Cloning of MH9L1 into a Phagemid Vector

Figure 13:
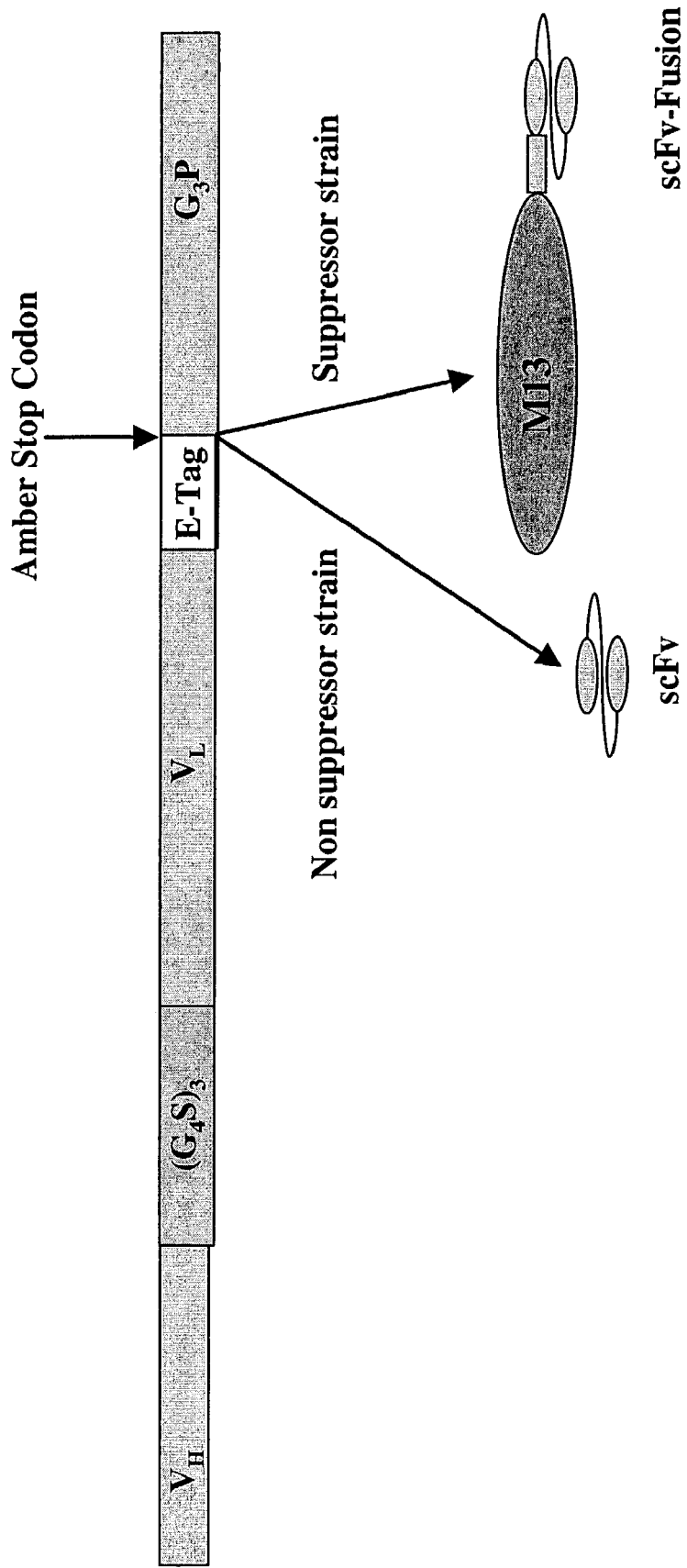
FIG. 13 contains a schematic that depicts the cloning of anti-IL-9 antibody sequences into the pCANTAB5E phagemid vector, showing the antibody cloned in single chain Fv format in frame with a tag (eTag) and the gene III coat protein of M13. Functional antibody fragments linked to the gene III coat protein are formed in a suppressor host strain and displayed on the surface of M13 by virtue of the leakiness of the amber stop codon located between scFV: E-Tag and gene III. In a non-suppressor strain, soluble scFv fragments are produced.

A scFv version of MH9L1 is cloned into the pCANTAB5E phagemid vector (Pharmacia, APB Biotech) (see FIG. 13) as a SfiI/NotI fragment using standard PCR protocols (PCR by overlap extension).

B—Heavy and Light Chains Library Construction

Light Chain

I (a)—Inactivation of the MH9L1 Light Chain.

The MH9L1 light chain is mutagenized by introduction of 2 stop codons using the QuikChange XL site-directed mutagenesis kit from Stratagene.

I (b)—Construction of a Library of Human Germline Light Chains.

Total RNA is extracted from human bone marrow (Poietic technology) as follows: 2.5 ml of marrow is transferred into a PAXgene Blood RNA tube (PreAnalytiX, Inc.), mixed gently and incubated for more than two hours at room temperature. Total RNA is extracted exactly as described in the PAXgene Blood RNA Kit handbook. First strand cDNA is synthesized using SuperScript First-Strand Synthesis System for RT-PCR (Invitrogen) with oligo(dT) priming as described in the manufacturer's manual. The cDNA is then amplified using the appropriate oligonucleotides listed below:

Amplifications are performed under standard PCR conditions using Platinum Taq DNA polymerase (Invitrogen) and annealing temperature 55-60° C. Equal amounts (around 200 ng) of the different PCR products are mixed together to serve as template in a 5-cycle PCR reaction containing the appropriate oligonucleotide The result mixed PCR products are digested with restriction enzymes and purified using the QIAquick gel purification kit (Qiagen). The digested PCR products are set up for ligation for 18 hours at 15° C. using 4000 units of T4 DNA ligase (NEB) in a final volume of 100 µl. The ligation product is purified using the QIAquick gel purification kit (Qiagen) and eluted in 50 µl of water (pH 8.0). Mixture is transformed into TG1 electrocompetent cells (in 5 µl aliquot/ 200 µl competent TG1) in a 2.5 kV field using 200Ω resistance and 25 µF capacitance. After each electroporation, cells are resuspended in 2 ml ice cold SOC medium and added to 50 ml SOC medium (Invitrogen). After incubation for 45 nm at 37° C. with gentle shaking, cells are pelleted by centrifugation at 3 Krpm for 25 nm, resuspended in 500 ml of 2×YT medium containing 100 µg/ml ampicilin and 75 µl of helper phage (around $10^{11}$ pfu) and incubated at 37° C. with shaking overnight. Library diversity is estimated by titration of transformed cells immediately after electroporation on LB plates containing 100 µg/ml ampicilin. Diversity up to $1 \times 10^7$ is obtained.

II—Heavy Chain.

IIa—Inactivation of the MH9L1 Heavy Chain.

The MH9L1 heavy chain is mutagenized by introduction of 2 stop codons using the QuikChange XL Site-Directed Mutagenesis Kit from Stratagene and Suitable Oligonucleotides:

II (b)—Construction of the Library of Human Germline Heavy Chains.

This library is constructed essentially as described in section IIa using suitable oligonucleotides.

Different combinations are used: 1/5, 2/5, 3/5 and 4/5. All amplifications are performed under standard PCR conditions using Platinum Taq DNA polymerase (Invitrogen) and annealing temperature 55-60° C. Equal amounts (around 200 ng) of the different PCR products are mixed together to serve as template in a 5-cycle PCR reaction containing suitable oligonucleotides, The result mixed PCR products are digested with appropriate restriction enzymes and purified using the QIAquick gel purification kit (Qiagen). 5 µg of digested PCR products are set up for ligation for 18 hours at 15° C. using 4000 units of T4 DNA ligase (NEB) in a final volume of 100 µl. Electroporation of the library is then performed essentially as described in section IIb.

C—Panning of the Libraries.

Libraries are screened as follows. Typically, 100 µl of a 100 ng/µl solution of the non-inhibitory anti-IL9 antibody MH9L1 is added to 24 individual wells of a 96-wellmicrotiter plate and incubated overnight at 4° C. in PBS buffer. Wells are washed with 250 µl of PBS 3 times and blocked with 250 µl of PBS/3% milk for 2 h at 37° C. 100 µl of a 0.2 ng/µl solution of recombinant human IL9 (R & D) is then added to each well. After incubation for 1 h at room temperature, wells are washed with 250 µl of PBS 3 times. 100 µl of recombinant phage (about $10^{11}$ pfu) in PBS/4% milk/0.1% tween 20 are added to each well and incubated for 90-120 nm at room temperature under agitation. Wells are washed 10 times with PBS and 10 times with PBS containing 0.1% Tween 20 for the first round of panning. Number of washes is increased up to 15 and 20 times for the second and third round of panning, respectively. Exponentially growing TG1 *E. coli* cells are added (200 µl cells/well) to the wells and incubated for 1 hour at 37° C. Infected cells are transferred to 200 ml of 2×YT medium supplemented with 100 µg/ml ampicillin/$10^{11}$ pfu of VCSM13 helper phage and incubated overnight at 37° C. After electroporation and each round of panning, phage are precipitated with 20% PEG 8000/5M NaCl (1/5 v/v) and resuspended in 5 ml PBS/0.1% tween 20. A diagram of the panning process is shown in FIG. 14.

SEQUENCE LISTING

<160> NUMBER OF SEQ ID NOS: 140

<210> SEQ ID NO 1
<211> LENGTH: 360
<212> TYPE: DNA
<213> ORGANISM: Homo sapiens

<400> SEQUENCE: 1
gacattgtga tgacccagtc tcaaaaattc atgcccacat cagtaggaga cagggtcagc    60
gtcacctgca aggccagtca gcatgtgggt actcatgtaa cctggtatca acagaaacca   120
gggcaatctc ctaaagcact gatttactcg acatcctacc ggtacagtgg agtccctgat   180
cgcttcacag gcagtggatc tgggacagat ttcactctca ccatcaccaa tgtgcagtct   240
gaagacttgg cagagtattt ctgtcagcaa ttttacagct atcctctcac gttcggtgct   300
gggaccaagc tggagctgaa acgggctgat gctgcaccaa ctgtatccat cttcccacca   360

<210> SEQ ID NO 2
<211> LENGTH: 366
<212> TYPE: DNA
<213> ORGANISM: Homo sapiens

<400> SEQUENCE: 2
caggttcagc tgcagcagtc tggagctgag ctgatgaagc ctggggacctc agtgaagctt    60
tcctgcaagg ctactggcta cacattcact ggctactgga tagagtggat aaagcggagg   120
cctggacatg gccttgagtg gcttggagag attttacctg gaagtggtac tactaactac   180
aatgagaagt tcaagggcaa ggccacattc cctgcagata catcctccaa cacagcctac   240
atgcaactca gcagcctgac aactgaggac tctgccatct attactgtgc aagagcggat   300
tactacggta gtagttacgt caagtttgac tactggggcc aaggcaccac tctcacagtc   360
tcctca                                                              366

<210> SEQ ID NO 3
<211> LENGTH: 122
<212> TYPE: PRT
<213> ORGANISM: Homo sapiens

<400> SEQUENCE: 3

Gln Val Gln Leu Gln Gln Ser Gly Ala Glu Leu Met Lys Pro Gly Thr
1               5                   10                  15

Ser Val Lys Leu Ser Cys Lys Ala Thr Gly Tyr Thr Phe Thr Gly Tyr
            20                  25                  30

Trp Ile Glu Trp Ile Lys Arg Arg Pro Gly His Gly Leu Glu Trp Leu
        35                  40                  45

Gly Glu Ile Leu Pro Gly Ser Gly Thr Thr Asn Tyr Asn Glu Lys Phe
    50                  55                  60

Lys Gly Lys Ala Thr Phe Pro Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Ala Asp Tyr Tyr Gly Ser Ser Tyr Val Lys Phe Asp Tyr Trp
            100                 105                 110

Gly Gln Gly Thr Thr Leu Thr Val Ser Ser
        115                 120

-continued

<210> SEQ ID NO 4
<211> LENGTH: 88
<212> TYPE: PRT
<213> ORGANISM: Homo sapiens

<400> SEQUENCE: 4

Val Ser Gly Ala Val Arg Gly Thr Ser Val Lys Met Ser Cys Lys Ala
1               5                   10                  15

Ser Gly Thr Thr Asn Tyr Tyr Gly Trp Ala Lys Arg Gly His Gly Trp
            20                  25                  30

Gly Asp Tyr Gly Ser Thr Tyr Asn Tyr Asn Lys Lys Gly Lys Ala Thr
        35                  40                  45

Thr Ala Asp Lys Ser Ser Thr Ala Tyr Met Ser Ser Thr Ser Asp
50                  55                  60

Ser Ala Tyr Tyr Cys Ala Arg Ser Asp Asp Gly Tyr Tyr Gly Tyr Trp
65                  70                  75                  80

Gly Gly Thr Val Thr Val Ser Ala
                85

<210> SEQ ID NO 5
<211> LENGTH: 120
<212> TYPE: PRT
<213> ORGANISM: Homo sapiens

<400> SEQUENCE: 5

Asp Ile Val Met Thr Gln Ser Gln Lys Phe Met Pro Thr Ser Val Gly
1               5                   10                  15

Asp Arg Val Ser Val Thr Cys Lys Ala Ser Gln His Val Gly Thr His
            20                  25                  30

Val Thr Trp Tyr Gln Gln Lys Pro Gly Gln Ser Pro Lys Ala Leu Ile
        35                  40                  45

Tyr Ser Thr Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Phe Tyr Ser Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro
        115                 120

<210> SEQ ID NO 6
<211> LENGTH: 108
<212> TYPE: PRT
<213> ORGANISM: Homo sapiens

<400> SEQUENCE: 6

Asp Ile Leu Met Thr Gln Ser Pro Ser Ser Met Ser Val Ser Leu Gly
1               5                   10                  15

Asp Thr Val Ser Ile Thr Cys His Ala Ser Gln Asp Ile Gly Ser Asn
            20                  25                  30

Ile Gly Trp Leu Gln Gln Lys Pro Gly Lys Ser Phe Lys Gly Leu Ile
        35                  40                  45

Tyr His Gly Ser Asn Leu Glu Asp Gly Val Pro Ser Arg Phe Ser Gly
    50                  55                  60

Ser Gly Ser Gly Ala Asp Tyr Ser Leu Thr Ile Asn Ser Leu Glu Ser
65                  70                  75                  80

```
Glu Asp Phe Ala Asp Tyr Tyr Cys Val Gln Phe Ala Gln Phe Pro Tyr
                85                  90                  95

Thr Phe Gly Gly Gly Thr Lys Leu Glu Met Lys Arg
            100                 105

<210> SEQ ID NO 7
<211> LENGTH: 87
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Trp Val
            20                  25                  30

Arg Gln Ala Pro Gly Gln Gly Leu Glu Trp Met Gly Arg Val Thr Ile
        35                  40                  45

Thr Ala Asp Lys Ser Thr Ser Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 8
<211> LENGTH: 122
<212> TYPE: PRT
<213> ORGANISM: Homo sapiens

<400> SEQUENCE: 8

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Gly Tyr
            20                  25                  30

Trp Ile Glu Trp Val Arg Gln Met Pro Gly Lys Gly Leu Glu Trp Met
        35                  40                  45

Gly Glu Ile Leu Pro Gly Ser Gly Thr Thr Asn Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Ala Asp Tyr Tyr Gly Ser Ser Tyr Val Lys Phe Asp Tyr Trp
            100                 105                 110

Gly Gln Gly Thr Leu Val Thr Val Ser Ser
        115                 120

<210> SEQ ID NO 9
<211> LENGTH: 119
<212> TYPE: PRT
<213> ORGANISM: Homo sapiens

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asn Tyr
            20                  25                  30
```

Tyr Ile Gly Trp Val Arg Gln Ala Pro Gly Gln Gly Leu Glu Trp Met
            35                  40                  45

Gly Asp Ile Tyr Pro Gly Ser Thr Tyr Ile Asn Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Asp Gly Tyr Tyr Gly Phe Pro Tyr Trp Gly Gln Gly
                100                 105                 110

Thr Leu Val Thr Val Ser Ser
            115

<210> SEQ ID NO 10
<211> LENGTH: 119
<212> TYPE: PRT
<213> ORGANISM: Homo sapiens

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Tyr
            20                  25                  30

Tyr Ile Gly Trp Val Arg Gln Ala Pro Gly Lys Gly Leu Glu Trp Val
            35                  40                  45

Ser Asp Ile Tyr Pro Gly Ser Thr Tyr Ile Asn Tyr Asn Glu Lys Phe
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asp Asp Gly Tyr Tyr Gly Phe Pro Tyr Trp Gly Gln Gly
                100                 105                 110

Thr Leu Val Thr Val Ser Ser
            115

<210> SEQ ID NO 11
<211> LENGTH: 107
<212> TYPE: PRT
<213> ORGANISM: Homo sapiens

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr His
            20                  25                  30

Val Thr Trp Tyr Gln Gln Lys Pro Gly Gln Pro Pro Lys Leu Leu Ile
            35                  40                  45

Tyr Ser Thr Ser Tyr Arg Tyr Ser Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Phe Tyr Ser Tyr Pro Leu
                85                  90                  95

Thr Phe Gly Gly Gly Thr Lys Val Glu Ile Lys
            100                 105

```
<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Gly Ser Asn
            20                  25                  30

Ile Gly Trp Phe Gln Gln Lys Pro Gly Lys Ala Pro Lys Ser Leu Ile
        35                  40                  45

Tyr His Gly Ser Asn Leu Glu Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Phe Ala Gln Phe Pro Tyr
                85                  90                  95

Thr Phe Gly Gln Gly Thr Lys Leu Glu Ile Lys
            100                 105

<210> SEQ ID NO 13
<211> LENGTH: 122
<212> TYPE: PRT
<213> ORGANISM: Homo sapiens

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Thr Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Asp Tyr Tyr Gly Ser Ser Tyr Val Lys Phe Asp Tyr Trp
            100                 105                 110

Gly Gln Gly Thr Leu Val Thr Val Ser Ser
        115                 120

<210> SEQ ID NO 14
<211> LENGTH: 122
<212> TYPE: PRT
<213> ORGANISM: Homo sapiens

<400> SEQUENCE: 14

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Gly Tyr
            20                  25                  30

Trp Ile Glu Trp Val Arg Gln Met Pro Gly Lys Gly Leu Glu Trp Met
        35                  40                  45

Gly Glu Ile Leu Pro Gly Ser Gly Thr Thr Asn Tyr Asn Glu Lys Phe
```

```
              50                  55                  60
Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ala Asp Tyr Tyr Gly Ser Ser Tyr Val Lys Phe Asp Tyr Trp
                100                 105                 110

Gly Gln Gly Thr Leu Val Thr Val Ser Ser
            115                 120

<210> SEQ ID NO 15
<211> LENGTH: 119
<212> TYPE: PRT
<213> ORGANISM: Homo sapiens

<400> SEQUENCE: 15

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Thr Phe Thr Asn Tyr
                 20                  25                  30

Tyr Ile Gly Trp Val Arg Gln Ala Pro Gly Gln Gly Leu Glu Trp Met
             35                  40                  45

Gly Asp Ile Tyr Pro Gly Ser Thr Tyr Ile Asn Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Asp Asp Gly Tyr Tyr Gly Phe Pro Tyr Trp Gly Gln Gly
                100                 105                 110

Thr Leu Val Thr Val Ser Ser
            115

<210> SEQ ID NO 16
<211> LENGTH: 119
<212> TYPE: PRT
<213> ORGANISM: Homo sapiens

<400> SEQUENCE: 16

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Thr Asn Tyr
                 20                  25                  30

Tyr Ile Gly Trp Val Arg Gln Ala Pro Gly Lys Gly Leu Glu Trp Val
             35                  40                  45

Ser Asp Ile Tyr Pro Gly Ser Thr Tyr Ile Asn Tyr Asn Glu Lys Phe
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Asp Asp Gly Tyr Tyr Gly Phe Pro Tyr Trp Gly Gln Gly
                100                 105                 110

Thr Leu Val Thr Val Ser Ser
            115
```

-continued

<210> SEQ ID NO 17

<400> SEQUENCE: 17

000

<210> SEQ ID NO 18
<211> LENGTH: 107
<212> TYPE: PRT
<213> ORGANISM: Homo sapiens

<400> SEQUENCE: 18

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr His
            20                  25                  30

Val Thr Trp Tyr Gln Gln Lys Pro Gly Gln Pro Pro Lys Leu Leu Ile
        35                  40                  45

Tyr Ser Thr Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Phe Tyr Ser Tyr Pro Leu
                85                  90                  95

Thr Phe Gly Gly Gly Thr Lys Val Glu Ile Lys
            100                 105
```

<210> SEQ ID NO 19
<211> LENGTH: 107
<212> TYPE: PRT
<213> ORGANISM: Homo sapiens

<400> SEQUENCE: 19

```
Asp Ile Val Met Thr Gln Ser Gln Lys Phe Met Pro Thr Ser Val Gly
1               5                   10                  15

Asp Arg Val Ser Val Thr Cys Lys Ala Ser Gln His Val Gly Thr His
            20                  25                  30

Val Thr Trp Tyr Gln Gln Lys Pro Gly Gln Pro Pro Lys Leu Leu Ile
        35                  40                  45

Tyr Ser Thr Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Phe Tyr Ser Tyr Pro Leu
                85                  90                  95

Thr Phe Gly Gly Gly Thr Lys Val Glu Ile Lys
            100                 105
```

<210> SEQ ID NO 20
<211> LENGTH: 107
<212> TYPE: PRT
<213> ORGANISM: Homo sapiens

<400> SEQUENCE: 20

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr His
            20                  25                  30

Val Thr Trp Tyr Gln Gln Lys Pro Gly Gln Ser Pro Lys Ala Leu Ile
```

```
                35                  40                  45
Tyr Ser Thr Ser Tyr Arg Tyr Ser Gly Val Pro Asp Arg Phe Ser Gly
         50                  55                  60
Ser Gly Ser Gly Thr Asp Phe Thr Leu Thr Ile Ser Ser Leu Gln Ala
 65                  70                  75                  80
Glu Asp Val Ala Val Tyr Tyr Cys Gln Gln Phe Tyr Ser Tyr Pro Leu
                 85                  90                  95
Thr Phe Gly Gly Gly Thr Lys Val Glu Ile Lys
                100                 105

<210> SEQ ID NO 21
<211> LENGTH: 107
<212> TYPE: PRT
<213> ORGANISM: Homo sapiens

<400> SEQUENCE: 21

Asp Ile Val Met Thr Gln Ser Pro Asp Ser Leu Ala Val Ser Leu Gly
  1               5                  10                  15
Glu Arg Ala Thr Ile Asn Cys Lys Ala Ser Gln His Val Gly Thr His
             20                  25                  30
Val Thr Trp Tyr Gln Gln Lys Pro Gly Gln Pro Pro Lys Leu Leu Ile
         35                  40                  45
Tyr Ser Thr Ser Tyr Arg Tyr Ser Gly Val Pro Asp Arg Phe Thr Gly
         50                  55                  60
Ser Gly Ser Gly Thr Asp Phe Thr Leu Thr Ile Thr Asn Val Gln Ser
 65                  70                  75                  80
Glu Asp Leu Ala Glu Tyr Phe Cys Gln Gln Phe Tyr Ser Tyr Pro Leu
                 85                  90                  95
Thr Phe Gly Gly Gly Thr Lys Val Glu Ile Lys
                100                 105

<210> SEQ ID NO 22
<211> LENGTH: 107
<212> TYPE: PRT
<213> ORGANISM: Homo sapiens

<400> SEQUENCE: 22

Asp Ile Val Met Thr Gln Ser Pro Asp Ser Leu Ala Val Ser Leu Gly
  1               5                  10                  15
Glu Arg Ala Thr Ile Asn Cys Lys Ala Ser Gln His Val Gly Thr His
             20                  25                  30
Val Thr Trp Tyr Gln Gln Lys Pro Gly Gln Pro Pro Lys Leu Leu Ile
         35                  40                  45
Tyr Ser Thr Ser Tyr Arg Tyr Ser Gly Val Pro Asp Arg Phe Ser Gly
         50                  55                  60
Ser Gly Ser Gly Thr Asp Phe Thr Leu Thr Ile Ser Ser Leu Gln Ala
 65                  70                  75                  80
Glu Asp Val Ala Val Tyr Tyr Cys Gln Gln Phe Tyr Ser Tyr Pro Leu
                 85                  90                  95
Thr Phe Gly Ala Gly Thr Lys Leu Glu Leu Lys
                100                 105

<210> SEQ ID NO 23
<211> LENGTH: 107
<212> TYPE: PRT
<213> ORGANISM: Homo sapiens

<400> SEQUENCE: 23
```

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr His
            20                  25                  30

Val Thr Trp Tyr Gln Gln Lys Pro Gly Gln Ser Pro Lys Leu Leu Ile
        35                  40                  45

Tyr Ser Thr Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Phe Tyr Ser Tyr Pro Leu
                85                  90                  95

Thr Phe Gly Ala Gly Thr Lys Leu Glu Leu Lys
                100                 105

<210> SEQ ID NO 24
<211> LENGTH: 107
<212> TYPE: PRT
<213> ORGANISM: Homo sapiens

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr His
            20                  25                  30

Val Thr Trp Tyr Gln Gln Lys Pro Gly Gln Pro Pro Lys Ala Leu Ile
        35                  40                  45

Tyr Ser Thr Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Phe Tyr Ser Tyr Pro Leu
                85                  90                  95

Thr Phe Gly Ala Gly Thr Lys Leu Glu Leu Lys
                100                 105

<210> SEQ ID NO 25
<211> LENGTH: 107
<212> TYPE: PRT
<213> ORGANISM: Homo sapiens

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr His
            20                  25                  30

Val Thr Trp Tyr Gln Gln Lys Pro Gly Gln Pro Pro Lys Leu Leu Ile
        35                  40                  45

Tyr Ser Thr Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Val Tyr Tyr Cys Gln Gln Phe Tyr Ser Tyr Pro Leu
                85                  90                  95

Thr Phe Gly Ala Gly Thr Lys Leu Glu Leu Lys
                100                 105
```

<210> SEQ ID NO 26
<211> LENGTH: 107
<212> TYPE: PRT
<213> ORGANISM: Homo sapiens

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr His
            20                  25                  30

Val Thr Trp Tyr Gln Gln Lys Pro Gly Gln Pro Pro Lys Leu Leu Ile
        35                  40                  45

Tyr Ser Thr Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Phe Tyr Ser Tyr Pro Leu
                85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: Homo sapiens

<400> SEQUENCE: 27

Glu Ile Gln Leu Thr Gln Ser Pro Ser Ser Leu Ser Ala Ser Val Gly
1               5                   10                  15

Asp Thr Val Thr Ile Thr Cys Arg Ala Ser Gln Asn Ile Asn Thr Phe
            20                  25                  30

Leu Asn Trp Tyr Gln Gln Lys Pro Gly Lys Ala Pro Val Leu Leu Ile
        35                  40                  45

Tyr Ala Ala Ser His Leu Gln Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Thr Tyr Tyr Cys Gln Gln Phe Tyr Ser Tyr Pro Leu
                85                  90                  95

Thr Phe Gly Gln Gly Thr Lys Leu Glu Ile Lys
            100                 105

<210> SEQ ID NO 28
<211> LENGTH: 107
<212> TYPE: PRT
<213> ORGANISM: Homo sapiens

<400> SEQUENCE: 28

Glu Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Ser Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Tyr Tyr Cys Gln Gln Phe Tyr Ser Tyr Pro Leu
                 85                  90                  95

Thr Phe Gly Gln Gly Thr Lys Leu Glu Ile Lys
            100                 105
```

<210> SEQ ID NO 29
<211> LENGTH: 107
<212> TYPE: PRT
<213> ORGANISM: Homo sapiens

<400> SEQUENCE: 29

```
Glu Ile Gln Leu Thr Gln Ser Pro Ser Leu Ser Ala Ser Val Gly
 1               5                  10                  15

Asp Thr Val Thr Ile Thr Cys Arg Ala Ser Gln Asn Ile Asn Thr Phe
                 20                  25                  30

Leu Asn Trp Tyr Gln Gln Lys Pro Gly Lys Ala Pro Lys Leu Leu Ile
             35                  40                  45

Tyr Ala Ala Ser Phe Leu Gln Asn Gly Val Pro Ser Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Ala Gly Val Tyr Tyr Cys Gln Gln Phe Tyr Ser Tyr Pro Leu
                 85                  90                  95

Thr Phe Gly Gln Gly Thr Lys Leu Glu Ile Lys
            100                 105
```

<210> SEQ ID NO 30
<211> LENGTH: 107
<212> TYPE: PRT
<213> ORGANISM: Homo sapiens

<400> SEQUENCE: 30

```
Glu Ile Thr Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Phe Tyr Ser Tyr Pro Leu
                 85                  90                  95

Thr Phe Gly Gln Gly Thr Lys Leu Glu Ile Lys
            100                 105
```

<210> SEQ ID NO 31
<211> LENGTH: 107
<212> TYPE: PRT
<213> ORGANISM: Homo sapiens

<400> SEQUENCE: 31

```
Glu Ile Thr Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
```

-continued

```
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Thr Tyr Tyr Cys Gln Gln Phe Tyr Ser Tyr Pro Leu
                85                  90                  95

Thr Phe Gly Gln Gly Thr Lys Leu Glu Ile Lys
            100                 105

<210> SEQ ID NO 32
<211> LENGTH: 107
<212> TYPE: PRT
<213> ORGANISM: Homo sapiens

<400> SEQUENCE: 32

Glu Ile Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Thr Tyr Tyr Cys Gln Gln Phe Tyr Ser Tyr Pro Leu
                85                  90                  95

Thr Phe Gly Gln Gly Thr Lys Leu Glu Ile Lys
            100                 105

<210> SEQ ID NO 33
<211> LENGTH: 54
<212> TYPE: PRT
<213> ORGANISM: Homo sapiens

<400> SEQUENCE: 33

Thr Ala Thr Ala Thr Ala Thr Ala Thr Ala Thr Ala Thr Ala Thr Ala
1               5                   10                  15

Cys Cys Cys Cys Gly Gly Gly Cys Cys Ala Ala Thr Gly Thr
            20                  25                  30

Gly Ala Cys Ala Thr Thr Gly Thr Gly Ala Thr Gly Cys Cys Cys
        35                  40                  45

Ala Gly Thr Cys Thr Cys
    50

<210> SEQ ID NO 34
<211> LENGTH: 44
<212> TYPE: DNA
<213> ORGANISM: Homo sapiens

<400> SEQUENCE: 34
tatatatata tatacgtacg tttcagctcc agcttggtcc cagc          44

<210> SEQ ID NO 35
<211> LENGTH: 98
```

```
<212> TYPE: DNA
<213> ORGANISM: Homo sapiens

<400> SEQUENCE: 35
tatatatata tatatctaga catatatatg ggtgacaatg acatccactt tgcctttctc      60
tccacaggtg tccactccca ggttcagctg cagcagtc                             98

<210> SEQ ID NO 36
<211> LENGTH: 74
<212> TYPE: DNA
<213> ORGANISM: Homo sapiens

<400> SEQUENCE: 36 gccagggggga agaccgatgg gcccttggtg gaggctgagg agactgtgag agtggtgcct     60
tggccccagt agtc                                                       74

<210> SEQ ID NO 37
<211> LENGTH: 39
<212> TYPE: DNA
<213> ORGANISM: Homo sapiens

<400> SEQUENCE: 37
tcgctacccg gggccaaatg tgacatcctg atgacccaa                            39

<210> SEQ ID NO 38
<211> LENGTH: 30
<212> TYPE: DNA
<213> ORGANISM: Homo sapiens

<400> SEQUENCE: 38
agccaccgta cgtttcattt ccagcttggt                                      30

<210> SEQ ID NO 39
<211> LENGTH: 90
<212> TYPE: DNA
<213> ORGANISM: Homo sapiens

<400> SEQUENCE: 39
gcttgcggtc tagacatata tatgggtgac aatgacatcc actttgcctt tctctccaca     60
ggtgtccact cccaggtcca gctgcagcag                                      90

<210> SEQ ID NO 40
<211> LENGTH: 44
<212> TYPE: DNA
<213> ORGANISM: Homo sapiens

<400> SEQUENCE: 40
gtatccgatg ggcccttggt ggaggctgca gagacagtga ccag                      44

<210> SEQ ID NO 41
<211> LENGTH: 62
<212> TYPE: DNA
<213> ORGANISM: Homo sapiens

<400> SEQUENCE: 41
gcagccacag cccgtttgat ctcgaccttg gtcccaccac cgaacgtgag aggatagctg     60
ta                                                                    62

<210> SEQ ID NO 42
<211> LENGTH: 66
<212> TYPE: DNA
```

<210> SEQ ID NO 42
<211> LENGTH: 66
<212> TYPE: DNA
<213> ORGANISM: Homo sapiens

<400> SEQUENCE: 42
ttcactctca ccatcagtag tttgcaggct gaagacgtgg cagtgtatta ctgtcagcaa    60
ttttac                                                               66

<210> SEQ ID NO 43
<211> LENGTH: 66
<212> TYPE: DNA
<213> ORGANISM: Homo sapiens

<400> SEQUENCE: 43
gtaaaattgc tgacagtaat acactgccac gtcttcagcc tgcaaactac tgatggtgag    60
agtgaa                                                               66

<210> SEQ ID NO 44
<211> LENGTH: 27
<212> TYPE: DNA
<213> ORGANISM: Homo sapiens

<400> SEQUENCE: 44
ccctgatcgc ttcagtggca gtggatc                                        27

<210> SEQ ID NO 45
<211> LENGTH: 27
<212> TYPE: DNA
<213> ORGANISM: Homo sapiens

<400> SEQUENCE: 45
gatccactgc cactgaagcg atcaggg                                        27

<210> SEQ ID NO 46
<211> LENGTH: 39
<212> TYPE: DNA
<213> ORGANISM: Homo sapiens

<400> SEQUENCE: 46
cagaaaccag ggcaaccccc taaactgctg atttactcg                           39

<210> SEQ ID NO 47
<211> LENGTH: 39
<212> TYPE: DNA
<213> ORGANISM: Homo sapiens

<400> SEQUENCE: 47
cgagtaaatc agcagtttag ggggttgccc tggtttctg                           39

<210> SEQ ID NO 48
<211> LENGTH: 75
<212> TYPE: DNA
<213> ORGANISM: Homo sapiens

<400> SEQUENCE: 48
gtgatgaccc agtctcccga cagcctggct gtctcactgg gagagagggc taccatcaat    60
tgcaaggcca gtcag                                                     75

<210> SEQ ID NO 49
<211> LENGTH: 54
<212> TYPE: DNA
<213> ORGANISM: Homo sapiens

<400> SEQUENCE: 49

```
tatatatata tatataccccc ggggccaaat gtgacattgt gatgacccag tctc          54
```

<210> SEQ ID NO 50
<211> LENGTH: 59
<212> TYPE: DNA
<213> ORGANISM: Homo sapiens

<400> SEQUENCE: 50

```
gcagccaccg tacgtttgat ctcgaccttg gtcccaccac cgaacgtgag aggatagct     59
```

<210> SEQ ID NO 51
<211> LENGTH: 51
<212> TYPE: DNA
<213> ORGANISM: Homo sapiens

<400> SEQUENCE: 51

```
ctcagcagcc tgcgctctga ggacacagcc gtctattact gtgcaagagc g             51
```

<210> SEQ ID NO 52
<211> LENGTH: 40
<212> TYPE: DNA
<213> ORGANISM: Homo sapiens

<400> SEQUENCE: 52

```
ggaggctgag gagactgtga ccagggtgcc ttggccccag                          40
```

<210> SEQ ID NO 53
<211> LENGTH: 51
<212> TYPE: DNA
<213> ORGANISM: Homo sapiens

<400> SEQUENCE: 53

```
cgctcttgca cagtaataga cggctgtgtc ctcagagcgc aggctgctga g             51
```

<210> SEQ ID NO 54
<211> LENGTH: 69
<212> TYPE: DNA
<213> ORGANISM: Homo sapiens

<400> SEQUENCE: 54

```
gagaagttca agggccgcgt cacaatcaca gcagataaat ccacatctac agcctacatg   60
gaactcagc                                                            69
```

<210> SEQ ID NO 55
<211> LENGTH: 69
<212> TYPE: DNA
<213> ORGANISM: Homo sapiens

<400> SEQUENCE: 55

```
gctgagttcc atgtaggctg tagatgtgga tttatctgct gtgattgtga cgcggccctt   60
gaacttctc                                                            69
```

<210> SEQ ID NO 56
<211> LENGTH: 63
<212> TYPE: DNA
<213> ORGANISM: Homo sapiens

<400> SEQUENCE: 56

```
ctggatagag tgggtccgcc aggctcctgg acagggcctt gagtggatgg gagagatttt   60
acc                                                                  63
```

<210> SEQ ID NO 57
<211> LENGTH: 63
<212> TYPE: DNA
<213> ORGANISM: Homo sapiens

<400> SEQUENCE: 57
ggtaaaatct ctcccatcca ctcaaggccc tgtccaggag cctggcggac ccactctatc        60
cag                                                                      63

<210> SEQ ID NO 58
<211> LENGTH: 69
<212> TYPE: DNA
<213> ORGANISM: Homo sapiens

<400> SEQUENCE: 58
tctggagctg aggtcaaaaa gcctgggtct tcagtgaagg tctcctgcaa ggcttctggc        60
tacacattc                                                                69

<210> SEQ ID NO 59
<211> LENGTH: 69
<212> TYPE: DNA
<213> ORGANISM: Homo sapiens

<400> SEQUENCE: 59
gaatgtgtag ccagaagcct tgcaggagac cttcactgaa gacccaggct ttttgacctc        60
agctccaga                                                                69

<210> SEQ ID NO 60
<211> LENGTH: 22
<212> TYPE: DNA
<213> ORGANISM: Homo sapiens

<400> SEQUENCE: 60
aagcttgttg actagtgaga tc                                                 22

<210> SEQ ID NO 61
<211> LENGTH: 61
<212> TYPE: DNA
<213> ORGANISM: Homo sapiens

<400> SEQUENCE: 61
tatatatata tagggccctt ggtggaggct gaggagactg tgaccagggt gccttggccc        60
c                                                                        61

<210> SEQ ID NO 62
<211> LENGTH: 30
<212> TYPE: DNA
<213> ORGANISM: Homo sapiens

<400> SEQUENCE: 62
caggttcagc tggtccagtc tggagctgag                                         30

<210> SEQ ID NO 63
<211> LENGTH: 30
<212> TYPE: DNA
<213> ORGANISM: Homo sapiens

<400> SEQUENCE: 63
ctcagctcca gactggacca gctgaacctg                                         30

```
<210> SEQ ID NO 64
<211> LENGTH: 61
<212> TYPE: DNA
<213> ORGANISM: Homo sapiens

<400> SEQUENCE: 64
tatatatata tagggccctt ggtggaggct gaggagactg tgaccagggt gccttggccc     60
c                                                                     61

<210> SEQ ID NO 65
<211> LENGTH: 48
<212> TYPE: DNA
<213> ORGANISM: Homo sapiens

<400> SEQUENCE: 65
agcagcctga aagcttctga cacagccatg tattactgtg caagagcg                  48

<210> SEQ ID NO 66
<211> LENGTH: 48
<212> TYPE: DNA
<213> ORGANISM: Homo sapiens

<400> SEQUENCE: 66
cgctcttgca cagtaataca tggctgtgtc agaagctttc aggctgct                  48

<210> SEQ ID NO 67
<211> LENGTH: 72
<212> TYPE: DNA
<213> ORGANISM: Homo sapiens

<400> SEQUENCE: 67
aagttcaagg gccaggtcac aatctctgca gataaatcca tctctacagc ctacctgcaa     60
tggagcagcc tg                                                         72

<210> SEQ ID NO 68
<211> LENGTH: 72
<212> TYPE: DNA
<213> ORGANISM: Homo sapiens

<400> SEQUENCE: 68
caggctgctc cattgcaggt aggctgtaga gatggattta tctgcagaga ttgtgacctg     60
gcccttgaac tt                                                         72

<210> SEQ ID NO 69
<211> LENGTH: 63
<212> TYPE: DNA
<213> ORGANISM: Homo sapiens

<400> SEQUENCE: 69
ctggatagag tgggtccgcc agatgcctgg aaaaggcctt gagtggatgg gagagatttt     60
acc                                                                   63

<210> SEQ ID NO 70
<211> LENGTH: 63
<212> TYPE: DNA
<213> ORGANISM: Homo sapiens

<400> SEQUENCE: 70
ggtaaaatct ctcccatcca ctcaaggcct tttccaggca tctggcggac ccactctatc     60
cag                                                                   63
```

<210> SEQ ID NO 71
<211> LENGTH: 69
<212> TYPE: DNA
<213> ORGANISM: Homo sapiens

<400> SEQUENCE: 71
tctggagctg aggtcaaaaa gcctggggaa tcactgaaga tctcctgcaa ggggtctggc    60
tacacattc                                                           69

<210> SEQ ID NO 72
<211> LENGTH: 69
<212> TYPE: DNA
<213> ORGANISM: Homo sapiens

<400> SEQUENCE: 72
gaatgtgtag ccagacccct tgcaggagat cttcagtgat tccccaggct ttttgacctc    60
agctccaga                                                           69

<210> SEQ ID NO 73
<211> LENGTH: 22
<212> TYPE: DNA
<213> ORGANISM: Homo sapiens

<400> SEQUENCE: 73
aagcttgttg actagtgaga tc                                            22

<210> SEQ ID NO 74
<211> LENGTH: 39
<212> TYPE: DNA
<213> ORGANISM: Homo sapiens

<400> SEQUENCE: 74
ggtgtccact ccgaagttca gctggtccag tctggagct                          39

<210> SEQ ID NO 75
<211> LENGTH: 39
<212> TYPE: DNA
<213> ORGANISM: Homo sapiens

<400> SEQUENCE: 75
agctccagac tggaccagct gaacttcgga gtggacacc                          39

<210> SEQ ID NO 76
<211> LENGTH: 68
<212> TYPE: DNA
<213> ORGANISM: Homo sapiens

<400> SEQUENCE: 76
tggctccccg gggccaaatg tgacatccag atgacccagt ctccatcctc actgtctgca    60
tctgtagg                                                            68

<210> SEQ ID NO 77
<211> LENGTH: 59
<212> TYPE: DNA
<213> ORGANISM: Homo sapiens

<400> SEQUENCE: 77
gcaagtcagg acattggcag taatataggg tggtttcagc agaaaccagg gaaagcccc    59

<210> SEQ ID NO 78
<211> LENGTH: 72

<212> TYPE: DNA
<213> ORGANISM: Homo sapiens

<400> SEQUENCE: 78

```
ggatccaatt tggaagatgg ggtcccatca aggttcagcg gcagtggatc tgggacagat    60
ttcactctca cc                                                       72
```

<210> SEQ ID NO 79
<211> LENGTH: 45
<212> TYPE: DNA
<213> ORGANISM: Homo sapiens

<400> SEQUENCE: 79

```
tactgcgtac agtttgctca gtttccgtac acttttggcc agggg                   45
```

<210> SEQ ID NO 80
<211> LENGTH: 67
<212> TYPE: DNA
<213> ORGANISM: Homo sapiens

<400> SEQUENCE: 80

```
ctgccaatgt cctgacttgc atgacaagtg atggtgactc tgtctcctac agatgcagac    60
agtgagg                                                             67
```

<210> SEQ ID NO 81
<211> LENGTH: 58
<212> TYPE: DNA
<213> ORGANISM: Homo sapiens

<400> SEQUENCE: 81

```
atcttccaaa ttggatccat gatagatcag ggacttaggg gctttccctg gtttctgc     58
```

<210> SEQ ID NO 82
<211> LENGTH: 74
<212> TYPE: DNA
<213> ORGANISM: Homo sapiens

<400> SEQUENCE: 82

```
gcaaactgta cgcagtaata agttgcaaaa tcttcaggct gcaggctgct gatggtgaga    60
gtgaaatctg tccc                                                     74
```

<210> SEQ ID NO 83
<211> LENGTH: 50
<212> TYPE: DNA
<213> ORGANISM: Homo sapiens

<400> SEQUENCE: 83

```
gccaccgtac gtttgatctc cagcttggtc ccctggccaa aagtgtacgg              50
```

<210> SEQ ID NO 84
<211> LENGTH: 70
<212> TYPE: DNA
<213> ORGANISM: Homo sapiens

<400> SEQUENCE: 84

```
ttgaggtcta gacatatata tgggtgacaa tgacatccac tttgcctttc tctccacagg    60
tgtccactcc                                                          70
```

<210> SEQ ID NO 85
<211> LENGTH: 77
<212> TYPE: DNA

<210> SEQ ID NO 85
<211> LENGTH: 77
<212> TYPE: DNA
<213> ORGANISM: Homo sapiens

<400> SEQUENCE: 85

```
gaagaagcct gggtcctcgg tgaaggtctc ctgcaaggct tctggaggca ccttcagcaa    60
ctactacata ggttggg                                                   77
```

<210> SEQ ID NO 86
<211> LENGTH: 63
<212> TYPE: DNA
<213> ORGANISM: Homo sapiens

<400> SEQUENCE: 86

```
ggagatattt accctggaag tacttatatt aactacaatg agaagttcaa gggcagagtc    60
acg                                                                  63
```

<210> SEQ ID NO 87
<211> LENGTH: 77
<212> TYPE: DNA
<213> ORGANISM: Homo sapiens

<400> SEQUENCE: 87

```
gagctgagca gcctgagatc tgaggacacg gccgtgtatt actgtgcgag atcggatgat    60
ggttactacg ggtttcc                                                   77
```

<210> SEQ ID NO 88
<211> LENGTH: 68
<212> TYPE: DNA
<213> ORGANISM: Homo sapiens

<400> SEQUENCE: 88

```
cgaggaccca ggcttcttca cctcagcccc agactgcacc agctgcacct gggagtggac    60
acctgtgg                                                             68
```

<210> SEQ ID NO 89
<211> LENGTH: 67
<212> TYPE: DNA
<213> ORGANISM: Homo sapiens

<400> SEQUENCE: 89

```
agggtaaata tctcccatcc actcaagccc ttgtccaggg gcctgtcgca cccaacctat    60
gtagtag                                                              67
```

<210> SEQ ID NO 90
<211> LENGTH: 68
<212> TYPE: DNA
<213> ORGANISM: Homo sapiens

<400> SEQUENCE: 90

```
tcaggctgct cagctccatg taggctgtgc tcgtggattt gtccgcggta atcgtgactc    60
tgcccttg                                                             68
```

<210> SEQ ID NO 91
<211> LENGTH: 76
<212> TYPE: DNA
<213> ORGANISM: Homo sapiens

<400> SEQUENCE: 91

```
accgatgggc ccttggtgga ggctgaagag acagtgacca gagtcccttg gccccagtaa    60
ggaaacccgt agtaac                                                    76
```

<210> SEQ ID NO 92
<211> LENGTH: 72
<212> TYPE: DNA
<213> ORGANISM: Homo sapiens

<400> SEQUENCE: 92
cttgaggtct agacatatat atgggtgaca atgacatcca ctttgccttt ctctccacag    60
gtgtccactc cg                                                        72

<210> SEQ ID NO 93
<211> LENGTH: 76
<212> TYPE: DNA
<213> ORGANISM: Homo sapiens

<400> SEQUENCE: 93 gggggtccc tgagactctc ctgtgcagcc tctggattca ccttcagtaa ctactacata    60
ggttgggtcc gccagg                                                    76

<210> SEQ ID NO 94
<211> LENGTH: 72
<212> TYPE: DNA
<213> ORGANISM: Homo sapiens

<400> SEQUENCE: 94
ggaagtactt atattaacta caatgagaag ttcaagggcc gattcaccat ctccagagac    60
aacgccaaga ac                                                        72

<210> SEQ ID NO 95
<211> LENGTH: 59
<212> TYPE: DNA
<213> ORGANISM: Homo sapiens

<400> SEQUENCE: 95
cggctgtgta ttactgtgcg agatcggatg atggttacta cgggtttcct tactggggc    59

<210> SEQ ID NO 96
<211> LENGTH: 74
<212> TYPE: DNA
<213> ORGANISM: Homo sapiens

<400> SEQUENCE: 96
tctcagggac cccccaggct tgaccaggcc tcccccagac tccaccagct gcacctcgga    60
gtggacacct gtgg                                                      74

<210> SEQ ID NO 97
<211> LENGTH: 72
<212> TYPE: DNA
<213> ORGANISM: Homo sapiens

<400> SEQUENCE: 97
aatataagta cttccagggt aaatatctga gacccactcc agccccttcc ctggagcctg    60
gcggacccaa cc                                                        72

<210> SEQ ID NO 98
<211> LENGTH: 73
<212> TYPE: DNA
<213> ORGANISM: Homo sapiens

<400> SEQUENCE: 98

```
cagtaataca cagccgtgtc ctcggctctc aggctgttca tttgcagata cagtgagttc    60
ttggcgttgt ctc                                                       73

<210> SEQ ID NO 99
<211> LENGTH: 70
<212> TYPE: DNA
<213> ORGANISM: Homo sapiens

<400> SEQUENCE: 99
gaccgatggg cccttggtgg aggctgaaga gacagtgacc agagtccctt ggccccagta    60
aggaaacccg                                                           70

<210> SEQ ID NO 100
<211> LENGTH: 63
<212> TYPE: DNA
<213> ORGANISM: Homo sapiens

<400> SEQUENCE: 100
tatatatata tatatata ggcccagccg gcccaggttc agctgcagca gtctggagct      60
gag                                                                  63

<210> SEQ ID NO 101
<211> LENGTH: 58
<212> TYPE: DNA
<213> ORGANISM: Homo sapiens

<400> SEQUENCE: 101
tatatatata tatatata gcggccgcag cccgtttcag ctccagcttg gtcccagc        58

<210> SEQ ID NO 102
<211> LENGTH: 74
<212> TYPE: DNA
<213> ORGANISM: Homo sapiens

<400> SEQUENCE: 102
ggtggaggcg gttcaggcgg aggtggctct ggcggtggcg gatcggacat tgtgatgacc    60
cagtctcaaa aatt                                                      74

<210> SEQ ID NO 103
<211> LENGTH: 76
<212> TYPE: DNA
<213> ORGANISM: Homo sapiens

<400> SEQUENCE: 103
cgatccgcca ccgccagagc cacctccgcc tgaaccgcct ccacctgagg agactgtgag    60
agtggtgcct tggccc                                                    76

<210> SEQ ID NO 104
<211> LENGTH: 37
<212> TYPE: DNA
<213> ORGANISM: Homo sapiens

<400> SEQUENCE: 104
acctggtatc aacagtaata agggcaatct cctaaag                             37

<210> SEQ ID NO 105
<211> LENGTH: 37
<212> TYPE: DNA
<213> ORGANISM: Homo sapiens

<400> SEQUENCE: 105
```
ctttaggaga ttgcccttat tactgttgat accaggt                                37

<210> SEQ ID NO 106
<211> LENGTH: 37
<212> TYPE: DNA
<213> ORGANISM: Homo sapiens

<400> SEQUENCE: 106
gcggtggcgg atcggagatc cagwtgaccc agtctcc                                37

<210> SEQ ID NO 107
<211> LENGTH: 37
<212> TYPE: DNA
<213> ORGANISM: Homo sapiens

<400> SEQUENCE: 107
gcggtggcgg atcggagatc gtgatgacyc agwctcc                                37

<210> SEQ ID NO 108
<211> LENGTH: 37
<212> TYPE: DNA
<213> ORGANISM: Homo sapiens

<400> SEQUENCE: 108
gcggtggcgg atcggagatc gtgwtgacrc agtctcc                                37

<210> SEQ ID NO 109
<211> LENGTH: 37
<212> TYPE: DNA
<213> ORGANISM: Homo sapiens

<400> SEQUENCE: 109
gcggtggcgg atcggagatc acactcacgc agtctcc                                37

<210> SEQ ID NO 110
<211> LENGTH: 51
<212> TYPE: DNA
<213> ORGANISM: Homo sapiens

<400> SEQUENCE: 110
cgtgagagga tagctgtaaa attgctgaca gtaatacact gcaaaatctt c                51

<210> SEQ ID NO 111
<211> LENGTH: 51
<212> TYPE: DNA
<213> ORGANISM: Homo sapiens

<400> SEQUENCE: 111
cgtgagagga tagctgtaaa attgctgaca gtaataaacc ccarcatcct c                51

<210> SEQ ID NO 112
<211> LENGTH: 51
<212> TYPE: DNA
<213> ORGANISM: Homo sapiens

<400> SEQUENCE: 112
cgtgagagga tagctgtaaa attgctgaca gtaataagtt gcaaaatctt c                51

<210> SEQ ID NO 113
<211> LENGTH: 67
<212> TYPE: DNA
<213> ORGANISM: Homo sapiens

<400> SEQUENCE: 113
tatatatata tataccctcag gtggaggcgg ttcaggcgga ggtggctctg gcggtggcgg        60
atcggag        67

<210> SEQ ID NO 114
<211> LENGTH: 76
<212> TYPE: DNA
<213> ORGANISM: Homo sapiens

<400> SEQUENCE: 114
tatatatata tatagcggcc gcagcccgtt tgatctccag cttggtcccc tgaccgaacg        60
tgagaggata gctgta        76

<210> SEQ ID NO 115
<211> LENGTH: 36
<212> TYPE: DNA
<213> ORGANISM: Homo sapiens

<400> SEQUENCE: 115
cttgagtggc ttggataata attacctgga agtggt        36

<210> SEQ ID NO 116
<211> LENGTH: 36
<212> TYPE: DNA
<213> ORGANISM: Homo sapiens

<400> SEQUENCE: 116
accacttcca ggtaattatt atccaagcca ctcaag        36

<210> SEQ ID NO 117
<211> LENGTH: 48
<212> TYPE: DNA
<213> ORGANISM: Homo sapiens

<400> SEQUENCE: 117
tatatatata taggcccagc cggcccagrt gcagctggtg cagtctgg        48

<210> SEQ ID NO 118
<211> LENGTH: 48
<212> TYPE: DNA
<213> ORGANISM: Homo sapiens

<400> SEQUENCE: 118
tatatatata taggcccagc cggcccagat caccttgaag gagtctgg        48

<210> SEQ ID NO 119
<211> LENGTH: 48
<212> TYPE: DNA
<213> ORGANISM: Homo sapiens

<400> SEQUENCE: 119
tatatatata taggcccagc cggccgaggt gcagctgktg sagtctgg        48

<210> SEQ ID NO 120
<211> LENGTH: 48
<212> TYPE: DNA
<213> ORGANISM: Homo sapiens

<400> SEQUENCE: 120
tatatatata taggcccagc cggcccaggt gcagctgcag gagtcggg        48

<210> SEQ ID NO 121
<211> LENGTH: 53
<212> TYPE: DNA
<213> ORGANISM: Homo sapiens

<400> SEQUENCE: 121
gacgtaacta ctaccgtagt aatccgctct cgcacagtaa tacadggccy tgt        53

<210> SEQ ID NO 122
<211> LENGTH: 25
<212> TYPE: DNA
<213> ORGANISM: Homo sapiens

<400> SEQUENCE: 122
tatatatata taggcccagc cggcc                                       25

<210> SEQ ID NO 123
<211> LENGTH: 57
<212> TYPE: DNA
<213> ORGANISM: Homo sapiens

<400> SEQUENCE: 123
tatatatata tataccttgg ccccagtagt caaacttgac gtaactacta ccgtagt    57

<210> SEQ ID NO 124
<211> LENGTH: 144
<212> TYPE: PRT
<213> ORGANISM: Homo sapiens

<400> SEQUENCE: 124

Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140

<210> SEQ ID NO 125
<211> LENGTH: 435
<212> TYPE: DNA
<213> ORGANISM: Homo sapiens

<400> SEQUENCE: 125
atgcttctgg ccatggtcct tacctctgcc ctgctcctgt gctccgtggc aggccagggg    60
tgtccaacct tggcggggat cctggacatc aacttcctca tcaacaagat gcaggaagat   120
ccagcttcca gtgccactg cagtgctaat gtgaccagtt gtctctgttt gggcattccc    180
tctgacaact gcaccagacc atgcttcagt gagagactgt ctcagatgac caataccacc   240

-continued

```
atgcaaacaa gatacccact gattttcagt cgggtgaaaa aatcagttga agtactaaag      300
aacaacaagt gtccatattt ttcctgtgaa cagccatgca accaaaccac ggcaggcaac      360
gcgctgacat ttctgaagag tcttctggaa attttccaga agaaaagat gagagggatg       420 agaggcaaga tatga                                                      435
```

<210> SEQ ID NO 126
<211> LENGTH: 522
<212> TYPE: PRT
<213> ORGANISM: Homo sapiens

<400> SEQUENCE: 126

| | | | | | | | | | | | | | | |
|---|---|---|---|---|---|---|---|---|---|---|---|---|---|---|
| Met | Gly | Leu | Gly | Arg | Cys | Ile | Trp | Glu | Gly | Trp | Thr | Leu | Ser | Glu |
| 1 | | | | 5 | | | | | 10 | | | | | 15 |
| Ala | Leu | Arg | Arg | Asp | Met | Gly | Thr | Trp | Leu | Leu | Ala | Cys | Ile | Cys |
| | | | 20 | | | | | 25 | | | | | 30 | |
| Ile | Cys | Thr | Cys | Val | Cys | Leu | Gly | Val | Ser | Val | Thr | Gly | Gly | Gln |
| | | 35 | | | | | 40 | | | | | 45 | | |
| Gly | Pro | Arg | Ser | Arg | Thr | Phe | Thr | Cys | Leu | Thr | Asn | Asn | Ile | Leu |
| | 50 | | | | | 55 | | | | | 60 | | | |
| Arg | Ile | Asp | Cys | His | Trp | Ser | Ala | Pro | Glu | Leu | Gly | Gln | Gly | Ser |
| 65 | | | | | 70 | | | | | 75 | | | | | 80 |
| Ser | Pro | Trp | Leu | Leu | Phe | Thr | Ser | Asn | Gln | Ala | Pro | Gly | Gly | Thr |
| | | | | 85 | | | | | 90 | | | | | 95 |
| His | Lys | Cys | Ile | Leu | Arg | Gly | Ser | Glu | Cys | Thr | Val | Val | Leu | Pro |
| | | | 100 | | | | | 105 | | | | | 110 | |
| Pro | Glu | Ala | Val | Leu | Val | Pro | Ser | Asp | Asn | Phe | Thr | Ile | Thr | Phe |
| | | 115 | | | | | 120 | | | | | 125 | | |
| His | His | Cys | Met | Ser | Gly | Arg | Glu | Gln | Val | Ser | Leu | Val | Asp | Pro |
| | 130 | | | | | 135 | | | | | 140 | | | |
| Glu | Tyr | Leu | Pro | Arg | Arg | His | Val | Lys | Leu | Asp | Pro | Pro | Ser | Asp |
| 145 | | | | | 150 | | | | | 155 | | | | | 160 |
| Leu | Gln | Ser | Asn | Ile | Ser | Ser | Gly | His | Cys | Ile | Leu | Thr | Trp | Ser |
| | | | | 165 | | | | | 170 | | | | | 175 |
| Ile | Ser | Pro | Ala | Leu | Glu | Pro | Met | Thr | Thr | Leu | Leu | Ser | Tyr | Glu |
| | | | 180 | | | | | 185 | | | | | 190 | |
| Leu | Ala | Phe | Lys | Lys | Gln | Glu | Glu | Ala | Trp | Glu | Gln | Ala | Gln | His |
| | | 195 | | | | | 200 | | | | | 205 | | |
| Arg | Asp | His | Ile | Val | Gly | Val | Thr | Trp | Leu | Ile | Leu | Glu | Ala | Phe |
| | 210 | | | | | 215 | | | | | 220 | | | |
| Glu | Leu | Asp | Pro | Gly | Phe | Ile | His | Glu | Ala | Arg | Leu | Arg | Val | Gln |
| 225 | | | | | 230 | | | | | 235 | | | | | 240 |
| Met | Ala | Thr | Leu | Glu | Asp | Asp | Val | Val | Glu | Glu | Arg | Tyr | Thr | Gly |
| | | | | 245 | | | | | 250 | | | | | 255 |
| Gln | Trp | Ser | Glu | Trp | Ser | Gln | Pro | Val | Cys | Phe | Gln | Ala | Pro | Gln |
| | | | 260 | | | | | 265 | | | | | 270 | |
| Arg | Gln | Gly | Pro | Leu | Ile | Pro | Pro | Trp | Gly | Trp | Pro | Gly | Asn | Thr |
| | | 275 | | | | | 280 | | | | | 285 | | |
| Leu | Val | Ala | Val | Ser | Ile | Phe | Leu | Leu | Leu | Thr | Gly | Pro | Thr | Tyr |
| | 290 | | | | | 295 | | | | | 300 | | | |
| Leu | Leu | Phe | Lys | Leu | Ser | Pro | Arg | Val | Lys | Arg | Ile | Phe | Tyr | Gln |
| 305 | | | | | 310 | | | | | 315 | | | | | 320 |
| Asn | Val | Pro | Ser | Pro | Ala | Met | Phe | Phe | Gln | Pro | Leu | Tyr | Ser | Val |
| | | | | 325 | | | | | 330 | | | | | 335 |
| His | Asn | Gly | Asn | Phe | Gln | Thr | Trp | Met | Gly | Ala | His | Arg | Ala | Gly |

```
Ser Gln Asp Cys Ala Gly Thr Pro Gln Gly Ala Leu Glu Pro Cys Val
            340                 345                 350
Gln Glu Ala Thr Ala Leu Leu Thr Cys Gly Pro Ala Arg Pro Trp Lys
            355                 360                 365
Ser Val Ala Leu Glu Glu Gln Glu Gly Pro Gly Thr Arg Leu Pro
    370                 375                 380
Gly Asn Leu Ser Ser Glu Asp Val Leu Pro Ala Gly Cys Thr Glu Trp
385                 390                 395                 400
Arg Val Gln Thr Leu Ala Tyr Leu Pro Gln Glu Asp Trp Ala Pro Thr
                405                 410                 415
Ser Leu Thr Arg Pro Ala Pro Pro Asp Ser Glu Gly Ser Arg Ser Ser
            420                 425                 430
Ser Ser Ser Ser Ser Ser Asn Asn Asn Tyr Cys Ala Leu Gly
            435                 440                 445
Cys Tyr Gly Gly Trp His Leu Ser Ala Leu Pro Gly Asn Thr Gln Ser
    450                 455                 460
Ser Gly Pro Ile Pro Ala Leu Ala Cys Gly Leu Ser Cys Asp His Gln
465                 470                 475                 480
Gly Leu Glu Thr Gln Gln Gly Val Ala Trp Val Leu Ala Gly His Cys
                485                 490                 495
Gln Arg Pro Gly Leu His Glu Asp Leu Gln Gly Met Leu Leu Pro Ser
            500                 505                 510
Val Leu Ser Lys Ala Arg Ser Trp Thr Phe
            515                 520

<210> SEQ ID NO 127
<211> LENGTH: 1947
<212> TYPE: DNA
<213> ORGANISM: Homo sapiens

<400> SEQUENCE: 127
agcagctctg taatgcgctt gtggtttcag atgtgggcgg cctgtgtgaa cctgtcgtgc      60
aaagctcacg tcaccaactg ctgcagttat ctcctgaatc aggctgaggg tctttgctgt     120
gcacccagag atagttgggt gacaaatcac ctccaggttg ggatgcctc agacttgtga     180
tgggactggg cagatgcatc tgggaaggct ggaccttgga gagtgaggcc ctgaggcgag     240
acatgggcac ctggctcctg gcctgcatct gcatctgcac ctgtgtctgc ttgggagtct     300
ctgtcacagg ggaaggacaa gggccaaggt ctagaacctt cacctgcctc accaacaaca     360
ttctcaggat cgattgccac tggtctgccc cagagctggg acagggctcc agcccctggc     420
tcctcttcac cagcaaccag gctcctggcg cacacataa gtgcatcttg cggggcagtg     480
agtgcaccgt cgtgctgcca cctgaggcag tgctcgtgcc atctgacaat ttcaccatca     540
ctttccacca ctgcatgtct gggagggagc aggtcagcct ggtggacccg agtacctgc     600
cccggagaca cgttaagctg gacccgccct ctgacttgca gagcaacatc agttctggcc     660
actgcatcct gacctggagc atcagtcctg ccttggagcc aatgaccaca cttctcagct     720
atgagctggc cttcaagaag caggaagagg cctgggagca ggcccagcac agggatcaca     780
ttgtcggggt gacctggctt atacttgaag cctttgagct ggaccctggc tttatccatg     840
aggccaggct gcgtgtccag atggccacac tggaggatga tgtggtagag gaggagcgtt     900
atacaggcca gtggagtgag tggagccagc ctgtgtgctt ccaggctccc agagacaag     960
gccctctgat cccacccctgg gggtggccag gcaacaccct tgttgctgtg tccatctttc    1020
```

-continued

```
tcctgctgac tggcccgacc tacctcctgt tcaagctgtc gcccagggtg aagagaatct    1080
tctaccagaa cgtgccctct ccagcgatgt tcttccagcc cctctacagt gtacacaatg    1140
ggaacttcca gacttggatg ggggcccaca gggccggtgt gctgttgagc caggactgtg    1200
ctggcacccc acagggagcc ttggagccct gcgtccagga ggccactgca ctgctcactt    1260
gtggcccagc gcgtccttgg aaatctgtgg ccctggagga ggaacaggag ggccctggga    1320
ccaggctccc ggggaacctg agctcagagg atgtgctgcc agcagggtgt acggagtgga    1380
gggtacagac gcttgcctat ctgccacagg aggactgggc cccacgtcc ctgactaggc     1440 cggctccccc agactcagag ggcagcagga gcagcagcag cagcagcagc agcagcaaca    1500
acaacaacta ctgtgccttg ggctgctatg ggggatggca cctctcagcc ctcccaggaa    1560
acacacagag ctctgggccc atcccagccc tggcctgtgg cctttcttgt gaccatcagg    1620
gcctggagac ccagcaagga gttgcctggg tgctggctgg tcactgccag aggcctgggc    1680
tgcatgagga cctccagggc atgttgctcc cttctgtcct cagcaaggct cggtcctgga    1740
cattctaggt ccctgactcg ccagatgcat catgtccatt tgggaaaat ggactgaagt     1800 ttctggagcc cttgtctgag actgaacctc ctgagaaggg gccctagca gcggtcagag     1860 gtcctgtctg gatggaggct ggaggctccc ccctcaaccc ctctgctcag tgcctgtggg    1920
gagcagcctc taccctcagc atcctgg                                        1947
```

<210> SEQ ID NO 128
<211> LENGTH: 120
<212> TYPE: PRT
<213> ORGANISM: Homo sapiens

<400> SEQUENCE: 128

```
Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Thr Phe Thr Gly Ser
            20                  25                  30

Trp Ile Glu Trp Ile Lys Gln Arg Pro Gly His Gly Leu Glu Trp Ile
        35                  40                  45

Gly Gln Ile Leu Pro Gly Ser Gly Ser Ala Tyr Tyr Asn Glu Lys Phe
    50                  55                  60

Lys Gly Lys Ala Thr Phe Thr Ala Asp Thr Ser Ser Lys Thr Val Tyr
65                  70                  75                  80

Ile Gln Leu Ile Ser Leu Thr Thr Glu Asp Ser Ala Ile Tyr Tyr Cys
                85                  90                  95

Ala Arg Glu Asp Asn Tyr Gly Ser Ser Ser Leu Ala Tyr Trp Gly Gln
            100                 105                 110

Gly Thr Leu Leu Thr Val Ser Ala
        115                 120
```

<210> SEQ ID NO 129
<211> LENGTH: 108
<212> TYPE: PRT
<213> ORGANISM: Homo sapiens

<400> SEQUENCE: 129

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
```

-continued

```
                35                  40                  45

Lys Tyr Ala Ser Glu Ser Ile Ser Gly Ile Pro Ser Arg Phe Ser Gly
 50                  55                  60

Gly Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Ser Asn Asn Trp Pro Leu
                 85                  90                  95

Thr Phe Gly Ala Gly Thr Lys Leu Glu Leu Lys Arg
            100                 105

<210> SEQ ID NO 130
<211> LENGTH: 11
<212> TYPE: PRT
<213> ORGANISM: Homo sapiens

<400> SEQUENCE: 130

Trp Gly Gln Gly Thr Leu Val Thr Val Ser Ser
 1               5                  10

<210> SEQ ID NO 131
<211> LENGTH: 11
<212> TYPE: PRT
<213> ORGANISM: Homo sapiens

<400> SEQUENCE: 131

Trp Gly Arg Gly Thr Leu Val Thr Val Ser Ser
 1               5                  10

<210> SEQ ID NO 132
<211> LENGTH: 11
<212> TYPE: PRT
<213> ORGANISM: Homo sapiens

<400> SEQUENCE: 132

Trp Gly Gln Gly Thr Met Val Thr Val Ser Ser
 1               5                  10

<210> SEQ ID NO 133
<211> LENGTH: 11
<212> TYPE: PRT
<213> ORGANISM: Homo sapiens

<400> SEQUENCE: 133

Trp Gly Gln Gly Thr Leu Val Thr Val Ser Ser
 1               5                  10

<210> SEQ ID NO 134
<211> LENGTH: 11
<212> TYPE: PRT
<213> ORGANISM: Homo sapiens

<400> SEQUENCE: 134

Trp Gly Gln Gly Thr Leu Val Thr Val Ser Ser
 1               5                  10

<210> SEQ ID NO 135
<211> LENGTH: 11
<212> TYPE: PRT
<213> ORGANISM: Homo sapiens

<400> SEQUENCE: 135

Trp Gly Gln Gly Thr Thr Val Thr Val Ser Ser
 1               5                  10
```

```
<210> SEQ ID NO 136
<211> LENGTH: 10
<212> TYPE: PRT
<213> ORGANISM: Homo sapiens

<400> SEQUENCE: 136

Phe Gly Gln Gly Thr Lys Val Glu Ile Lys
1               5                   10

<210> SEQ ID NO 137
<211> LENGTH: 10
<212> TYPE: PRT
<213> ORGANISM: Homo sapiens

<400> SEQUENCE: 137

Phe Gly Gln Gly Thr Lys Leu Glu Ile Lys
1               5                   10

<210> SEQ ID NO 138
<211> LENGTH: 10
<212> TYPE: PRT
<213> ORGANISM: Homo sapiens

<400> SEQUENCE: 138

Phe Gly Pro Gly Thr Lys Val Asp Ile Lys
1               5                   10

<210> SEQ ID NO 139
<211> LENGTH: 10
<212> TYPE: PRT
<213> ORGANISM: Homo sapiens

<400> SEQUENCE: 139

Phe Gly Gly Gly Thr Lys Val Glu Ile Lys
1               5                   10

<210> SEQ ID NO 140
<211> LENGTH: 10
<212> TYPE: PRT
<213> ORGANISM: Homo sapiens

<400> SEQUENCE: 140

Phe Gly Gln Gly Thr Arg Leu Glu Ile Lys
1               5                   10
```

What is claimed:

1. A chimeric antibody comprising the variable heavy chain of antibody MH9A3 as shown in SEQ ID NO:3 and the variable light chain of antibody MH9A3 as shown in SEQ ID NO:5.

2. An isolated antibody or antibody fragment thereof that specifically binds to IL-9,
wherein the antibody or fragment thereof comprises a heavy chain and a light chain variable domain,
wherein the antibody or fragment thereof comprises six complementarity determining regions (CDRs), and
wherein three of the six CDRs comprise amino acid sequences of the:
(a) variable heavy chain CDRs from antibody MH9A3;
(b) variable heavy chain CDRs from antibody MH9D1;
(c) variable heavy chain CDRs from antibody MH9L1;
(d) variable light chain CDRs from antibody MH9A3;
(e) variable light chain CDRs from antibody MH9D1; or
(f) variable light chain CDRs from antibody MH9L1;
wherein the MH9A3 antibody variable heavy chain CDRs are shown as amino acid residues 26-35 of SEQ ID NO:3, amino acid residues 50-66 of SEQ ID NO:3, and amino acid residues 99-111 of SEQ ID NO:3;
wherein the MH9A3 antibody variable light chain CDRs are shown as amino acid residues 24-34 of SEQ ID NO:5, amino acid residues 50-56 of SEQ ID NO:5, and amino acid residues 89-97 of SEQ ID NO:5;

wherein MH9D1 antibody variable heavy chain CDRs are shown as amino acid residues 26-35 of SEQ ID NO:4, amino acid residues 50-66 of SEQ ID NO:4, and amino acid residues 99-108 of SEQ ID NO:4;

wherein MH9D1 antibody variable light chain CDRs are shown as amino acid residues 24-34 of SEQ ID NO:6, amino acid residues 50-56 of SEQ ID NO:6, and amino acid residues 89-97 of SEQ ID NO:6;

wherein MH9L1 antibody variable heavy chain CDRs are shown as amino acid residues 26-35 of SEQ ID NO:128, amino acid residues 50-66 of SEQ ID NO:128, and amino acid residues 99-109 of SEQ ID NO:128; and wherein MH9L1 antibody variable light chain CDRs are shown as amino acid residues 24-34 of SEQ ID NO:129, amino acid residues 50-56 of SEQ ID NO:129, and amino acid residues 89-97 of SEQ ID NO:129.

3. The isolated antibody or fragment of claim 2 wherein the variable heavy chain CDRs are from antibody MH9A3.

4. The isolated antibody or fragment of claim 2 wherein the variable heavy chain CDRs are from antibody MH9D1.

5. The isolated antibody or fragment of claim 2 wherein the variable heavy chain CDRs are from antibody MH9L1.

6. The isolated antibody or fragment of claim 2 wherein the variable light chain CDRs are from antibody MH9A3.

7. The isolated antibody or fragment of claim 2 wherein the variable light chain CDRs are from antibody MH9D1.

8. The isolated antibody or fragment of claim 2 wherein the variable light chain CDRs are from antibody MH9L1.

9. The isolated antibody or fragment of claim 3 wherein the variable light chain comprises the amino acid sequence of at least one CDR of the MH9A3 antibody variable light chain.

10. The isolated antibody or fragment of claim 4 wherein the variable light chain comprises the amino acid sequence of at least one CDR of the MH9D1 antibody variable light chain.

11. The isolated antibody or fragment of claim 5 wherein the variable light chain comprises the amino acid sequence of at least one CDR of the MH9L1 antibody variable light chain.

12. The isolated antibody or fragment of claim 6 wherein the variable heavy chain comprises the amino acid sequence of at least one CDR of the MH9A3 antibody variable heavy chain.

13. The isolated antibody or fragment of claim 7 wherein the variable heavy chain comprises the amino acid sequence of at least one CDR of the MH9D1 antibody variable heavy chain.

14. The isolated antibody or fragment of claim 8 wherein the variable heavy chain comprises the amino acid sequence of at least one CDR of the MH9L1 antibody variable heavy chain.

15. The isolated antibody or fragment of claim 3 wherein the variable light chain comprises the amino acid sequence of at least two CDRs of the MH9A3 antibody variable light chain.

16. The isolated antibody or fragment of claim 4 wherein the variable light chain comprises the amino acid sequence of at least two CDRs of the MH9D1 antibody variable light chain.

17. The isolated antibody or fragment of claim 5 wherein the variable light chain comprises the amino acid sequence of at least two CDRs of the MH9L1 antibody variable light chain.

18. The isolated antibody or fragment of claim 6 wherein the variable heavy chain comprises the amino acid sequence of at least two CDRs of the MH9A3 antibody variable heavy chain.

19. The isolated antibody or fragment of claim 7 wherein the variable heavy chain comprises the amino acid sequence of at least two CDRs of the MH9D1 antibody variable heavy chain.

20. The isolated antibody or fragment of claim 8 wherein the variable heavy chain comprises the amino acid sequence of at least two CDRs of the MH9L1 antibody variable heavy chain.

21. The isolated antibody or fragment of claim 3 wherein the variable light chain comprises the amino acid sequence of three CDRs of the MH9A3 antibody variable light chain.

22. The isolated antibody or fragment of claim 4 wherein the variable light chain comprises the amino acid sequence of three CDRs of the MH9D1 antibody variable light chain.

23. The isolated antibody or fragment of claim 5 wherein the variable light chain comprises the amino acid sequence of three CDRs of the MH9L1 antibody variable light chain.

24. The isolated antibody or fragment of claim 2 wherein the antibody or is a monoclonal antibody.

25. The isolated antibody or fragment of claim 2 wherein the antibody or is a humanized antibody.

26. The isolated antibody or fragment of claim 2 wherein the antibody fragment is an scFv.

27. The isolated antibody or fragment of claim 2 wherein the antibody fragment is a Fab fragment.

28. The isolated antibody or fragment of claim 2 wherein the antibody fragment is an Fab' fragment.

29. The isolated antibody or fragment of claim 2 wherein the antibody fragment is an F(ab)2.

30. The isolated antibody or fragment of claim 2 wherein the antibody fragment is an Fv.

31. The isolated antibody or fragment of claim 2 wherein the antibody fragment is a disulfide linked Fv.

32. The isolated antibody or fragment of claim 2 wherein the antibody or antibody fragment is a bi-specific antibody.

33. The isolated antibody or fragment of claim 2 wherein the antibody or antibody fragment has a dissociation constant ($K_d$) between $10^{-7}$ M and $10^{-8}$ M.

34. The isolated antibody or fragment of claim 2 wherein the antibody or antibody fragment has a dissociation constant ($K_d$) between $10^{-8}$ M and $10^{-9}$ M.

35. The isolated antibody or fragment of claim 2 wherein the antibody or antibody fragment has a dissociation constant ($K_d$) between $10^{-9}$ M and $10^{-10}$ M.

36. The isolated antibody or fragment of claim 2 wherein the antibody or antibody fragment has a dissociation constant ($K_d$) between $10^{-10}$ M and $10^{-11}$ M.

37. The isolated antibody or fragment of claim 2 wherein the antibody or antibody fragment has a dissociation constant ($K_d$) between $10^{-11}$ M and $10^{-12}$ M.

38. The isolated antibody or fragment of claim 2 wherein the antibody or antibody fragment has a dissociation constant ($K_d$) between $10^{-12}$ M and $10^{-13}$ M.

39. The isolated antibody or fragment of claim 2 wherein the antibody or antibody fragment has a dissociation constant ($K_d$) between $10^{-13}$ M and $10^{-14}$ M.

40. The isolated antibody or fragment of claim 2 which inhibits IL-9 activity.

41. A pharmaceutical composition comprising the isolated antibody or fragment thereof as recited in claim 2 and a pharmaceutically acceptable carrier.

42. The pharmaceutical composition of claim 41 wherein the isolated antibody or fragment thereof comprises all six CDRs are from antibody MH9A3.

43. The pharmaceutical composition of claim 41 wherein the isolated antibody or fragment thereof comprises all six CDRs are from antibody MH9D1.

44. The pharmaceutical composition of claim 41 wherein the isolated antibody or fragment thereof comprises all six CDRs are from antibody MH9L1.

* * * * *

UNITED STATES PATENT AND TRADEMARK OFFICE
CERTIFICATE OF CORRECTION

PATENT NO. : 7,371,383 B2
APPLICATION NO. : 10/412703
DATED : May 13, 2008
INVENTOR(S) : Jennifer Lynne Reed et al.

It is certified that error appears in the above-identified patent and that said Letters Patent is hereby corrected as shown below:

Column 8, line 39, replace "SEQ ID NO: 29" with --SEQ ID NO: 30--.

In the sequence listing:

For SEQ ID NO: 4, please replace the following:

"<210> SEQ ID NO 4
<211> LENGTH: 88
<212> TYPE: PRT
<213> ORGANISM: Homo sapiens

<400> SEQUENCE: 4

Val Ser Gly Ala Val Arg Gly Thr Ser Val Lys Met Ser Cys Lys Ala
1               5                   10                  15

Ser Gly Thr Thr Asn Tyr Tyr Gly Trp Ala Lys Arg Gly His Gly Trp
            20                  25                  30

Gly Asp Tyr Gly Ser Thr Tyr Asn Tyr Asn Lys Lys Gly Lys Ala Thr
        35                  40                  45

Thr Ala Asp Lys Ser Ser Ser Thr Ala Tyr Met Ser Ser Thr Ser Asp
    50                  55                  60

Ser Ala Tyr Tyr Cys Ala Arg Ser Asp Asp Gly Tyr Tyr Gly Tyr Trp
65                  70                  75                  80

Gly Gly Thr Val Thr Val Ser Ala"
                85 to
--<210> SEQ ID NO 4
<211> LENGTH: 119
<212> TYPE: PRT
<213> ORGANISM: Homo sapiens

<400> SEQUENCE: 4

UNITED STATES PATENT AND TRADEMARK OFFICE
CERTIFICATE OF CORRECTION

PATENT NO. : 7,371,383 B2
APPLICATION NO. : 10/412703
DATED : May 13, 2008
INVENTOR(S) : Jennifer Lynne Reed et al.

It is certified that error appears in the above-identified patent and that said Letters Patent is hereby corrected as shown below:

Continued from page 1:

Gln Val Gln Leu Gln Gln Ser Gly Ala Glu Leu Val Arg Pro Gly Thr
1               5                   10                  15

Ser Val Lys Met Ser Cys Lys Ala Ser Gly Phe Thr Phe Thr Asn Tyr
            20                  25                  30

Tyr Ile Gly Trp Ala Lys Gln Arg Pro Gly His Gly Leu Glu Trp Ile
        35                  40                  45

Gly Asp Ile Tyr Pro Gly Ser Thr Tyr Ile Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Phe Ser Ser Leu Thr Ser Glu Asp Ser Ala Ile Tyr Tyr Cys
            85                  90                  95

Ala Arg Ser Asp Asp Gly Tyr Tyr Gly Phe Pro Tyr Trp Gly Gln Gly
                100                 105                 110

Thr Leu Val Thr Val Ser Ala--.
        115

For SEQ ID NO: 7, please replace the following:

"<210> SEQ ID NO 7
 <211> LENGTH: 87
 <212> TYPE: PRT
 <213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Trp Val
            20                  25                  30

UNITED STATES PATENT AND TRADEMARK OFFICE
CERTIFICATE OF CORRECTION

PATENT NO. : 7,371,383 B2
APPLICATION NO. : 10/412703
DATED : May 13, 2008
INVENTOR(S) : Jennifer Lynne Reed et al.

It is certified that error appears in the above-identified patent and that said Letters Patent is hereby corrected as shown below:

Continued from page 2:

Arg Gln Ala Pro Gly Gln Gly Leu Glu Trp Met Gly Arg Val Thr Ile
     35               40             45

Thr Ala Asp Lys Ser Thr Ser Thr Ala Tyr Met Glu Leu Ser Ser Leu
    50             55           60

Arg Ser Glu Asp Thr Ala Val Tyr Tyr Cys Ala Arg Trp Gly Gln Gly
65            70            75           80

Thr Leu Val Thr Val Ser Ser"
          85 to
--<210>   SEQ ID NO 7
  <211>   LENGTH: 122
  <212>   TYPE: PRT
  <213>   ORGANISM: Homo sapiens

<400>   SEQUENCE: 7

Gln Val Gln Leu Val Gln Ser Gly Ala Glu Val Lys Lys Pro Gly Ser
1           5           10           15

Ser Val Lys Val Ser Cys Lys Ala Ser Gly Tyr Thr Phe Thr Gly Tyr
      20           25           30

Trp Ile Glu Trp Val Arg Gln Ala Pro Gly Gln Gly Leu Glu Trp Met
     35           40            45

Gly Glu Ile Leu Pro Gly Ser Gly Thr Thr Asn Tyr Asn Glu Lys Phe
   50           55           60

Lys Gly Arg Val Thr Ile Thr Ala Asp Lys Ser Thr Ser Thr Ala Tyr
65            70            75           80

Met Glu Leu Ser Ser Leu Arg Ser Glu Asp Thr Ala Val Tyr Tyr Cys
       85            90           95

UNITED STATES PATENT AND TRADEMARK OFFICE
CERTIFICATE OF CORRECTION

PATENT NO.         : 7,371,383 B2
APPLICATION NO.    : 10/412703
DATED              : May 13, 2008
INVENTOR(S)        : Jennifer Lynne Reed et al.

It is certified that error appears in the above-identified patent and that said Letters Patent is hereby corrected as shown below:

Continued from page 3:

Ala Arg Ala Asp Tyr Tyr Gly Ser Ser Tyr Val Lys Phe Asp Tyr Trp
         100                 105                 110

Gly Gln Gly Thr Leu Val Thr Val Ser Ser--.
         115             120

For SEQ ID NO: 24, at position 100, replace the amino acid "Ala" with --Gly--.

For SEQ ID NO: 24, at position 104, replace the amino acid "Leu" with --Val--.

For SEQ ID NO: 24, at position 106, replace the amino acid "Leu" with --Ile--.

For SEQ ID NO: 32, at position 3, replace the amino acid "Thr" with --Val--.

For SEQ ID NO: 32, at position 4, replace the amino acid "Leu" with --Met--.

For SEQ ID NO: 32, at position 60, replace the amino acid "Asp" with --Ala--.

For SEQ ID NO: 32, at position 70, replace the amino acid "Asp" with --Glu--.

For SEQ ID NO: 32, at position 77, replace the amino acid "Arg" with --Ser--.

For SEQ ID NO: 32, at position 80, replace the amino acid "Pro" with --Ser--.

UNITED STATES PATENT AND TRADEMARK OFFICE
CERTIFICATE OF CORRECTION

PATENT NO. : 7,371,383 B2
APPLICATION NO. : 10/412703
DATED : May 13, 2008
INVENTOR(S) : Jennifer Lynne Reed et al.

It is certified that error appears in the above-identified patent and that said Letters Patent is hereby corrected as shown below:

Continued from page 4:

For SEQ ID NO: 32, at position 85, replace the amino acid "Thr" with --Val--.

Signed and Sealed this

Sixth Day of January, 2009

JON W. DUDAS
*Director of the United States Patent and Trademark Office*